(12) United States Patent
Jin et al.

(10) Patent No.: US 11,800,800 B1
(45) Date of Patent: Oct. 24, 2023

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Hyo Min Jin, Cheonan-si (KR); Jae Ho Kim, Cheonan-si (KR); Hyung Dong Lee, Cheonan-si (KR); Ki Ho So, Cheonan-si (KR); Sun-Hee Lee, Cheonan-si (KR); Yun Suk Lee, Cheonan-si (KR); Soung Yun Mun, Cheonan-si (KR); Hak Young Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 17/711,433

(22) Filed: Apr. 1, 2022

Related U.S. Application Data

(63) Continuation-in-part of application No. 17/212,886, filed on Mar. 25, 2021, now Pat. No. 11,678,577, (Continued)

(30) Foreign Application Priority Data

Oct. 26, 2020 (KR) .................. 10-2020-0139441

(51) Int. Cl.
*C07D 251/24* (2006.01)
*H01L 51/00* (2006.01)
(Continued)

(52) U.S. Cl.
CPC ....... *H10K 85/6574* (2023.02); *C07D 251/24* (2013.01); *C09K 11/06* (2013.01); *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01);
(Continued)

(58) Field of Classification Search
CPC .................................................. C07D 251/24
See application file for complete search history.

(56) References Cited

U.S. PATENT DOCUMENTS

2018/0072695 A1  3/2018  Byun et al.
2018/0123048 A1  5/2018  So et al.
(Continued)

FOREIGN PATENT DOCUMENTS

KR  10-2009-0079134 A   7/2009
KR  10-2016-0111780 A   9/2016
(Continued)

OTHER PUBLICATIONS

STN Search (Apr. 7, 2021).
SciFinder Search (Apr. 7, 2021).

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound capable of improving luminous efficiency, stability and lifespan of an organic electronic element employing the same, an organic electronic element employing the same, and an electronic device thereof.

13 Claims, 2 Drawing Sheets

Related U.S. Application Data which is a continuation of application No. 17/096,790, filed on Nov. 12, 2020, now Pat. No. 11,063,226.

(51) Int. Cl.
| | |
|---|---|
| *H01L 51/50* | (2006.01) |
| *H10K 85/60* | (2023.01) |
| *C09K 11/06* | (2006.01) |
| *H10K 50/11* | (2023.01) |
| *H10K 50/15* | (2023.01) |
| *H10K 50/16* | (2023.01) |
| *H10K 50/18* | (2023.01) |
| *H10K 101/10* | (2023.01) |
| *H10K 101/00* | (2023.01) |

(52) U.S. Cl.
CPC ...... *C09K 2211/1018* (2013.01); *H10K 50/11* (2023.02); *H10K 50/15* (2023.02); *H10K 50/16* (2023.02); *H10K 50/18* (2023.02); *H10K 2101/10* (2023.02); *H10K 2101/90* (2023.02)

(56) References Cited

U.S. PATENT DOCUMENTS

2018/0151806 A2   5/2018   Park et al.
2018/0261774 A1   9/2018   Park et al.

FOREIGN PATENT DOCUMENTS

| WO | 2017/171420 A1 | 10/2017 | | |
| WO | 2019/124902 A1 | 6/2019 | | |
| WO | WO-2020032424 A1 * | 2/2020 | ......... | H01L 51/0071 |

\* cited by examiner

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATIONS

This application is a continuation-in-part of U.S. patent application Ser. No. 17/212,886 filed on Mar. 25, 2021, which was a continuation of U.S. patent application Ser. No. 17/096,790 filed on Nov. 12, 2020, now U.S. Pat. No. 11,063,226 issued on Jul. 13, 2021, which claims the benefit of priority from Korean Patent Application No. 10-2020-0139441 filed on Oct. 26, 2020, the contents of each of which are incorporated herein by reference in its entirety.

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

In other words, in order to fully exhibit the excellent characteristics of an organic electronic element, the material constituting the organic material layer in the device, such as a hole injection material, a hole transport material, a light emitting material, an electron transport material, an electron injection material, etc., is supported by a stable and efficient material. should take precedence, but the development of a stable and efficient organic material layer material for an organic electronic device has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound, an organic electronic element using the same, and an electronic device thereof.

Technical Solution

The present invention provides a compound represented by Formula (2).

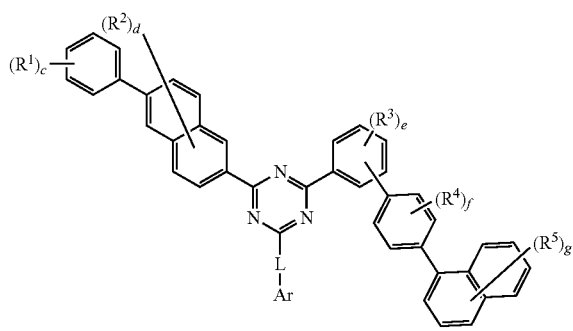

Formula (2)

In another aspect, the present invention provides an organic electronic element comprising the compound represented by Formula (2) and an electronic device thereof.

Effects of the Invention

By using the compound according to the present invention, high luminous efficiency, low driving voltage and high heat resistance of the device can be achieved, and color purity and lifespan of the device can be greatly improved.

Figure 1:
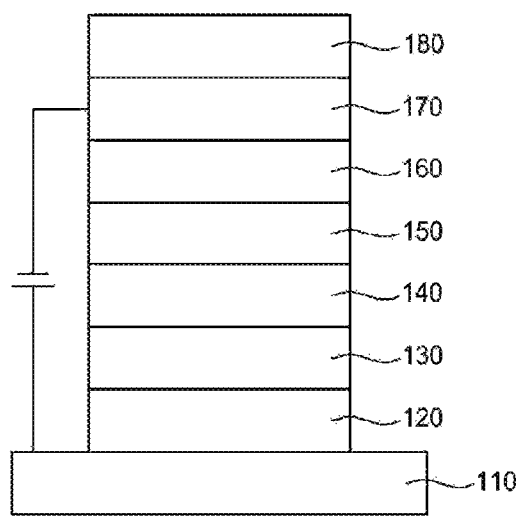
FIG. 1 to FIG. 3 are exemplary views of an organic electroluminescent device according to the present invention.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST1: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

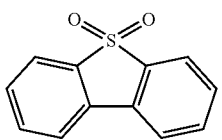 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

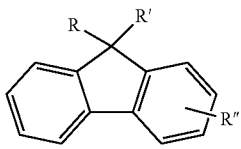

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro' and 'tri-spiro', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

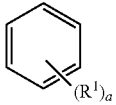

Here, when a is an integer of zero, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

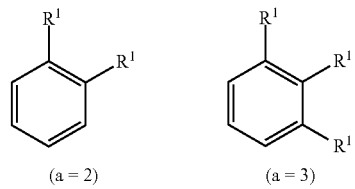

Hereinafter, a compound according to an aspect of the present invention and an organic electronic element including the same will be described.

The present invention provides a compound represented by Formula (2).

Formula (2)

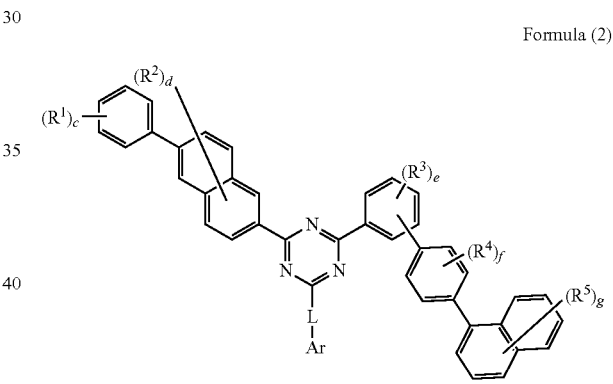

{Wherein,

1) $R^1$, $R^2$, $R^3$, $R^4$ and $R^5$ are the same or different from each other, and independently of each other are hydrogen or deuterium;

2) L is a single bond; or $C_6$-$C_{60}$ arylene group;

3) Ar is a $C_6$-$C_{60}$ aryl group;

4) c is an integer of 0 to 5, d is an integer of 0 to 6, e and f are each independently an integer of 0 to 4, and g is an integer of 0 to 7, 5) wherein the arylene group and the aryl group may be further substituted with one or more substituents selected from the group consisting of deuterium; $C_6$-$C_{20}$ aryl group; $C_6$-$C_{20}$ aryl group substituted with deuterium;}

Also, the present invention provides a compound in which Formula (2) is represented by Formula (2-1) or Formula (2-3).

Formula (2-1)
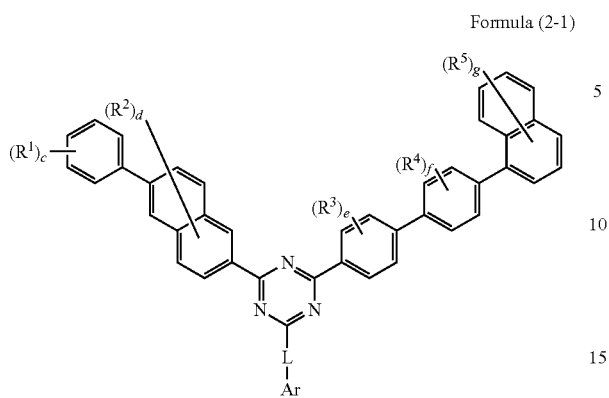
Formula (2-2)
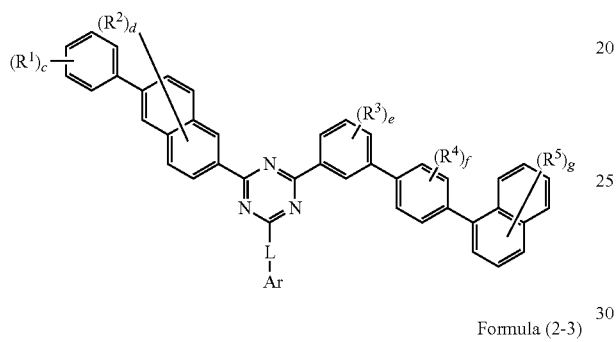
Formula (2-3)
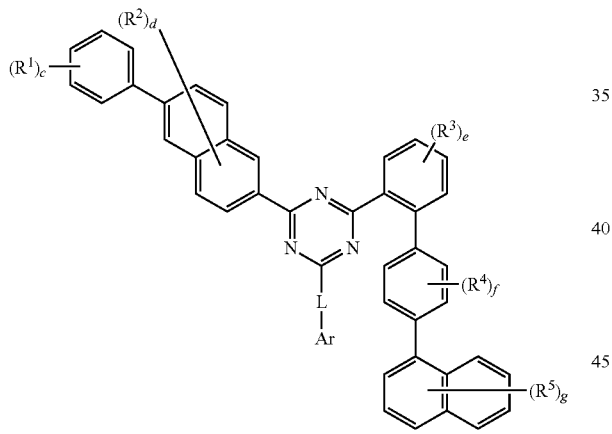
{wherein,
R$^1$, R$^2$, R$^3$, R$^4$, R$^5$, L, Ar, c, d, e, f and g are the same as defined above.}
Also, the present invention provides a compound in which L is represented by any one of the following Formulas a-1 to a-20.
<Formula a-1>
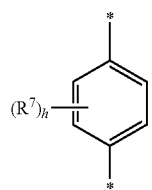
<Formula a-2>
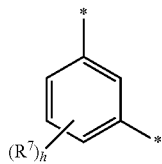
<Formula a-3>
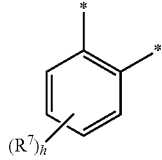
<Formula a-4>
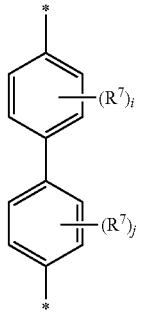
<Formula a-5>
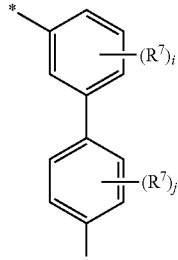
<Formula a-6>
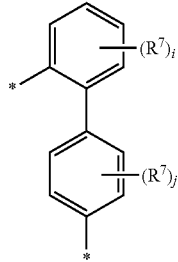
<Formula a-7>
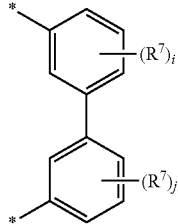

<Formula a-8>
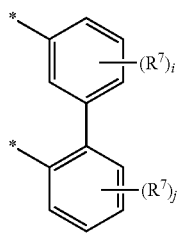

<Formula a-9>
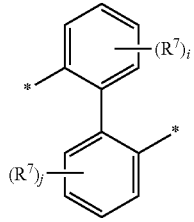

<Formula a-10>
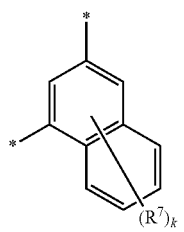

<Formula a-11>
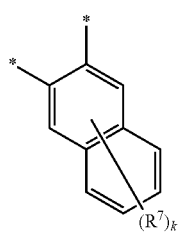

<Formula a-12>
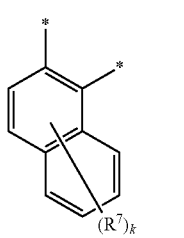

<Formula a-13>
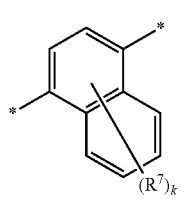

<Formula a-14>
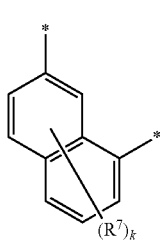

<Formula a-15>
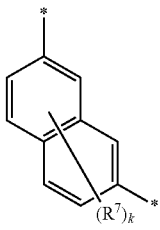

<Formula a-16>
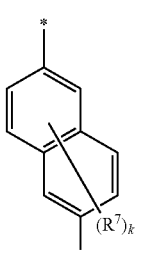

<Formula a-17>
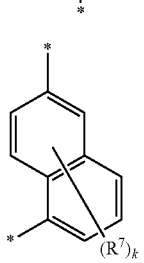

<Formula a-18>
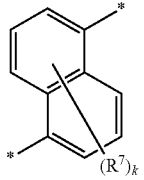

<Formula a-19>
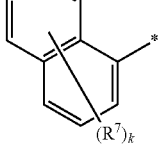

<Formula a-20>
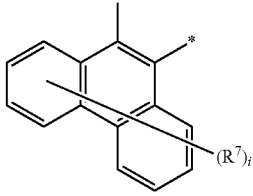

{wherein,
1) $R^7$ is selected from the group consisting of a deuterium; a $C_6$~$C_{20}$ aryl group; a $C_6$~$C_{20}$ aryl group substituted with deuterium;
2) h, i and j are each independently an integer from 0 to 4, k is an integer from 0 to 6, l is an integer from 0 to 8,
3) * means a position where triazine or Ar is bonded.}

Also, the present invention provides a compound in which Ar is represented by any one of the following formulas b-1 to b-8.

<Formula b-1>

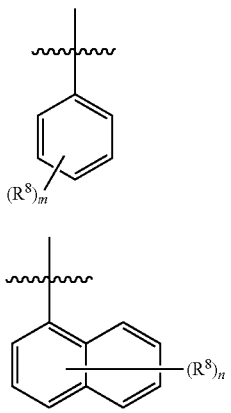

<Formula b-2>

<Formula b-3>

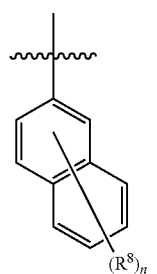

<Formula b-4>

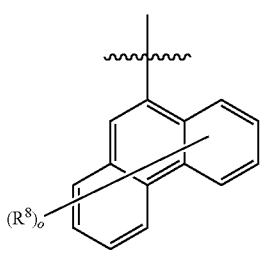

<Formula b-5>

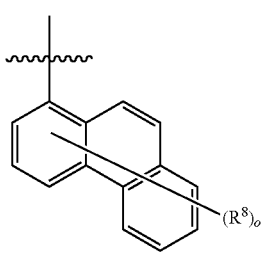

<Formula b-6>

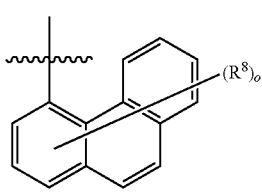

<Formula b-7>

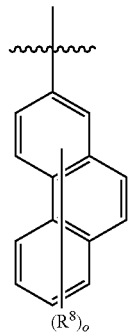

<Formula b-8>

{wherein,
1) $R^8$ is selected from the group consisting of a deuterium; a $C_6$~$C_{20}$ aryl group; a $C_6$~$C_{20}$ aryl group substituted with deuterium;
2) m is an integer from 0 to 5, n is an integer from 0 to 7, o is an integer from 0 to 9,
3) ⌇⌇ means the position where it is combined with L.}

Also, the present invention provides a compound having a reorganization energy value of 0.240 to 0.300 of the compound represented by Formula (2). Preferably, it may be a compound having a rearrangement energy value of 0.246 to 0.300.

Also, the present invention provides a compound in which the compound represented by Formula (2) is represented by any one of the following compounds S-1 to S-56.

S-1

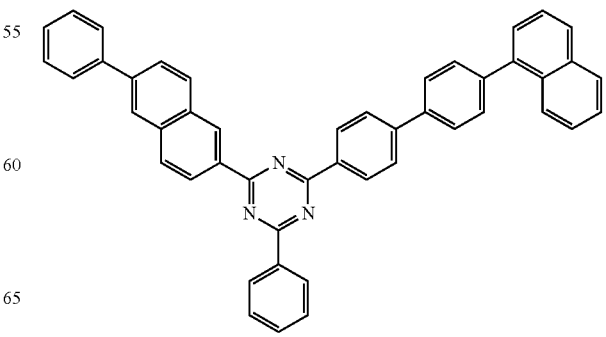

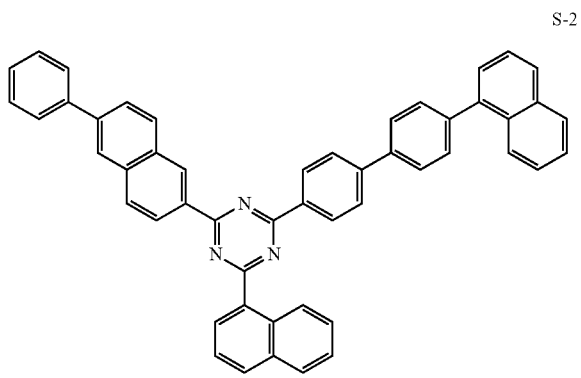
S-2
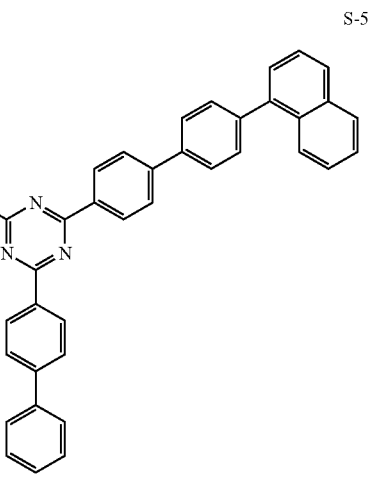
S-5
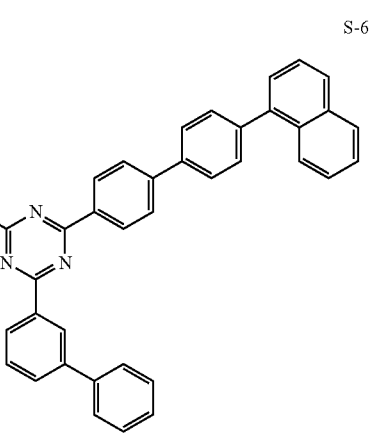
S-6
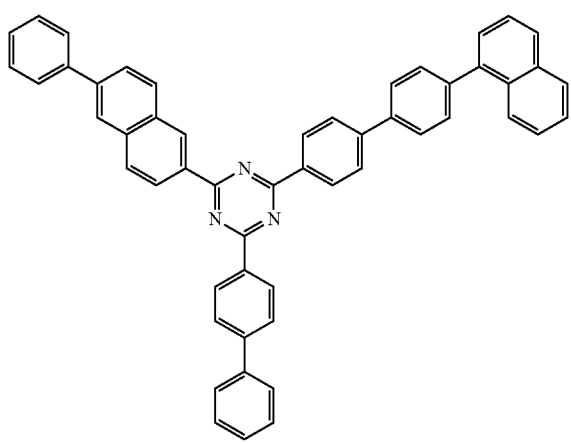
S-3
S-4
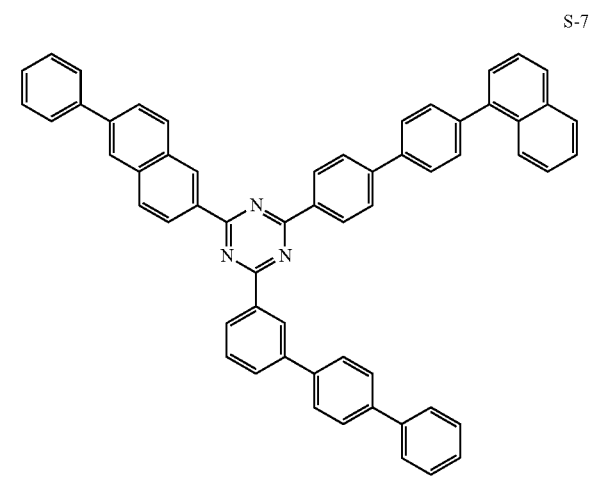
S-7

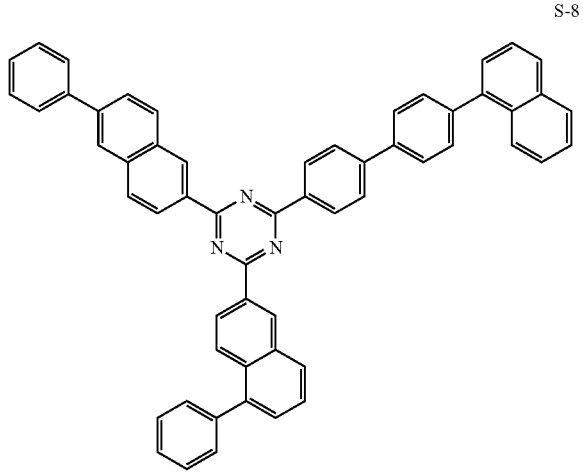
S-8
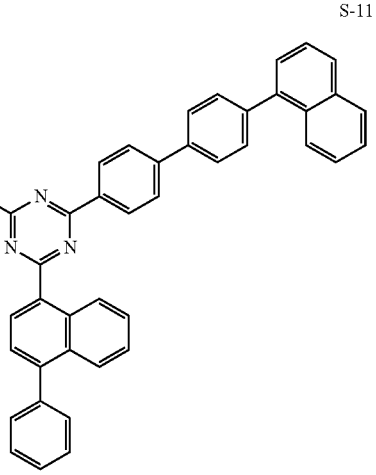
S-11
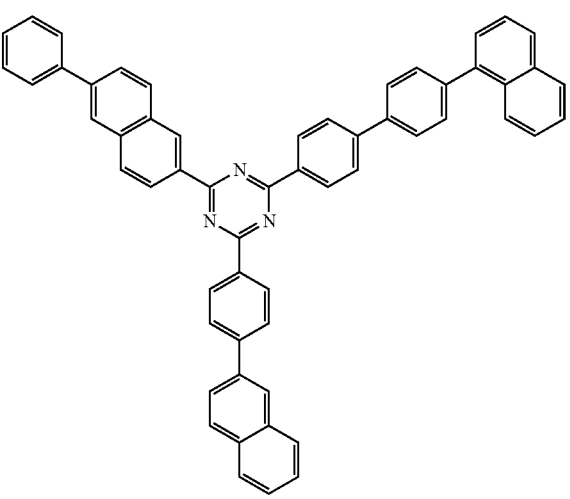
S-9
S-12
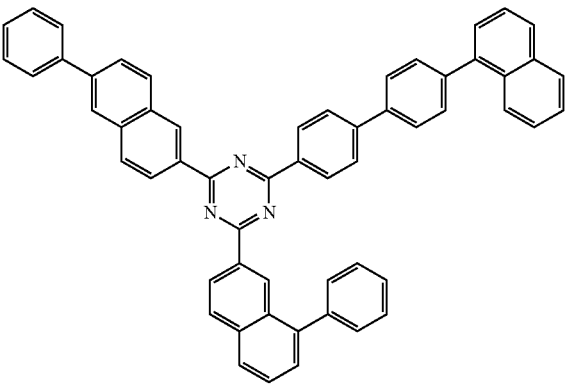
S-10
S-13

S-14
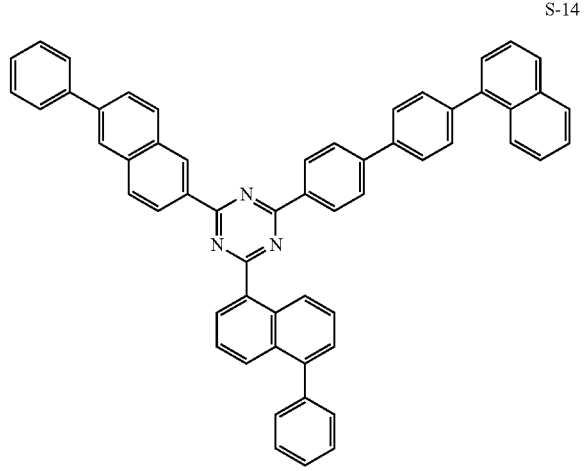
S-15
S-16
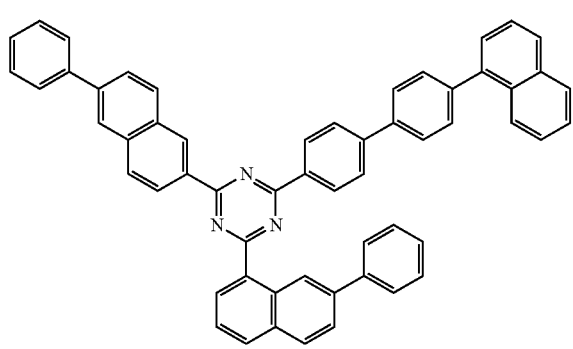
S-17
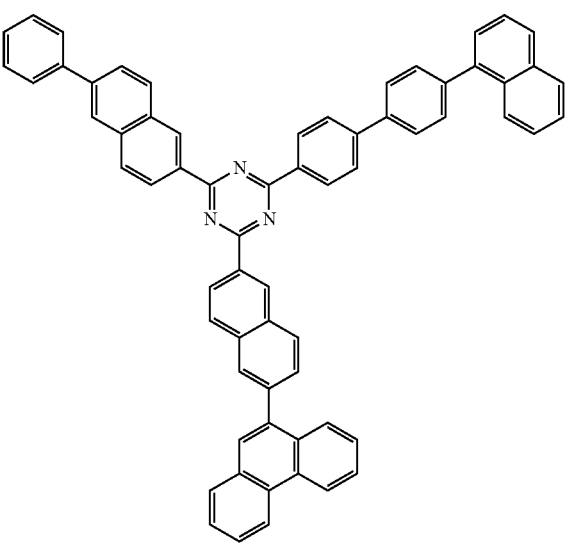
S-18
S-19
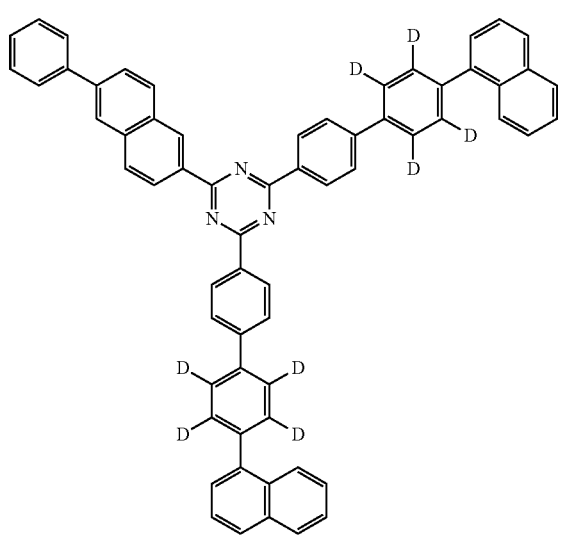

S-20
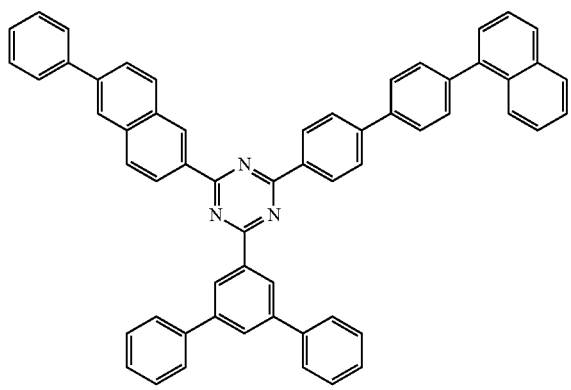
S-24
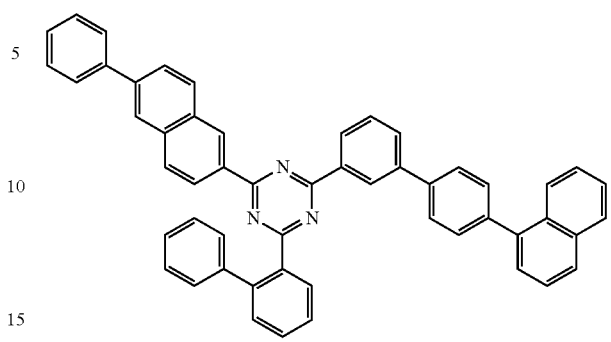
S-21
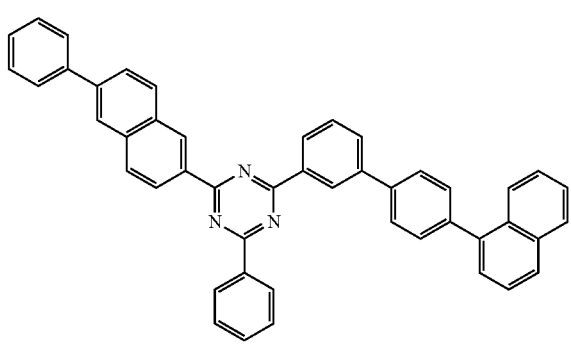
S-25
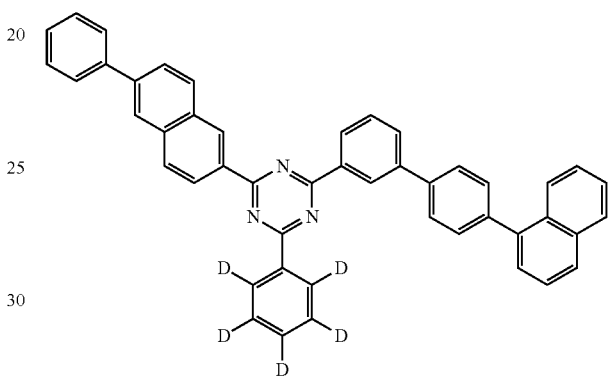
S-22
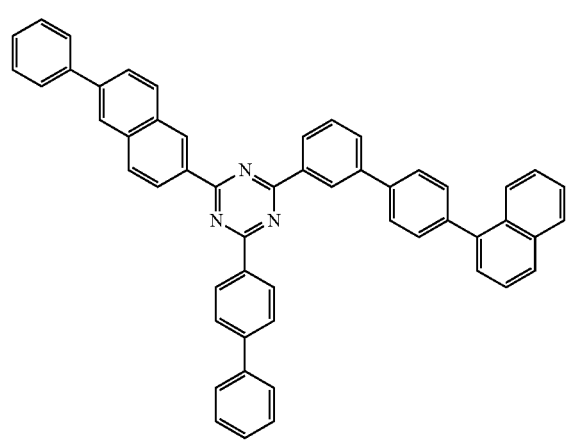
S-26
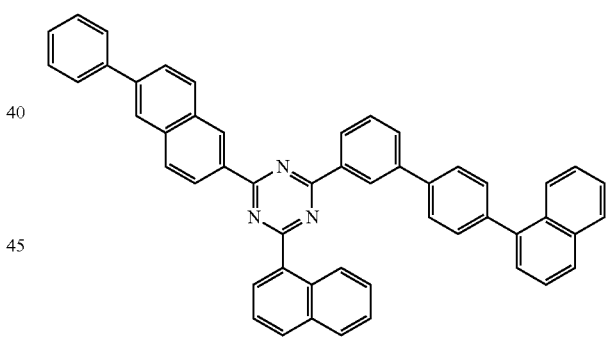
S-23
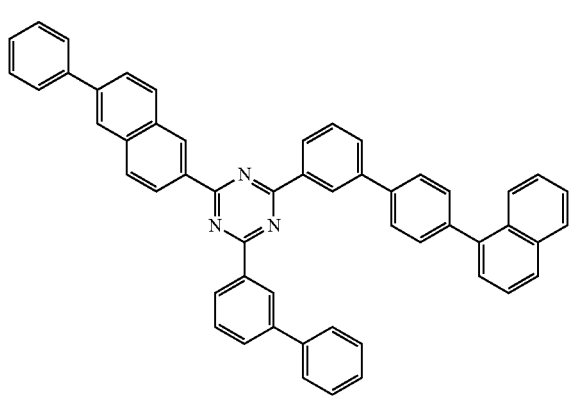
S-27
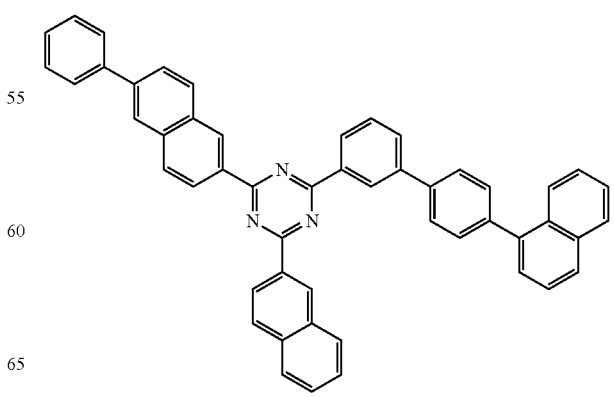

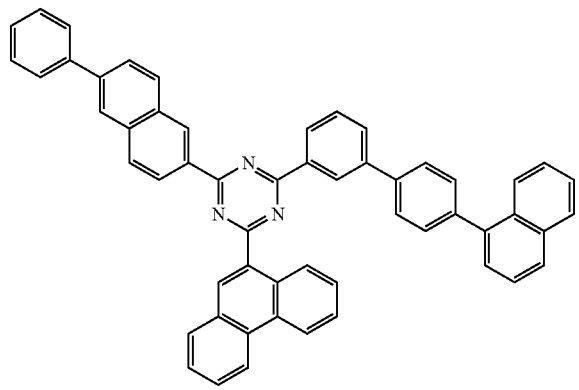
S-28
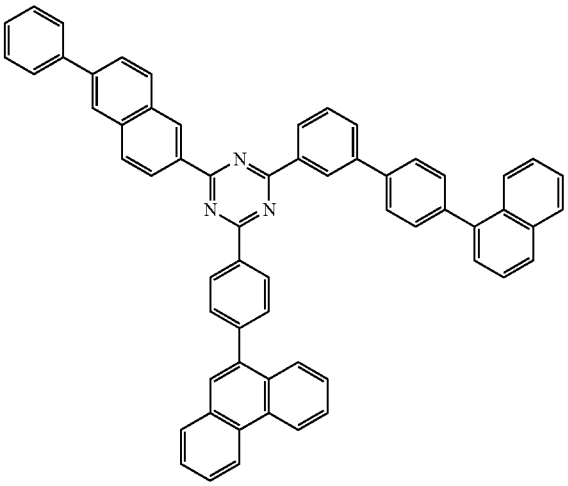
S-31
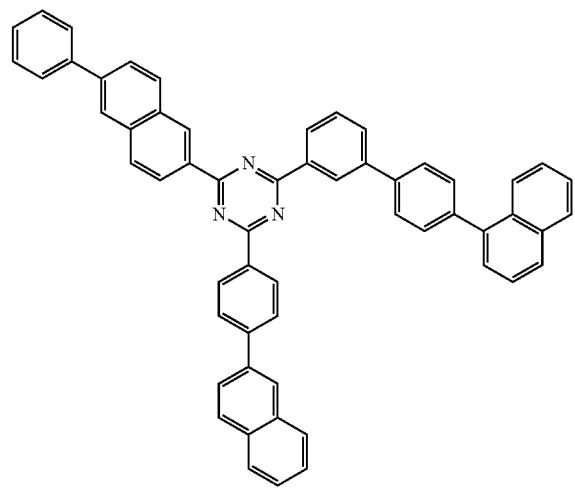
S-29
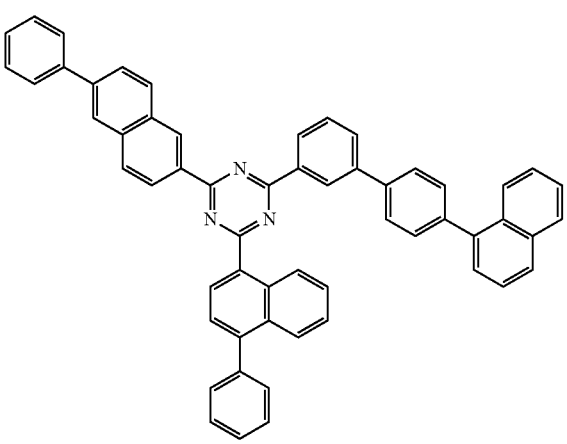
S-32
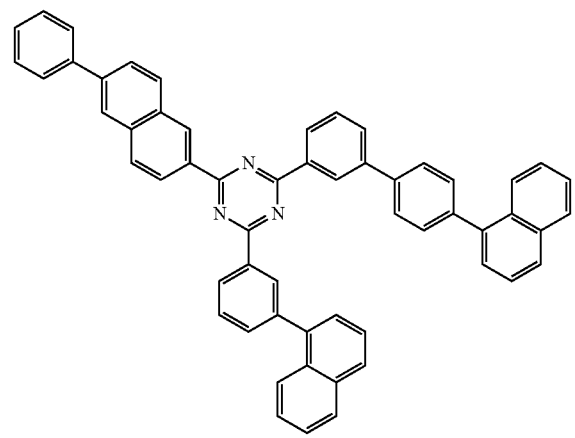
S-30
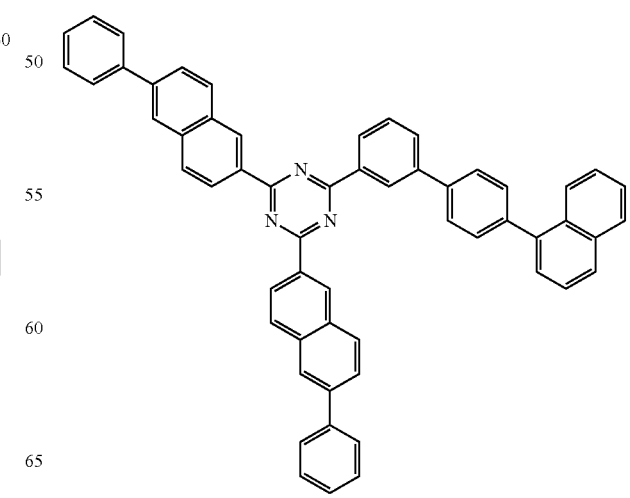
S-33

S-34
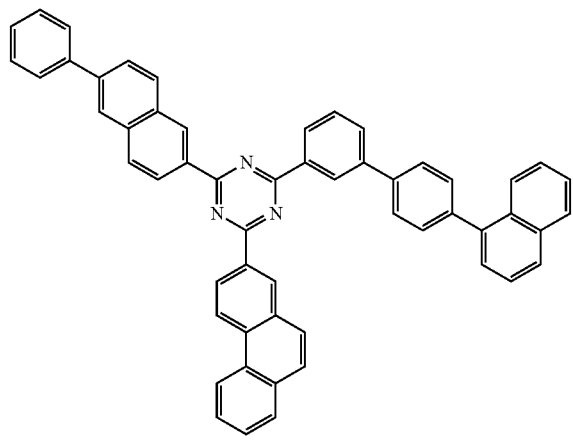
S-37
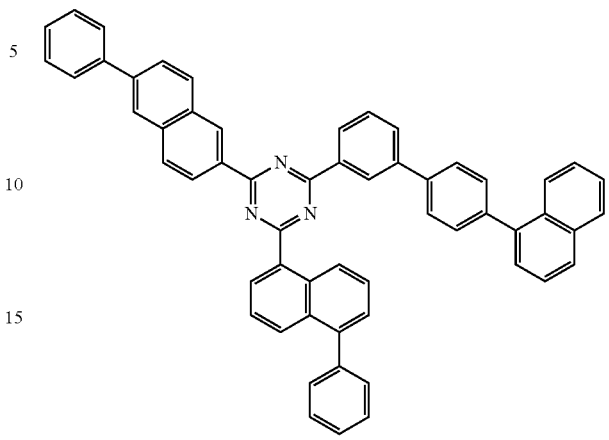
S-35
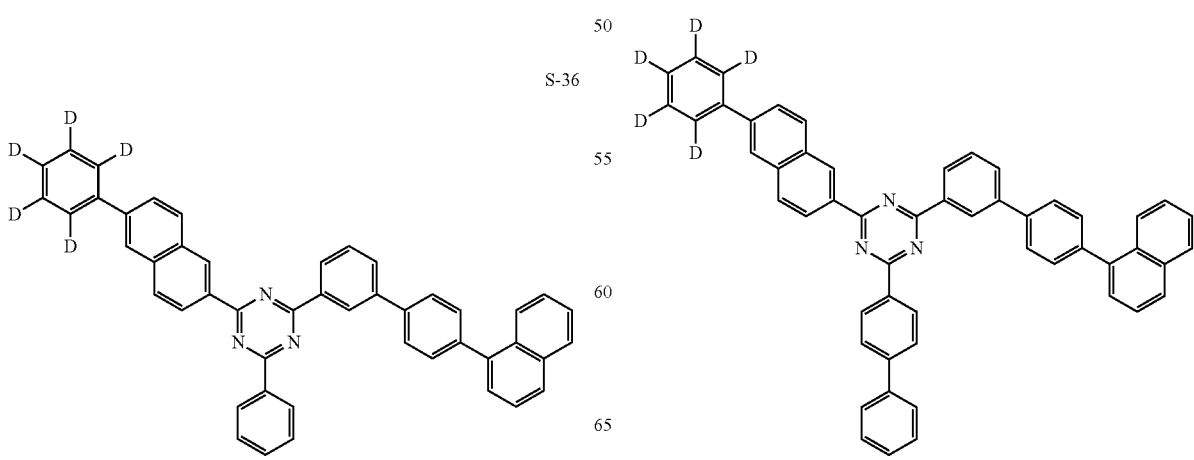
S-38
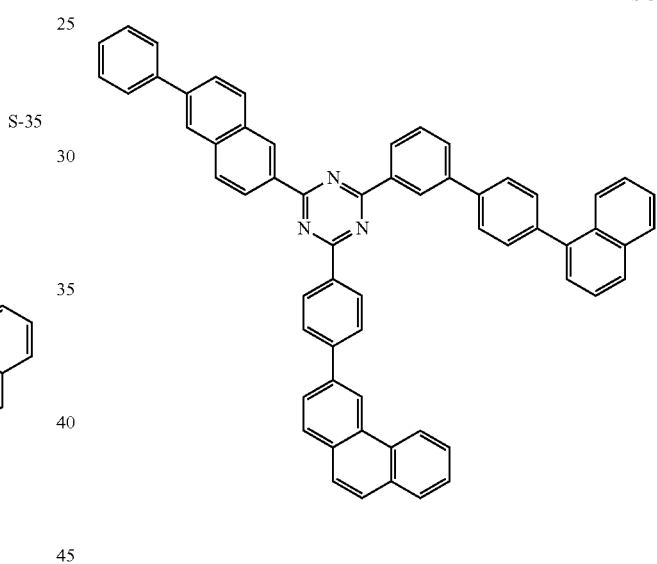
S-36
S-39

S-40
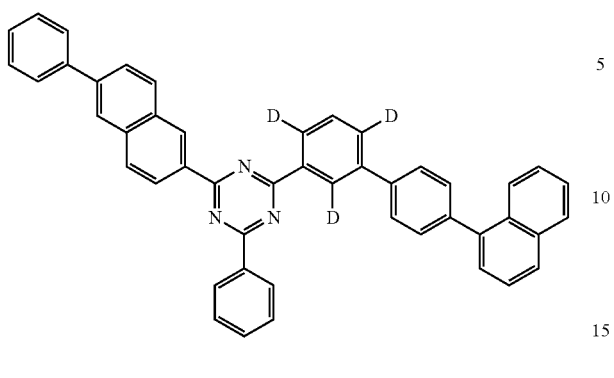
S-41
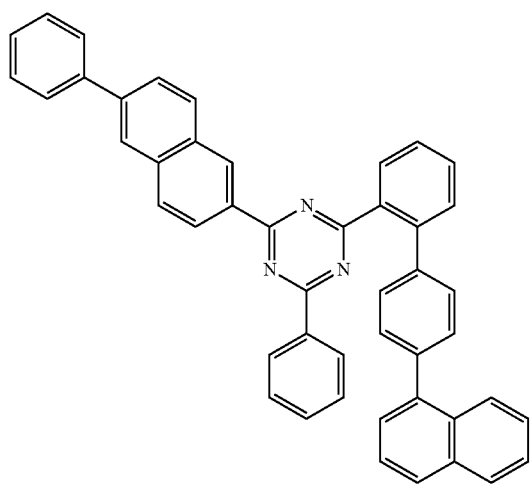
S-42
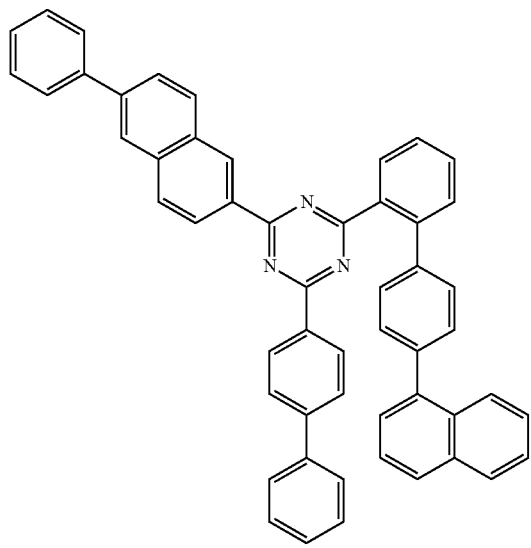
S-43
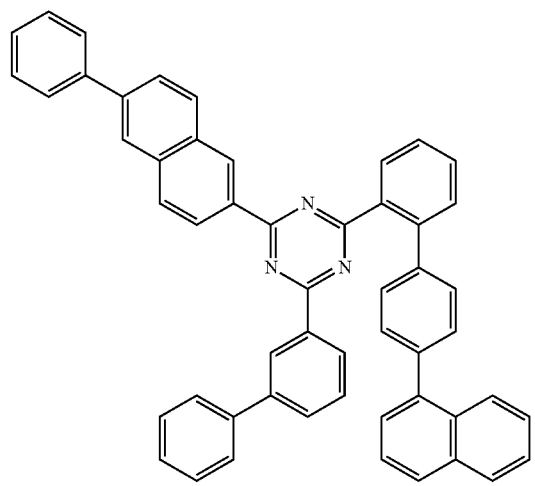
S-44
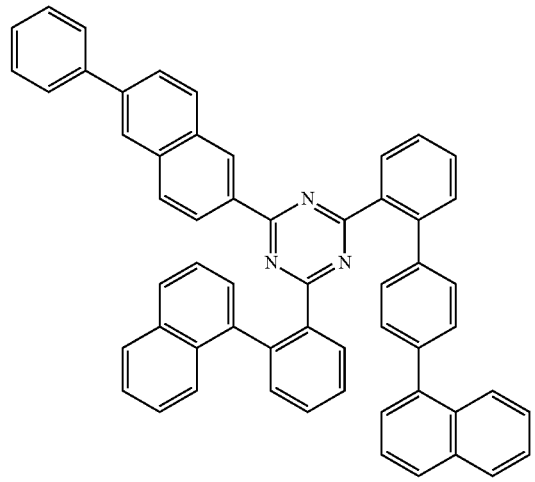
S-45
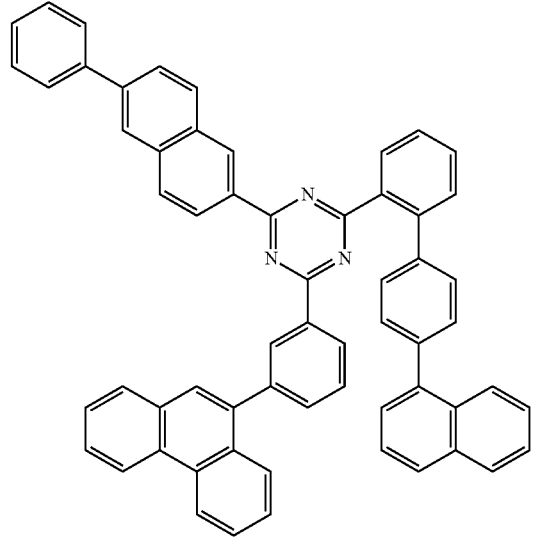

S-46
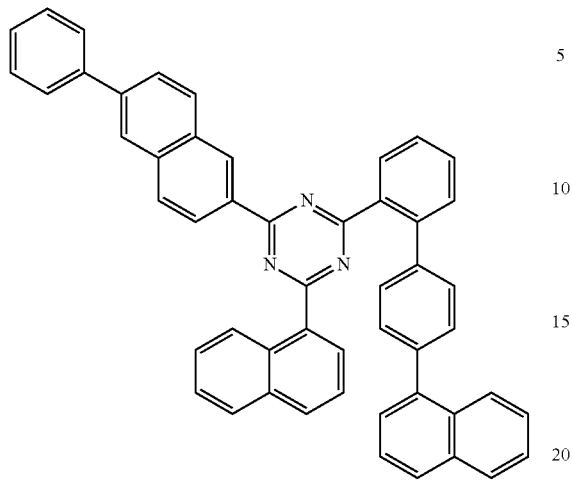
S-47
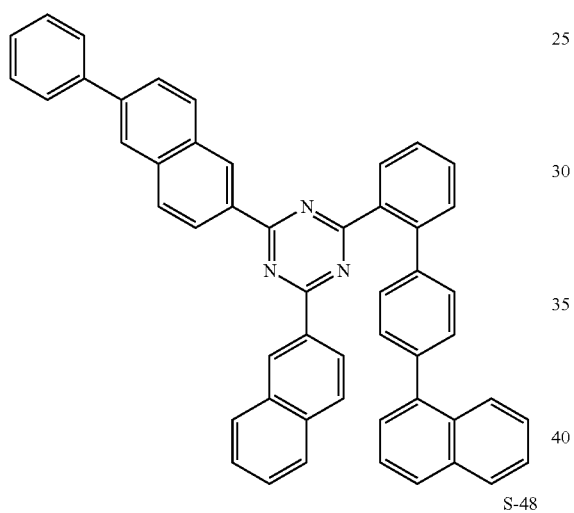
S-48
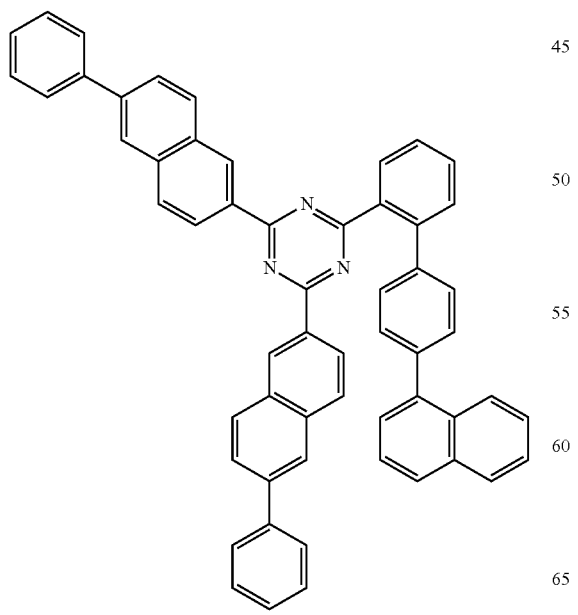
S-49
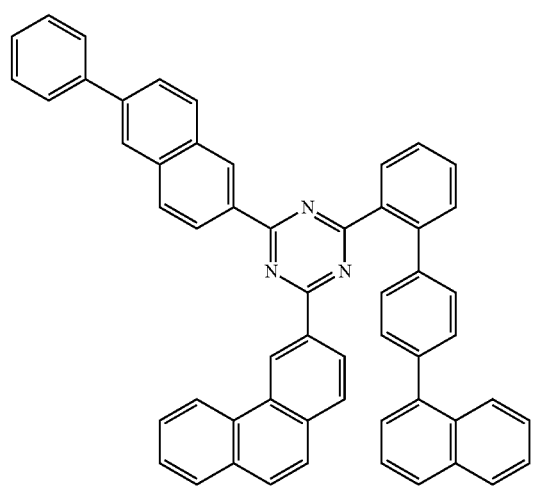
S-50
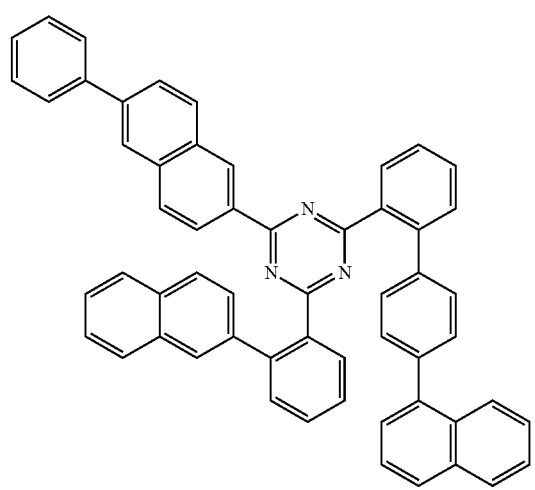
S-51
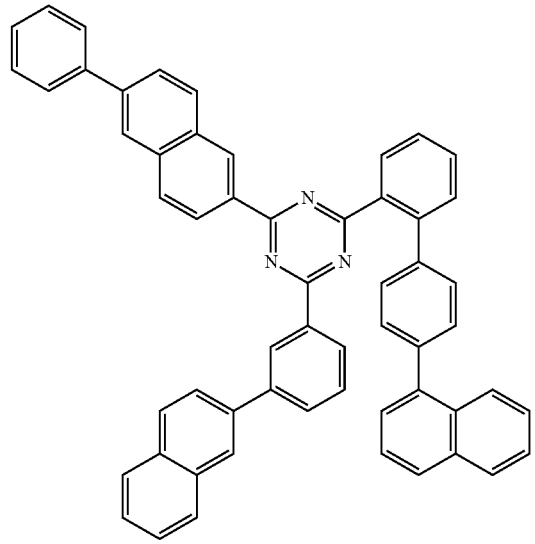

S-52

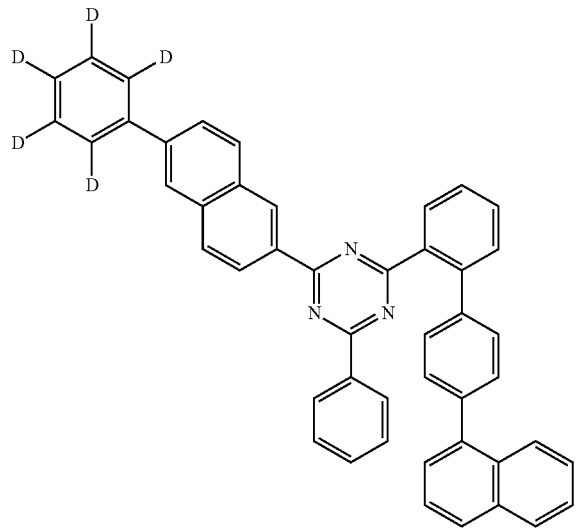

S-53

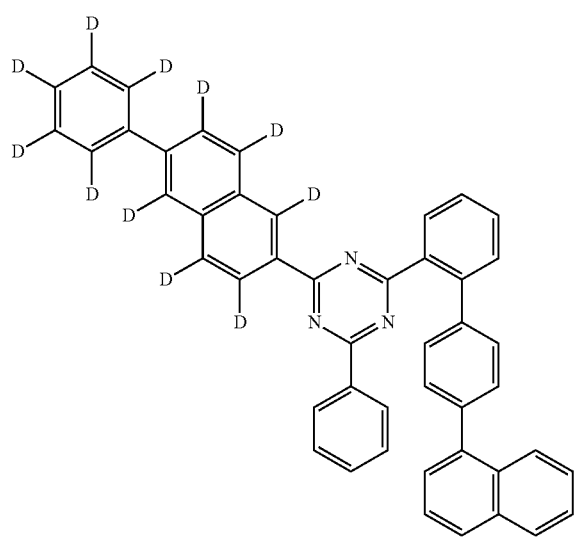

S-54

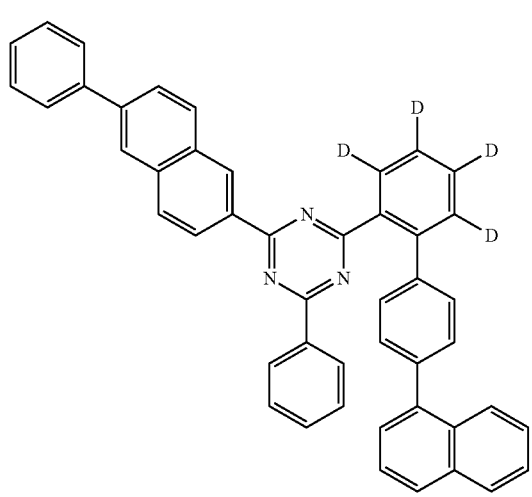

S-55

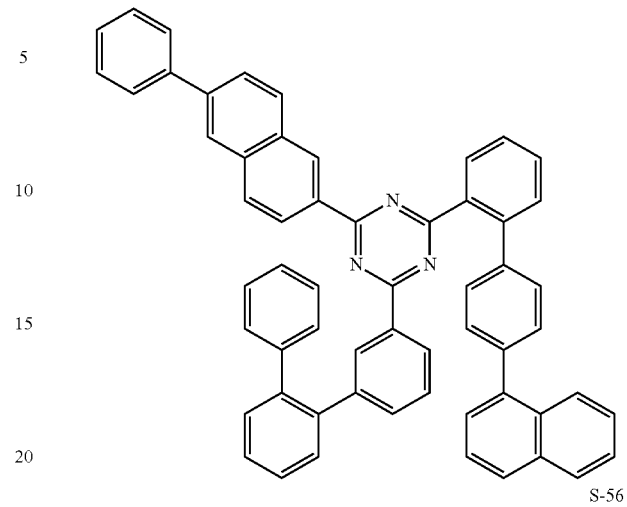

S-56

Referring to FIG. 1, the organic electronic element (100) according to the present invention includes a first electrode (110), a second electrode (170), and an organic material layer including a single compound or 2 or more compounds represented by Formula (2) between the first electrode (110) and the second electrode (170). In this case, the first electrode (110) may be an anode, and the second electrode (170) may be a cathode. In the case of an inverted type, the first electrode may be a cathode and the second electrode may be an anode.

Figure 2:
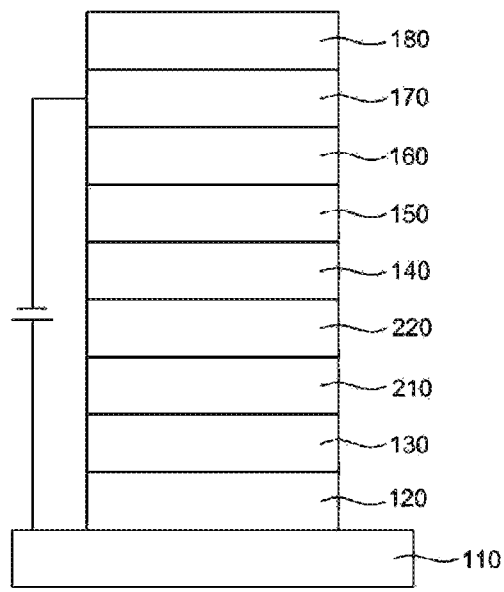

The organic material layer may sequentially include a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting auxiliary layer (220), a buffer layer (210), etc. and the electron transport layer (150) and the like may serve as a hole blocking layer. (See FIG. 2)

Also, the organic electronic element according to an embodiment of the present invention may further include a protective layer or a light efficiency enhancing layer (180). The light efficiency enhancing layer may be formed on one of both surfaces of the first electrode not in contact with the organic material layer or on one of both surfaces of the second electrode not in contact with the organic material layer. The compound according to an embodiment of the present invention applied to the organic material layer may be used as a host or dopant of the hole injection layer (120), the hole transport layer (130), the emitting auxiliary layer (220), electron transport auxiliary layer, the electron transport layer (150), and an electron injection layer (160), the emitting layer (140) or as a material for the light efficiency enhancing layer. Preferably, for example, the compound according to Formula (2) of the present invention may be used as a host material of the emitting layer, a hole blocking layer or an electron transport layer.

Figure 3:
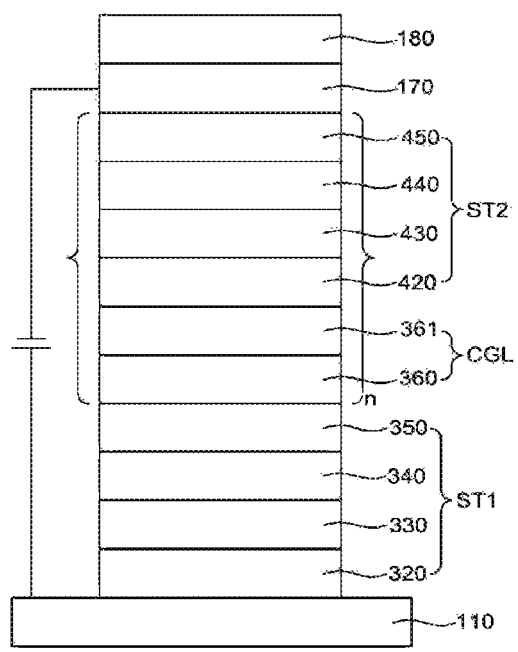

The organic material layer may include 2 or more stacks including a hole transport layer, an emitting layer and an electron transport layer sequentially formed on the anode, further include a charge generation layer formed between the 2 or more stacks (see FIG. 3).

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electroluminescent device according to an embodiment of the present invention may be manufactured using a PVD (physical vapor deposition) method. For example, depositing a metal or a metal oxide having conductivity or an alloy thereof on a substrate to form an anode, and after forming an organic material layer including the hole injection layer (120), the hole transport layer (130), the emitting layer (140), the electron transport layer (150) and the electron injection layer (160) thereon, it can be prepared by depositing a material that can be used as a cathode thereon.

Also, in the present invention, the organic material layer is formed by any one of a spin coating process, a nozzle printing process, an inkjet printing process, a slot coating process, a dip coating process, and a roll-to-roll process, and the organic material layer provides an organic electric element comprising the compound as an electron transport material.

As another specific example, the same or different compounds of the compound represented by Formula (2) are mixed and used in the organic material layer.

Also, the present invention provides an emitting layer composition comprising the compound represented by Formula (2), and provides an organic electronic element comprising the emitting layer.

Also, the present invention provides a hole blocking layer composition comprising the compound represented by Formula (2), and provides an organic electronic element comprising the hole blocking layer.

Also, the present invention provides an electron transport layer composition comprising the compound represented by Formula (2), and provides an organic electronic element comprising the electron transport layer.

Also, the present invention provides an electronic device comprising a display device including the organic electronic element; and a control unit for driving the display device;

In another aspect, the organic electronic element is at least one of an organic electroluminescent device, an organic solar cell, an organic photoreceptor, an organic transistor, and a device for monochromatic or white lighting. At this time, the electronic device may be a current or future wired/wireless communication terminal, and covers all kinds of electronic devices including mobile communication terminals such as mobile phones, a personal digital assistant (PDA), an electronic dictionary, a point-to-multipoint (PMP), a remote controller, a navigation unit, a game player, various kinds of TVs, and various kinds of computers.

Hereinafter, a synthesis example of the compound represented by Formula (2) of the present invention and a manufacturing example of an organic electronic element of the present invention will be described in detail with reference to Examples, but the present invention is not limited to the following Examples.

Synthesis Example

The compound (final products 1) represented by Formula 2 according to the present invention is synthesized by reacting Sub 3 and Sub 4 as shown in Scheme 1 below, but is not limited thereto.

<Reaction Scheme 1>

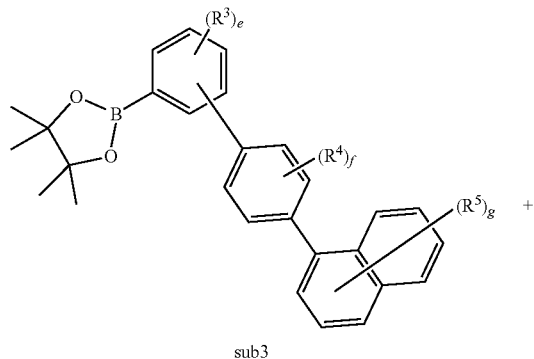

sub3

-continued
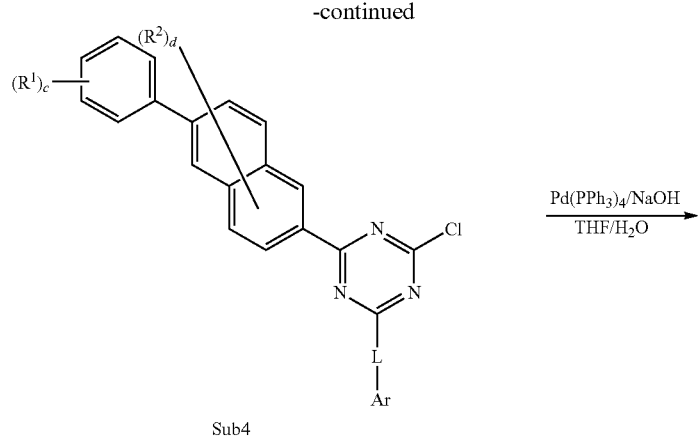
Sub4
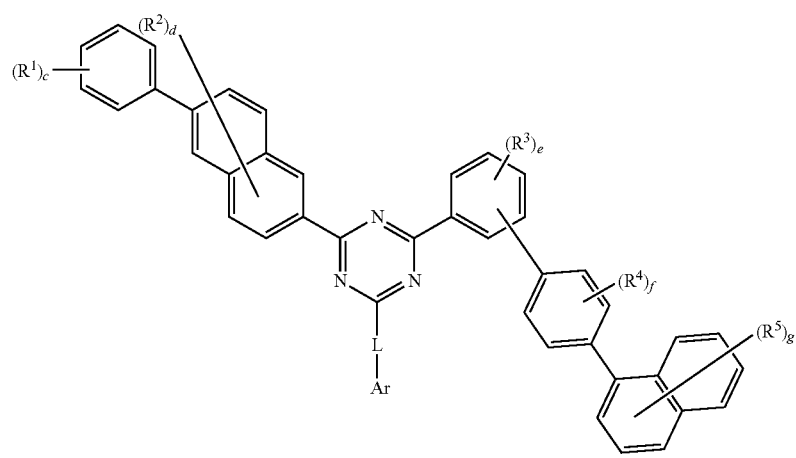
Final Products 1

I. Synthesis of Sub 3

Sub 3 of Scheme 1 is synthesized by the reaction route of Scheme 2 below, but is not limited thereto.

<Reaction Scheme 2>

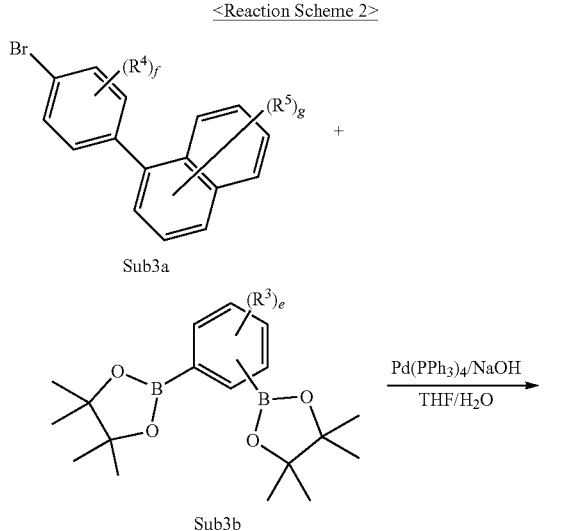

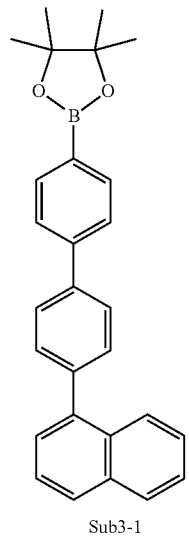

After dissolving Sub3a-1 (25.0 g, 88.3 mmol) in THF (Tetrahydrofuran) (440 mL) in a round-bottom flask, Sub3b-1 (29.1 g, 88.3 mmol), NaOH (10.6 g, 264.9 mmol), Pd(PPh$_3$)$_4$ (6.12 g, 5.30 mmol), water (220 mL) were added, and the mixture was stirred at 80° C. When the reaction was completed, the mixture was extracted with CH$_2$Cl$_2$ and water, and the organic layer was dried over MgSO$_4$ and concentrated. Thereafter, the resulting compound was recrystallized after applying a silica gel column to obtain 31.6 g (yield 88.2%) of the product.

2. Synthesis Example of Sub3-2

1. Synthesis Example of Sub3-1

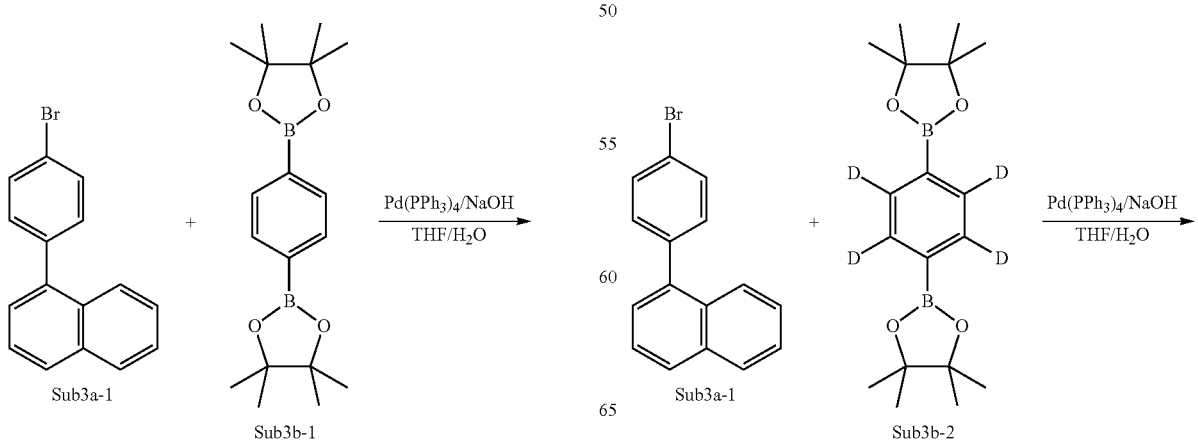

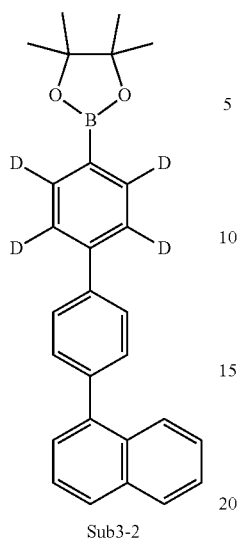

Sub3-2

After dissolving Sub3a-1 (10.0 g, 35.3 mmol) in THF (180 mL) in a round-bottom flask, Sub3b-2 (11.8 g, 35.3 mmol), NaOH (4.2 g, 105.9 mmol), Pd(PPh$_3$)$_4$ (2.45 g, 2.12 mmol), Water (90 mL) were added, and 12.5 g (yield 86.5%) of the product was obtained by using the method for synthesizing Sub3-1.

Sub3-4

After dissolving Sub3a-1 (25.0 g, 88.3 mmol) in THF (440 mL) in a round-bottom flask, Sub3b-4 (29.1 g, 88.3 mmol), NaOH (10.6 g, 264.9 mmol), Pd(PPh$_3$)$_4$ (6.12 g, 5.30 mmol), water (220 mL) were added, and 30.4 g (yield 84.8%) of the product was obtained by using the method for synthesizing Sub3-1.

3. Synthesis Example of Sub3-4

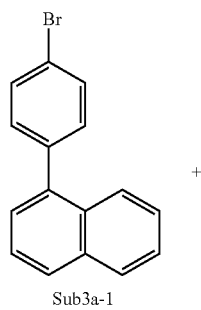

Sub3a-1

4. Synthesis Example of Sub3-6

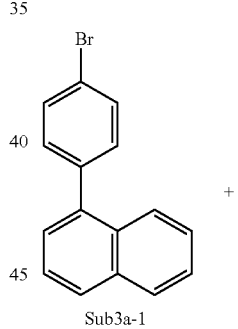

Sub3a-1

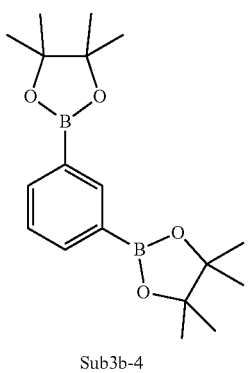

Sub3b-4

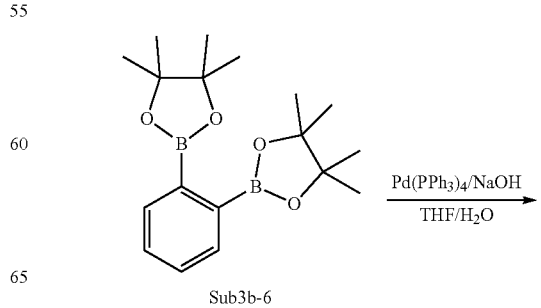

Sub3b-6

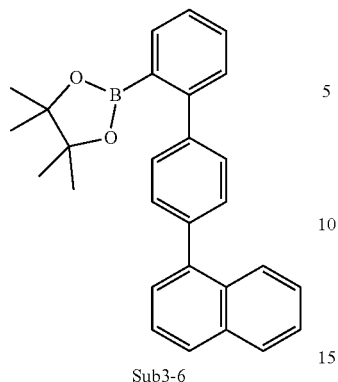

Sub3-6

After dissolving Sub3a-1 (25.0 g, 88.3 mmol) in THF (440 mL) in a round-bottom flask, Sub3b-6 (29.1 g, 88.3 mmol), NaOH (10.6 g, 264.9 mmol), Pd(PPh$_3$)$_4$ (6.12 g, 5.30 mmol), water (220 mL) were added, and 27.0 g (yield 75.3%) of the product was obtained by using the method for synthesizing Sub3-1.

The compound belonging to Sub3 may be the following compounds, but is not limited thereto, and Table 1 below shows Field Desorption-Mass Spectrometry (FD-MS) values of the compounds belonging to Sub3.

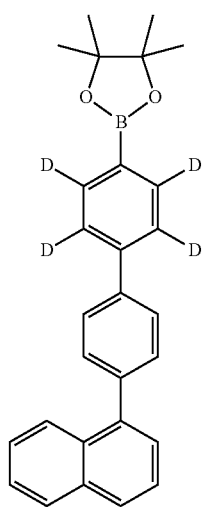

Sub3-2

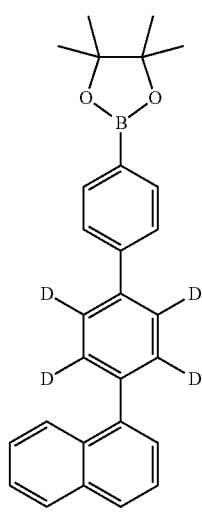

Sub3-3

Sub3-1

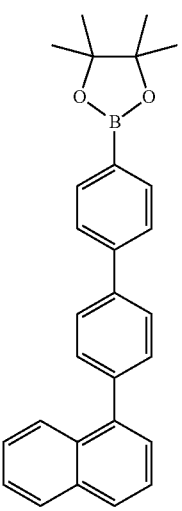

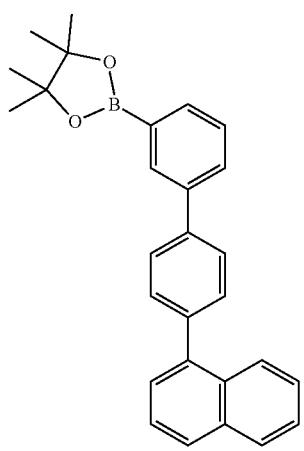

Sub3-4

41
-continued

Sub3-5

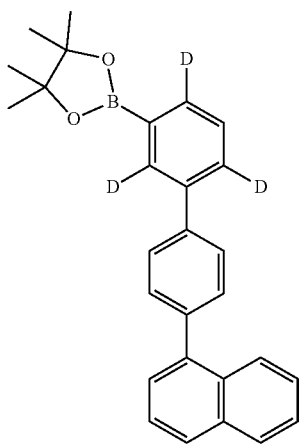

Sub3-6

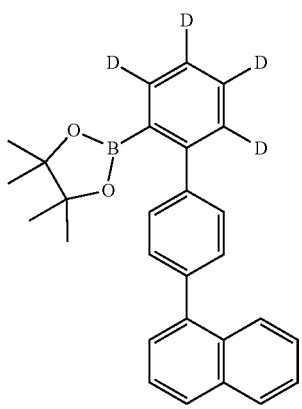

Sub3-7

42

II. Synthesis of Sub4

Sub4 of Scheme 1 is synthesized by the reaction route of Reaction Scheme 3 below, but is not limited thereto.

<Reaction Scheme 3>

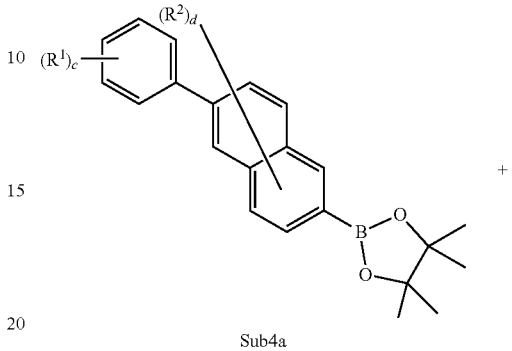

Sub4a

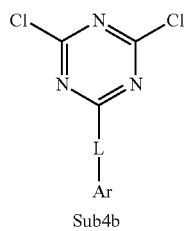

Sub4b

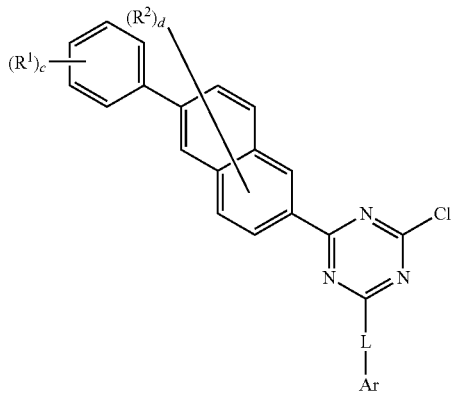

Sub4

TABLE 1

| compound | FD-MS | compound | FD-MS |
|---|---|---|---|
| Sub3-1 | m/z = 406.21(C$_{28}$H$_{27}$BO$_2$ = 406.33) | Sub3-2 | m/z = 410.24(C$_{28}$H$_{23}$D$_4$BO$_2$ = 410.36) |
| Sub3-3 | m/z = 410.24(C$_{28}$H$_{23}$D$_4$BO$_2$ = 410.36) | Sub3-4 | m/z = 406.21(C$_{28}$H$_{27}$BO$_2$ = 406.33) |
| Sub3-5 | m/z = 409.23(C$_{28}$H$_{24}$D$_3$BO$_2$ = 409.35) | Sub3-6 | m/z = 406.21(C$_{28}$H$_{27}$BO$_2$ = 406.33) |
| Sub3-7 | m/z = 410.24(C$_{28}$H$_{23}$D$_4$BO$_2$ = 410.36) | | |

1. Synthesis Example of Sub4-1

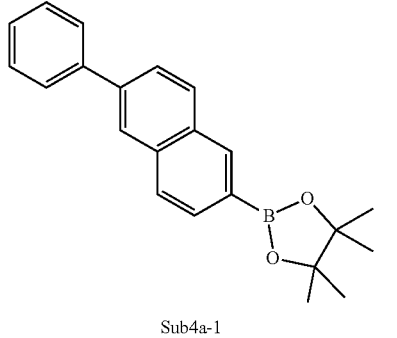

Sub4a-1

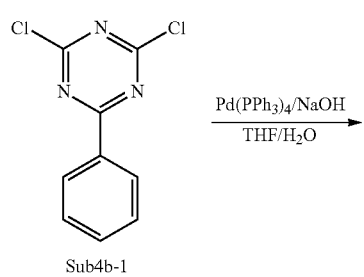

Sub4b-1

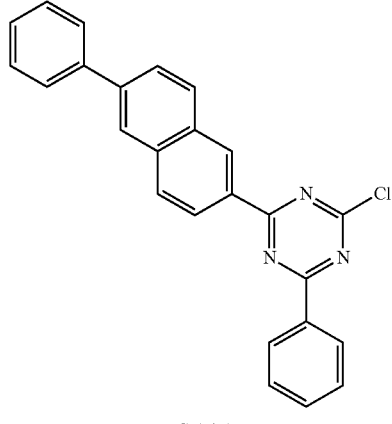

Sub4-1

After dissolving Sub4b-1 (17.1 g, 75.7 mmol) in THF (Tetrahydrofuran) (380 mL) in a round-bottom flask, Sub4a-1 (25.0 g, 75.7 mmol), NaOH (9.1 g, 227.1 mmol), Pd(PPh$_3$)$_4$ (5.25 g, 4.54 mmol), water (190 mL) were added, and the mixture was stirred at 80° C. When the reaction was completed, the mixture was extracted with CH$_2$Cl$_2$ and water, and the organic layer was dried over MgSO$_4$ and concentrated.

Thereafter, the resulting compound was recrystallized after applying a silica gel column to obtain 21.5 g (yield 72.1%) of the product.

2. Synthesis of Sub4-17

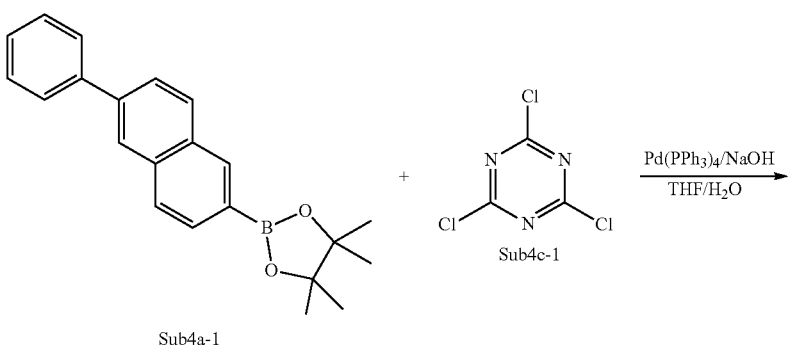

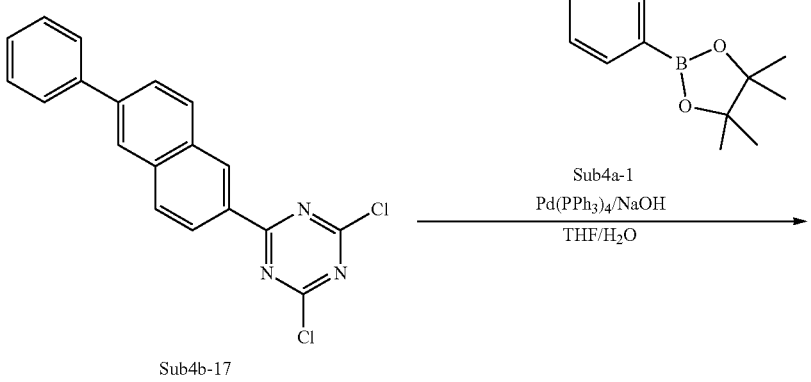

Sub4b-17

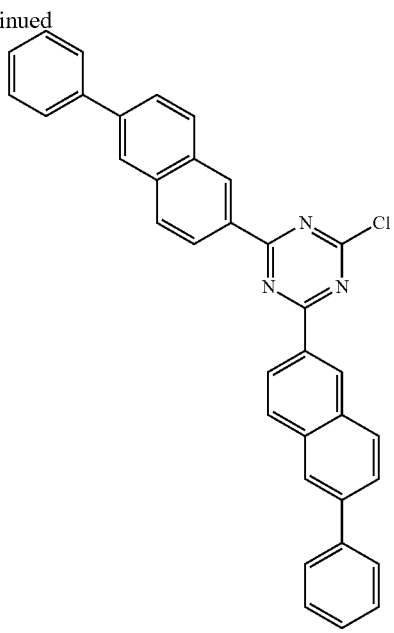

Sub4-17

(1) Synthesis Example of Sub4b-17

After dissolving Sub4c-1 (8.4 g, 45.4 mmol) in THF (230 mL) in a round-bottom flask, Sub4a-1 (15.0 g, 45.4 mmol), NaOH (5.5 g, 136.3 mmol), Pd(PPh$_3$)$_4$ (3.15 g, 2.73 mmol), water (115 mL) were added and 10.2 g (yield 63.7%) of the product was obtained by using the method for synthesizing Sub4-1.

(2) Synthesis Example of Sub4-17

After dissolving Sub4b-17 (10.2 g, 28.9 mmol) in THF (145 mL) in a round-bottom flask, Sub4a-1 (9.6 g, 28.9 mmol), NaOH (3.5 g, 86.8 mmol), Pd(PPh$_3$)$_4$ (2.01 g, 1.74 mmol), water (72 mL) were added, and 10.7 g (yield 71.0%) of the product was obtained by using the method for synthesizing Sub4-1.

3. Synthesis of Sub4-20

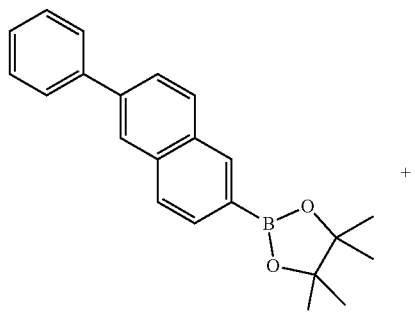

Sub4a-1

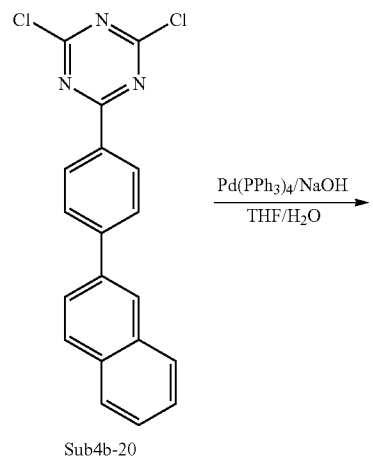

Sub4b-20

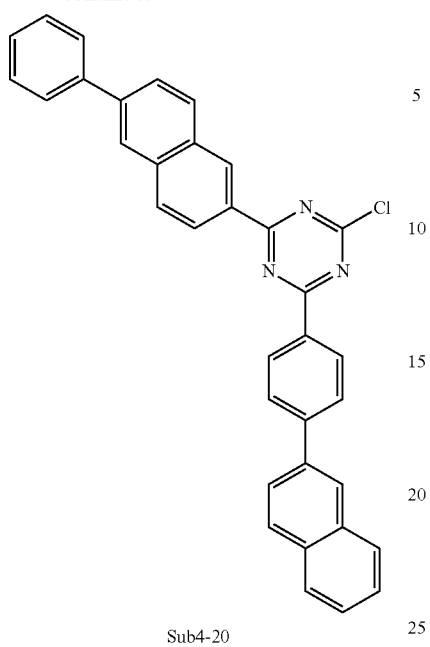

Sub4-20

After dissolving Sub4b-20 (16.0 g, 45.4 mmol) in THF (230 mL) in a round-bottom flask, Sub4a-1 (15.0 g, 45.4 mmol), NaOH (5.5 g, 136.3 mmol), Pd(PPh$_3$)$_4$ (3.15 g, 2.73 mmol), water (115 mL) were added and 17.1 g (yield 72.6%) of the product was obtained by using the method for synthesizing Sub4-1.

4. Synthesis of Sub4-31

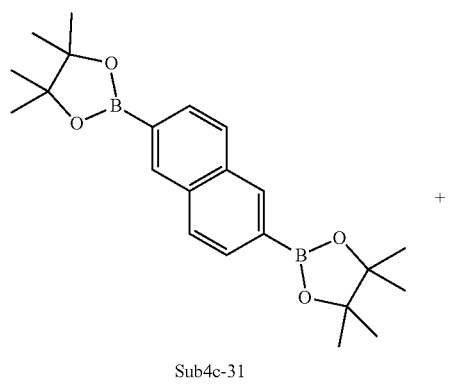

Sub4c-31

+

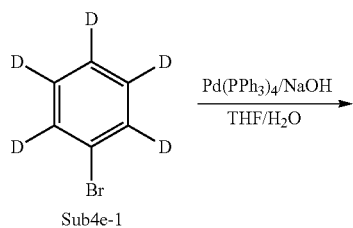

Sub4e-1

Pd(PPh$_3$)$_4$/NaOH
THF/H$_2$O
⟶

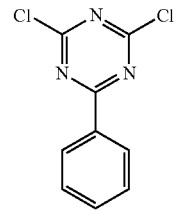

Pd(PPh$_3$)$_4$/NaOH
⟶

Sub4a-31

Sub4-31

(1) Synthesis Example of Sub4a-31

After dissolving Sub4e-31 (10.7 g, 65.8 mmol) in THF (330 mL) in a round-bottom flask, Sub4c-31 (25.0 g, 65.8 mmol), NaOH (7.9 g, 197.3 mmol), Pd(PPh$_3$)$_4$ (4.56 g, 3.95 mmol), water (165 mL) were added, and 17.9 g (yield 81.1%) of the product was obtained using the method for synthesizing Sub4-1.

(2) Synthesis Example of Sub4-31

After dissolving Sub4b-1 (12.1 g, 53.3 mmol) in THF (270 mL) in a round-bottom flask, Sub4a-31 (17.9 g, 53.3 mmol), NaOH (6.4 g, 160.0 mmol), Pd(PPh$_3$)$_4$ (3.70 g, 3.20 mmol), water (135 mL) were added and 15.8 g (yield 74.4%) of the product was obtained by using the method for synthesizing Sub4-1.

5. Synthesis of Sub4-35

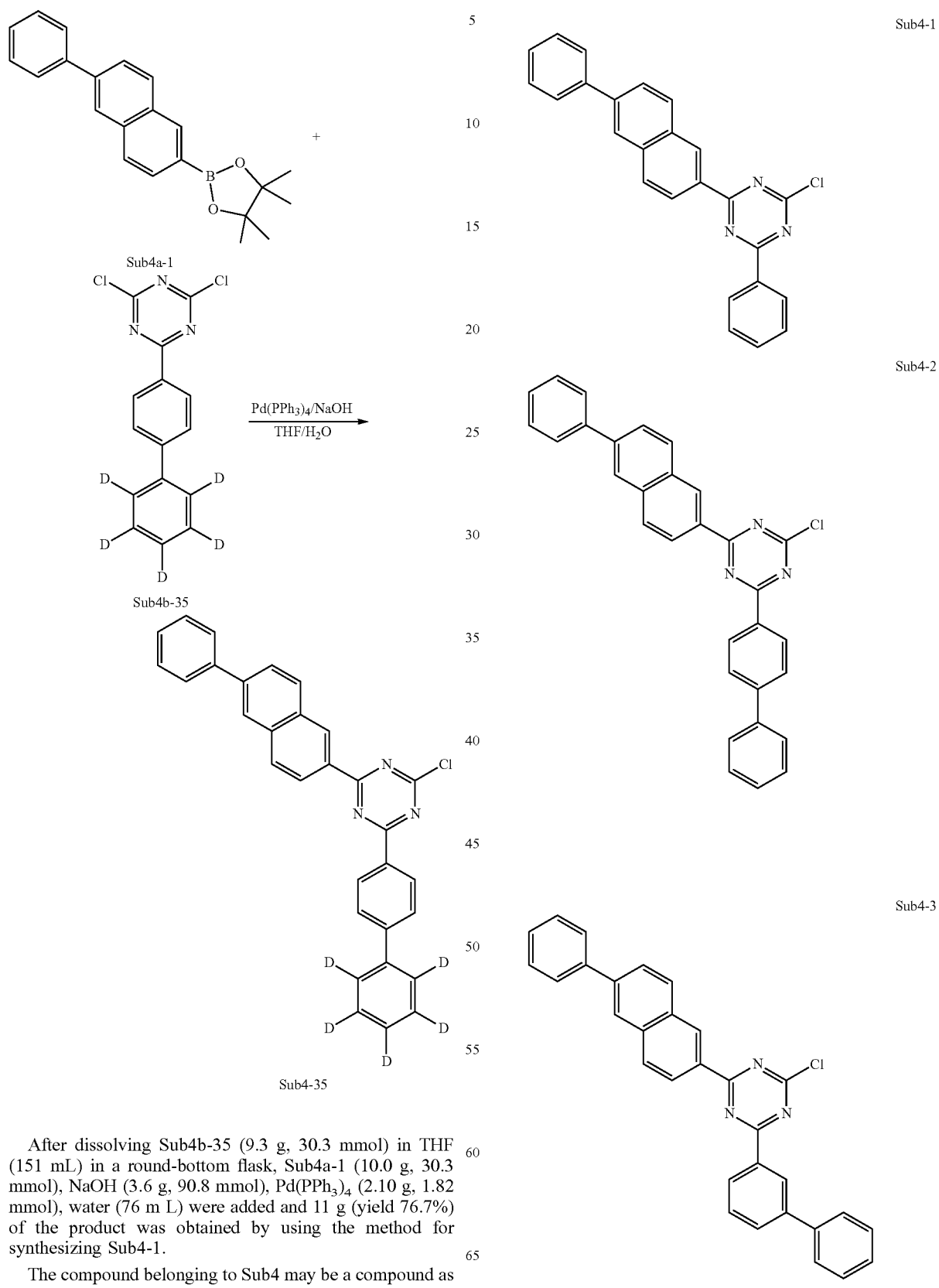

After dissolving Sub4b-35 (9.3 g, 30.3 mmol) in THF (151 mL) in a round-bottom flask, Sub4a-1 (10.0 g, 30.3 mmol), NaOH (3.6 g, 90.8 mmol), Pd(PPh$_3$)$_4$ (2.10 g, 1.82 mmol), water (76 m L) were added and 11 g (yield 76.7%) of the product was obtained by using the method for synthesizing Sub4-1.

The compound belonging to Sub4 may be a compound as follows, but is not limited thereto, and Table 2 below shows Field Desorption-Mass Spectrometry (FD-MS) values of the compound belonging to Sub4.

-continued
Sub4-4
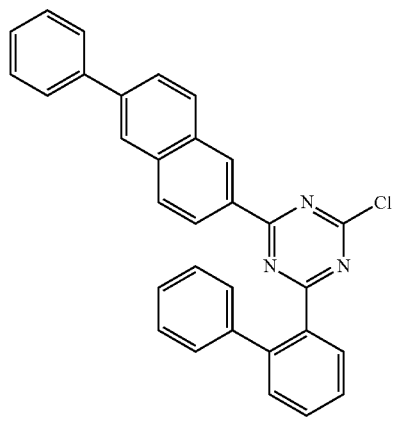
Sub4-7
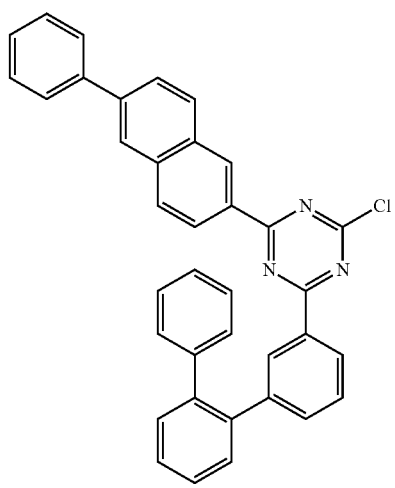
Sub4-5
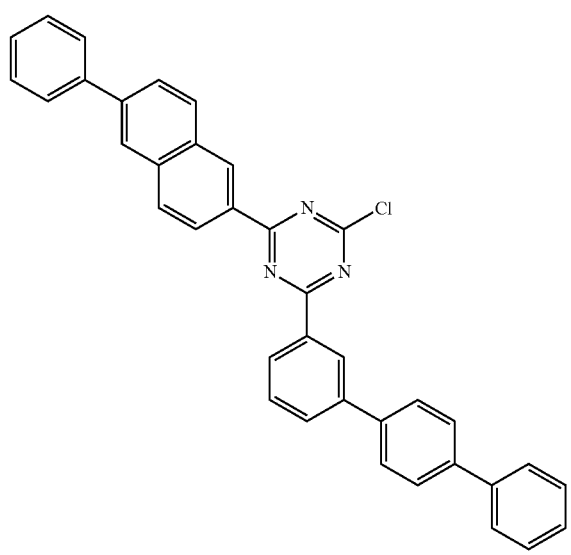
Sub4-8
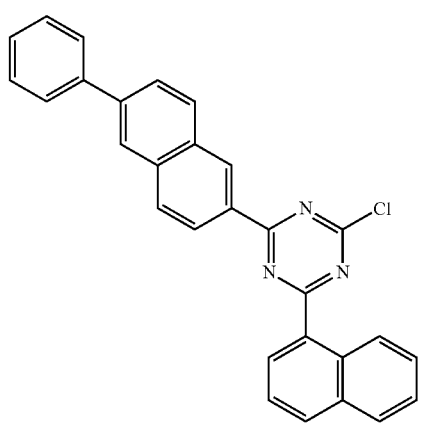
Sub4-6
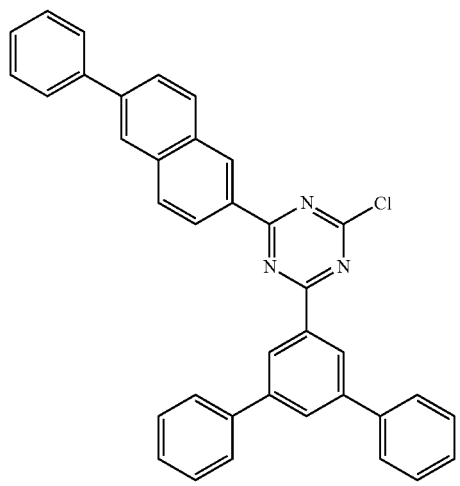
Sub4-9

Sub4-10
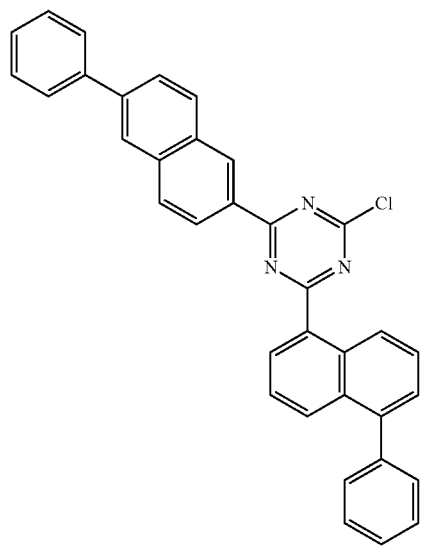
Sub4-11
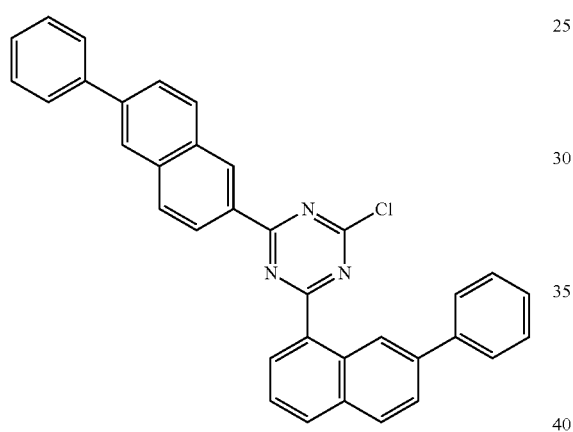
Sub4-12
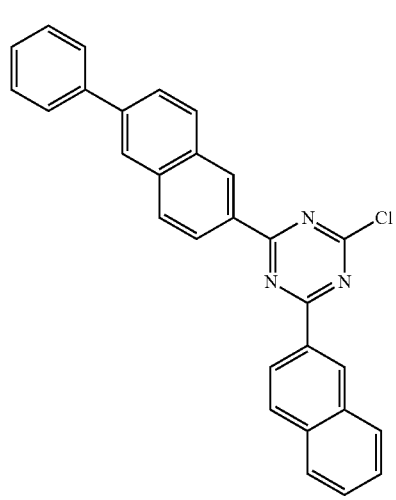
Sub4-13
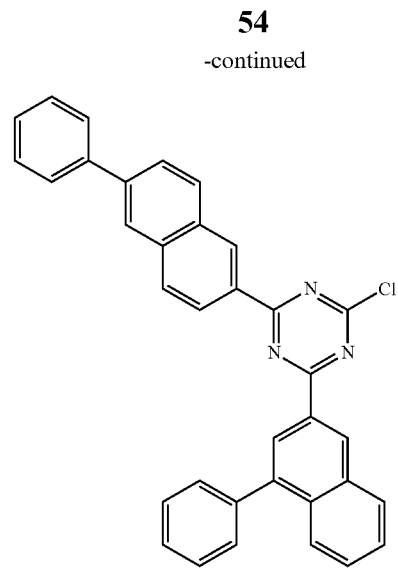
Sub4-14
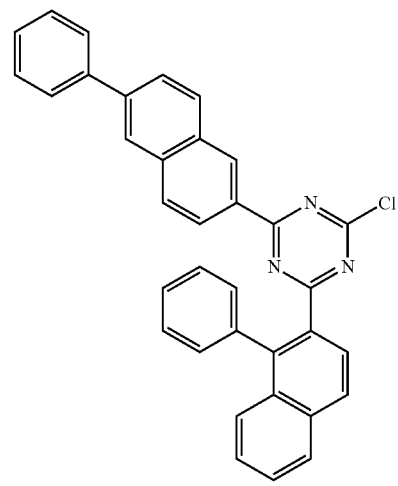
Sub4-15
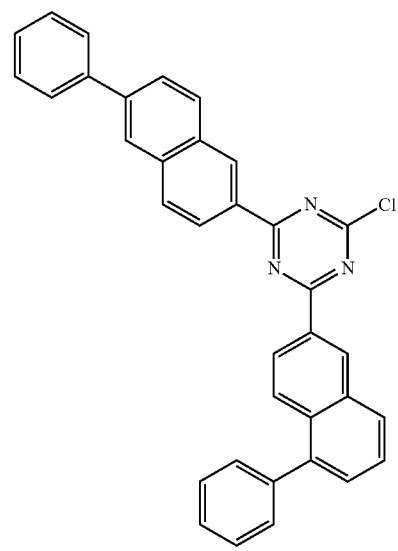

-continued
Sub4-16
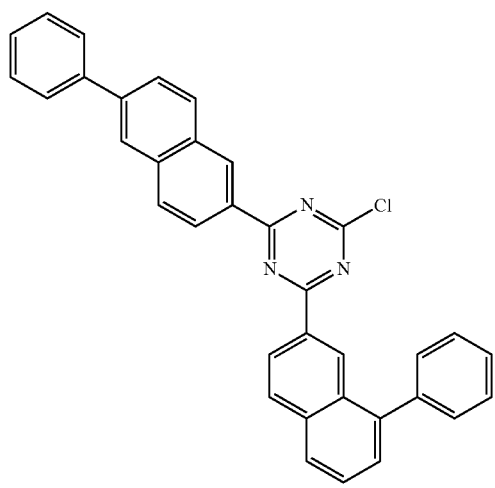
Sub4-17
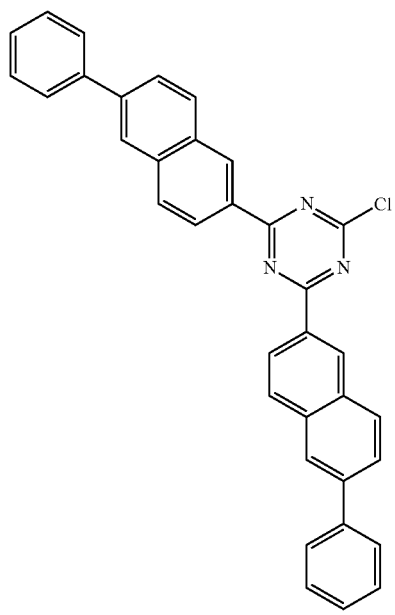
Sub4-18
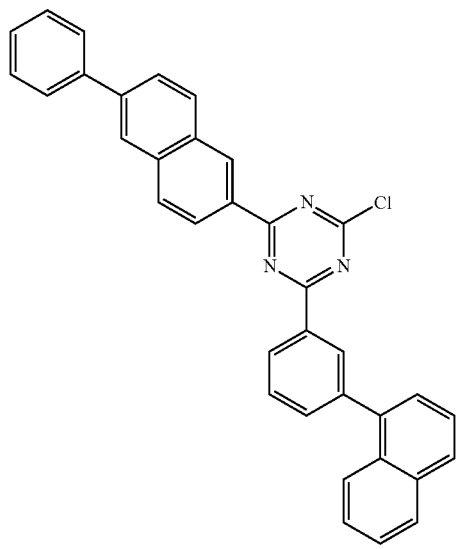
Sub4-19
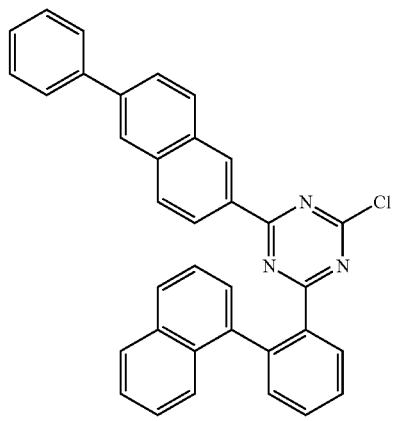
Sub4-20
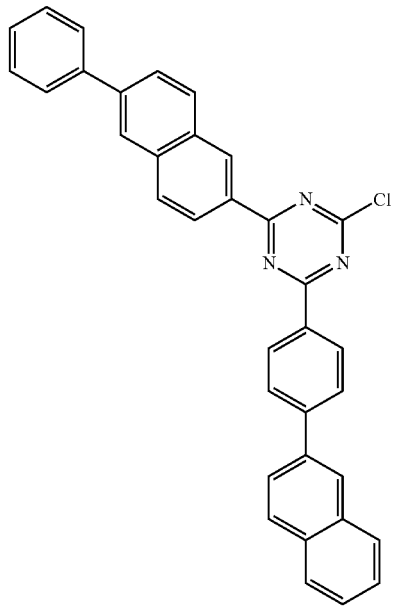
Sub4-21
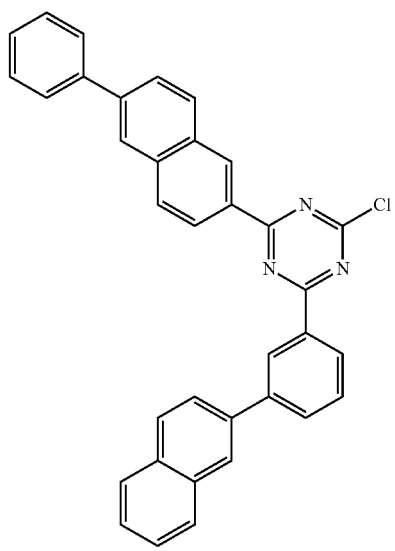

Sub4-22
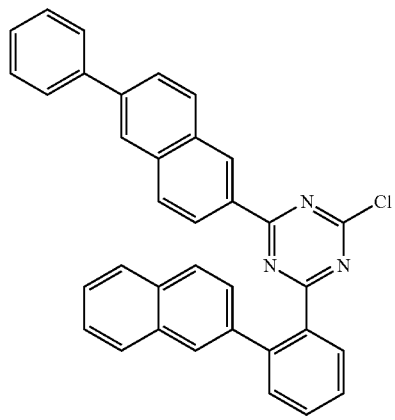
Sub4-23
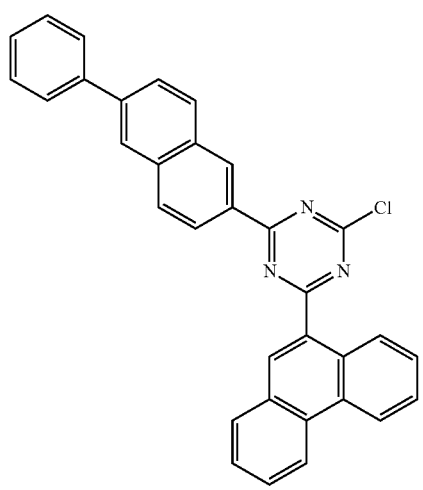
Sub4-24
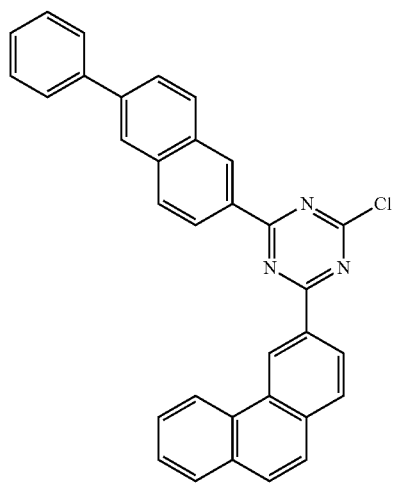
Sub4-25
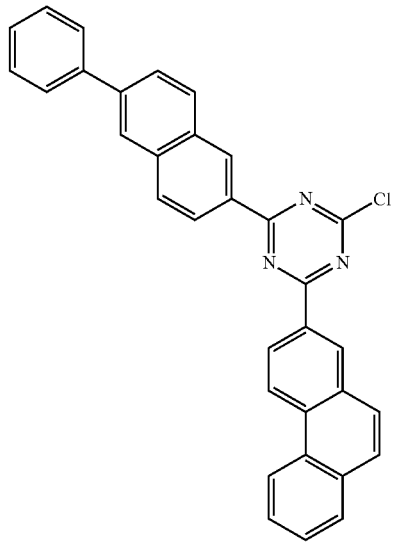
Sub4-26

Sub4-27
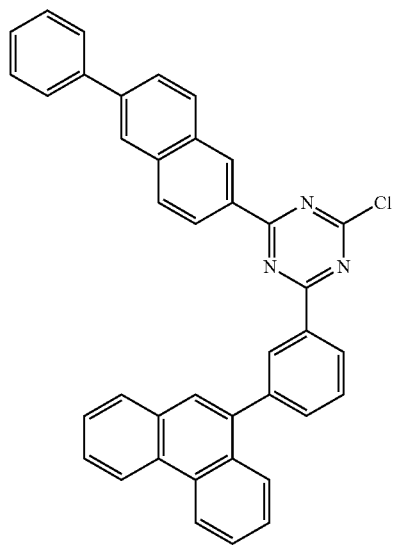
Sub4-28
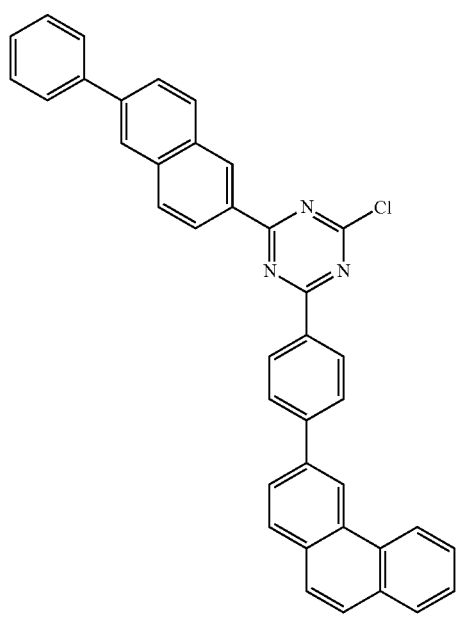
Sub4-29
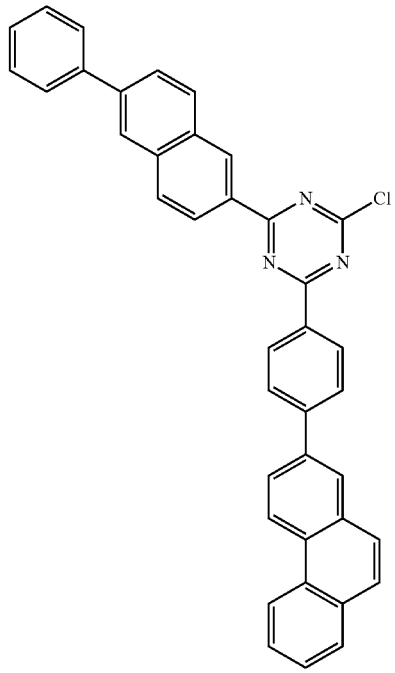
Sub4-30

Sub4-31
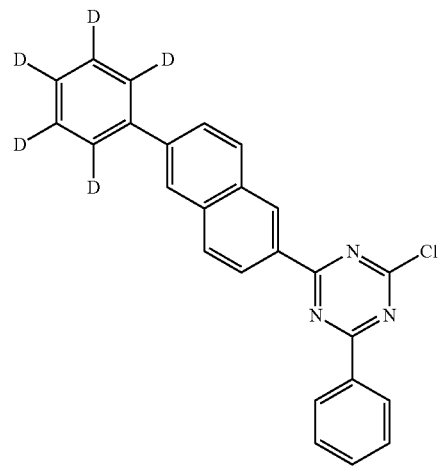
Sub4-32
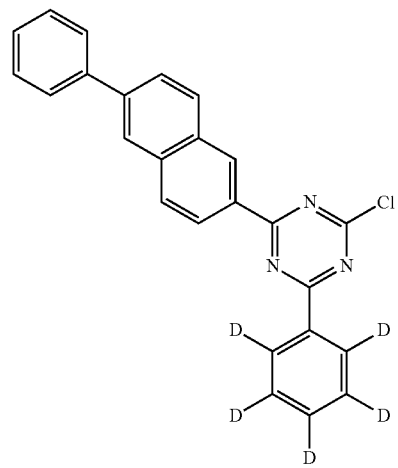
Sub4-33
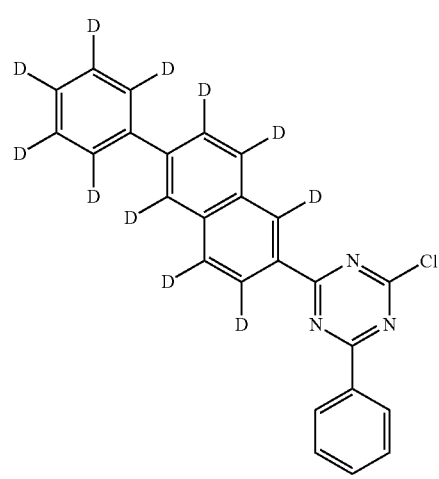
Sub4-34
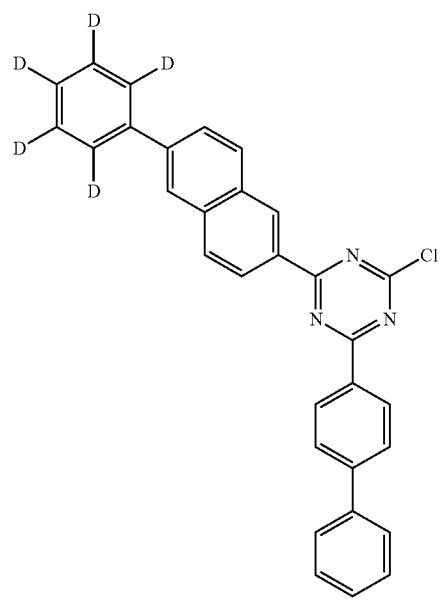
Sub4-35
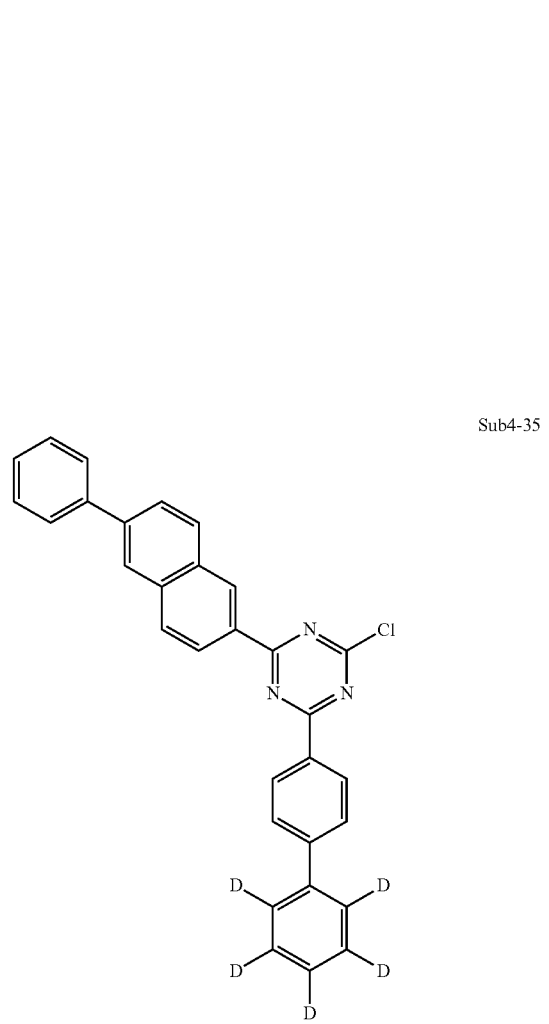

-continued

Sub4-36

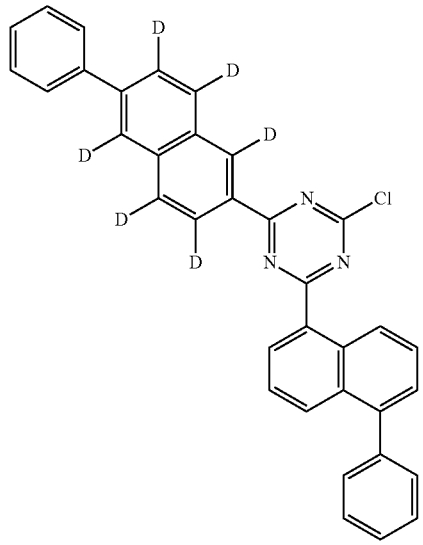

Sub4-37

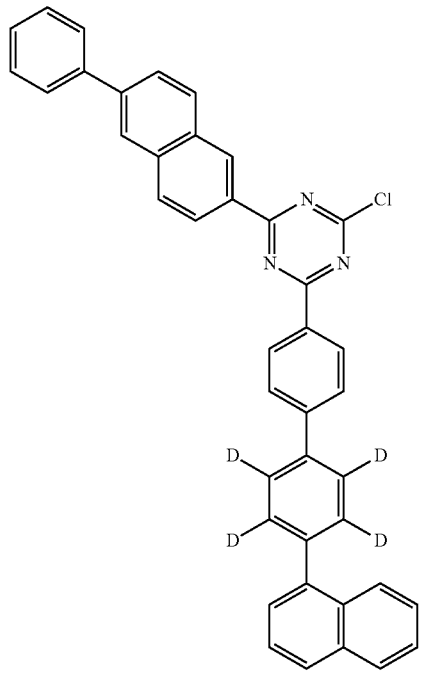

TABLE 2

| compound | FD-MS | compound | FD-MS |
| --- | --- | --- | --- |
| Sub4-1 | m/z = 393.1($C_{25}H_{16}ClN_3$ = 393.87) | Sub4-2 | m/z = 469.13($C_{31}H_{20}ClN_3$ = 469.97) |
| Sub4-3 | m/z = 469.13($C_{31}H_{20}ClN_3$ = 469.97) | Sub4-4 | m/z = 469.13($C_{31}H_{20}ClN_3$ = 469.97) |
| Sub4-5 | m/z = 545.17($C_{37}H_{24}ClN_3$ = 546.07) | Sub4-6 | m/z = 545.17($C_{37}H_{24}ClN_3$ = 546.07) |
| Sub4-7 | m/z = 545.17($C_{37}H_{24}ClN_3$ = 546.07) | Sub4-8 | m/z = 443.12($C_{29}H_{18}ClN_3$ = 443.93) |
| Sub4-9 | m/z = 519.15($C_{35}H_{22}ClN_3$ = 520.03) | Sub4-10 | m/z = 519.15($C_{35}H_{22}ClN_3$ = 520.03) |
| Sub4-11 | m/z = 519.15($C_{35}H_{22}ClN_3$ = 520.03) | Sub4-12 | m/z = 443.12($C_{29}H_{18}ClN_3$ = 443.93) |
| Sub4-13 | m/z = 519.15($C_{35}H_{22}ClN_3$ = 520.03) | Sub4-14 | m/z = 519.15($C_{35}H_{22}ClN_3$ = 520.03) |
| Sub4-15 | m/z = 519.15($C_{35}H_{22}ClN_3$ = 520.03) | Sub4-16 | m/z = 519.15($C_{35}H_{22}ClN_3$ = 520.03) |
| Sub4-17 | m/z = 519.15($C_{35}H_{22}ClN_3$ = 520.03) | Sub4-18 | m/z = 519.15($C_{35}H_{22}ClN_3$ = 520.03) |
| Sub4-19 | m/z = 519.15($C_{35}H_{22}ClN_3$ = 520.03) | Sub4-20 | m/z = 519.15($C_{35}H_{22}ClN_3$ = 520.03) |
| Sub4-21 | m/z = 519.15($C_{35}H_{22}ClN_3$ = 520.03) | Sub4-22 | m/z = 519.15($C_{35}H_{22}ClN_3$ = 520.03) |
| Sub4-23 | m/z = 493.13($C_{33}H_{20}ClN_3$ = 493.99) | Sub4-24 | m/z = 493.13($C_{33}H_{20}ClN_3$ = 493.99) |
| Sub4-25 | m/z = 493.13($C_{33}H_{20}ClN_3$ = 493.99) | Sub4-26 | m/z = 569.17($C_{39}H_{24}ClN_3$ = 570.09) |
| Sub4-27 | m/z = 569.17($C_{39}H_{24}ClN_3$ = 570.09) | Sub4-28 | m/z = 569.17($C_{39}H_{24}ClN_3$ = 570.09) |
| Sub4-29 | m/z = 569.17($C_{39}H_{24}ClN_3$ = 570.09) | Sub4-30 | m/z = 619.18($C_{43}H_{26}ClN_3$ = 620.15) |

TABLE 2-continued

| compound | FD-MS | compound | FD-MS |
|---|---|---|---|
| Sub4-31 | m/z = 398.13($C_{25}H_{11}D_5ClN_3$ = 398.9) | Sub4-32 | m/z = 398.13($C_{25}H_{11}D_5ClN_3$ = 398.9) |
| Sub4-33 | m/z = 404.17($C_{25}H_5D_{11}ClN_3$ = 404.94) | Sub4-34 | m/z = 474.17($C_{31}H_{15}D_5ClN_3$ = 475) |
| Sub4-35 | m/z = 474.17($C_{31}H_{15}D_5ClN_3$ = 475) | Sub4-36 | m/z = 525.19($C_{35}H_{16}D_6ClN_3$ = 526.07) |
| Sub4-37 | m/z = 599.21($C_{41}H_{22}D_4ClN_3$ = 600.15) | | |

III. Synthesis of Final Product 1

1. Synthesis Example of S-1

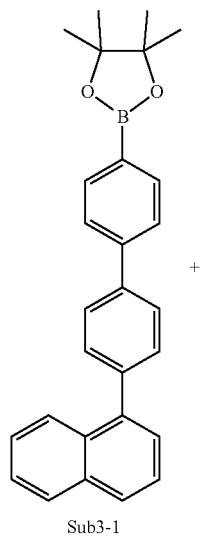

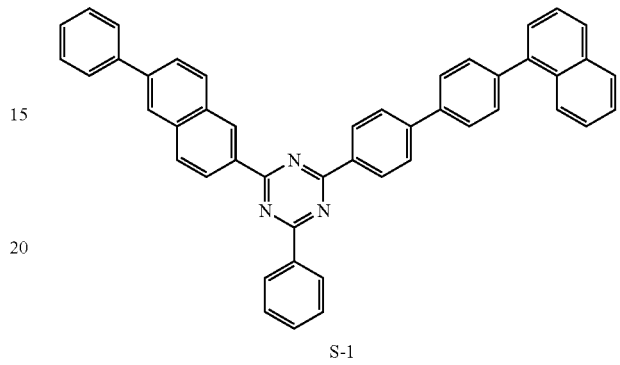

After dissolving Sub4-1 (2.9 g, 7.4 mmol) in THF (Tetrahydrofuran) (37 mL) in a round-bottom flask, Sub3-1 (3.0 g, 7.4 mmol), NaOH (0.9 g, 22.1 mmol), Pd(PPh$_3$)$_4$ (0.51 g, 0.44 mmol), water (18 mL) were added and stirred at 80° C.

When the reaction was completed, the mixture was extracted with CH$_2$Cl$_2$ and water, and the organic layer was dried over MgSO$_4$ and concentrated. Thereafter, the resulting compound was recrystallized after applying a silica gel column to obtain 3.7 g (yield 78%) of the product.

2. Synthesis Example of S-9

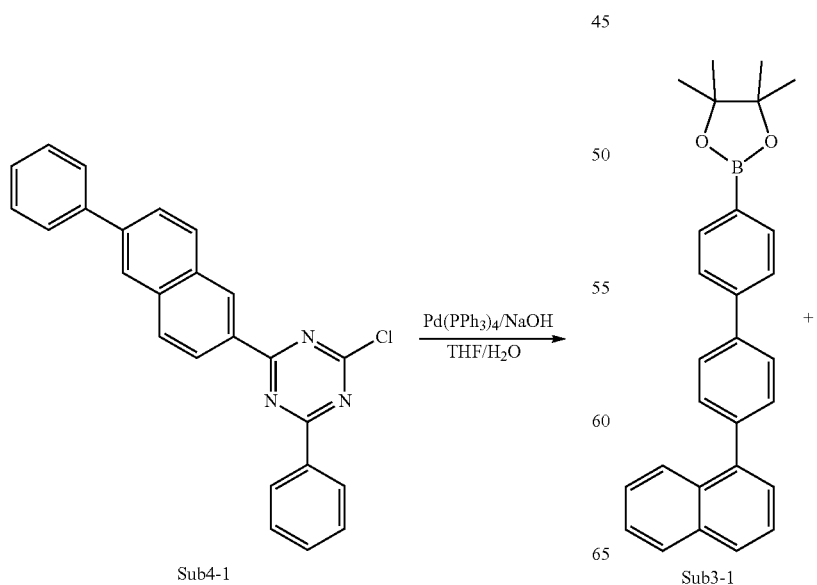

3. Synthesis Example of S-12
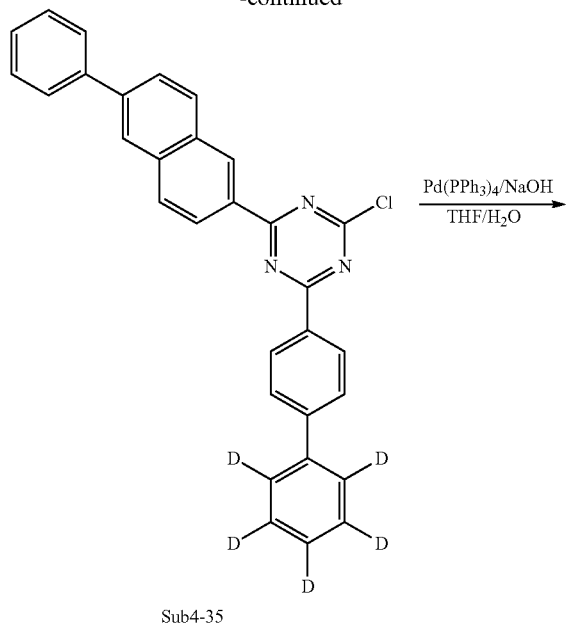
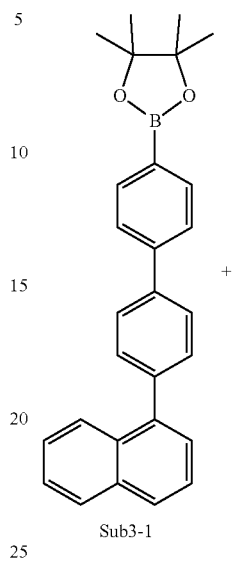
After dissolving Sub4-35 (3.5 g, 7.4 mmol) in THF (37 mL) in a round-bottom flask, Sub3-1 (3.0 g, 7.4 mmol), NaOH (0.9 g, 22.1 mmol), Pd(PPh$_3$)$_4$ (0.51 g, 0.44 mmol), water (18 mL) was added, and 4.0 g (yield 76%) of the product was obtained by using the synthesis method of S-1.
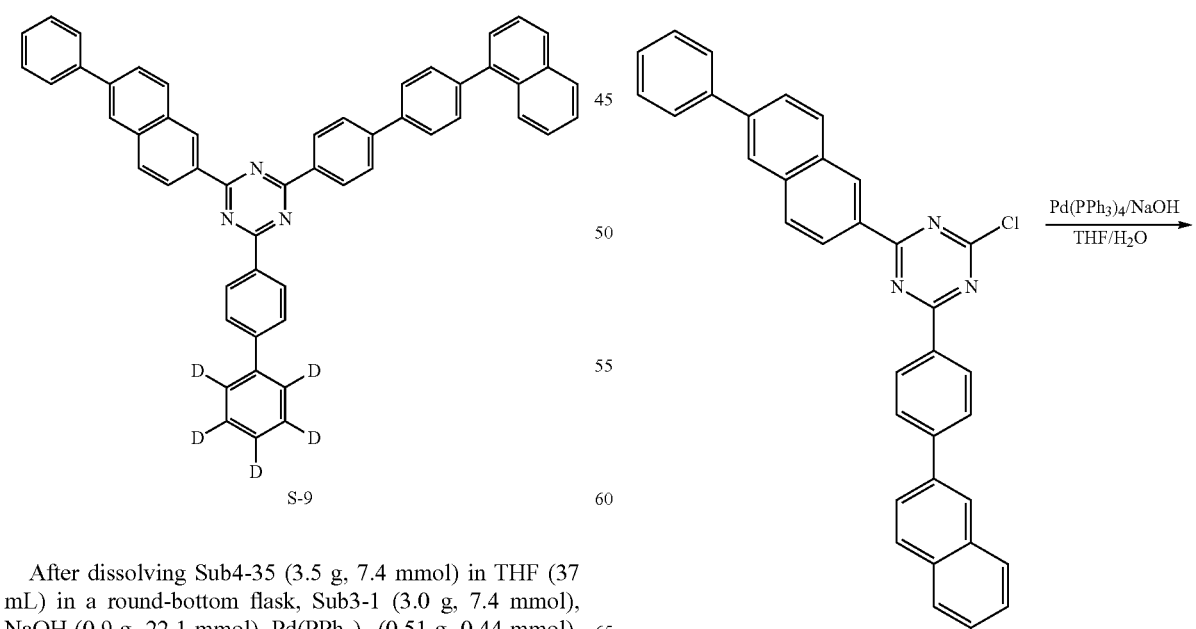

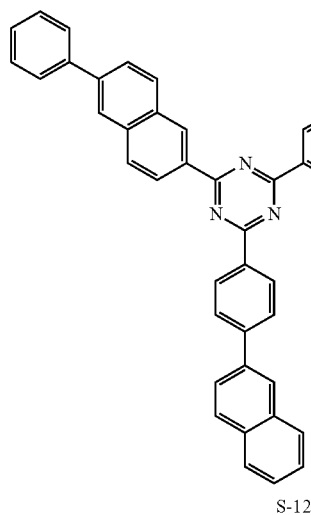

S-12

After dissolving Sub4-20 (3.8 g, 7.4 mmol) in THF (37 mL) in a round-bottom flask, Sub3-1 (3.0 g, 7.4 mmol), NaOH (0.9 g, 22.1 mmol), Pd(PPh$_3$)$_4$ (0.51 g, 0.44 mmol), water (18 mL) were added, and 4.4 g (yield 78%) of the product was obtained using the above synthesis method of S-1.

4. Synthesis Example of S-21

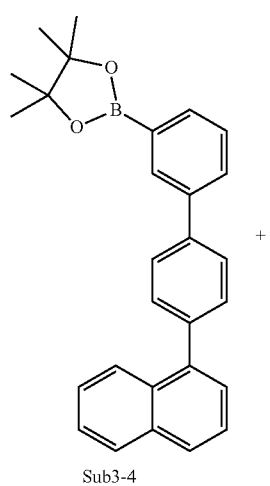

Sub3-4

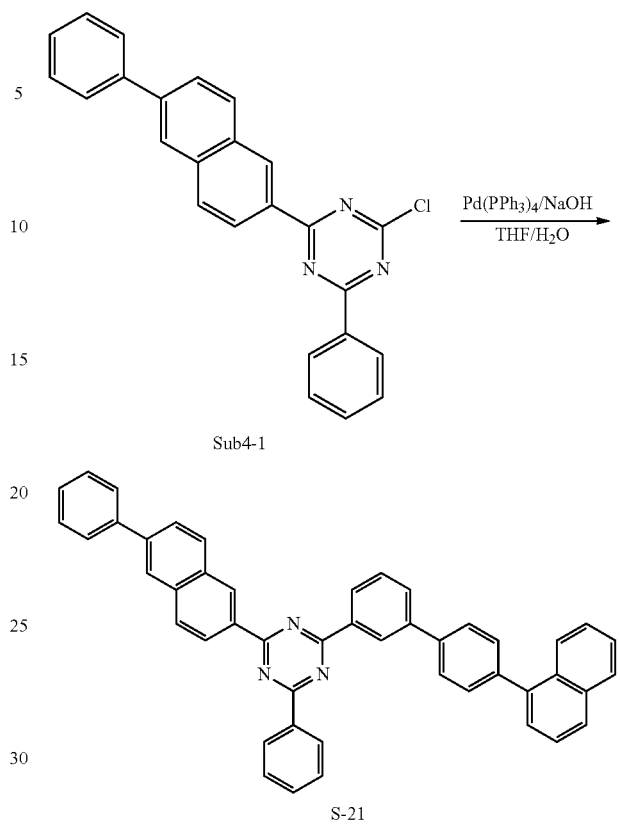

After dissolving Sub4-1 (2.9 g, 7.4 mmol) in THF (37 mL) in a round-bottom flask, Sub3-4 (3.0 g, 7.4 mmol), NaOH (0.9 g, 22.1 mmol), Pd(PPh$_3$)$_4$ (0.51 g, 0.44 mmol), water (18 mL) were added and 3.8 g (yield 80%) of the product was obtained by using the synthesis method of S-1.

5. Synthesis Example of S-33

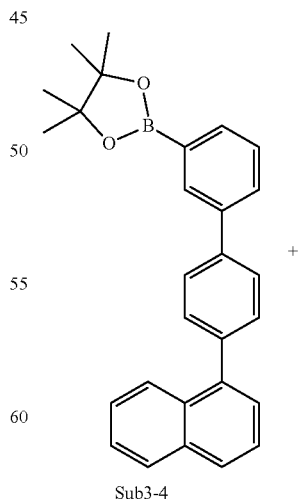

Sub3-4

71
-continued

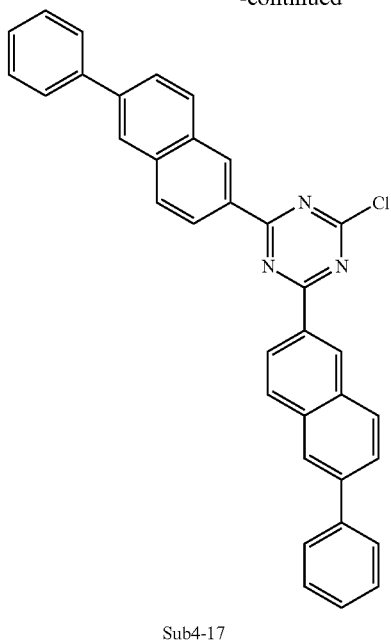

Sub4-17

6. Synthesis Example of S-36

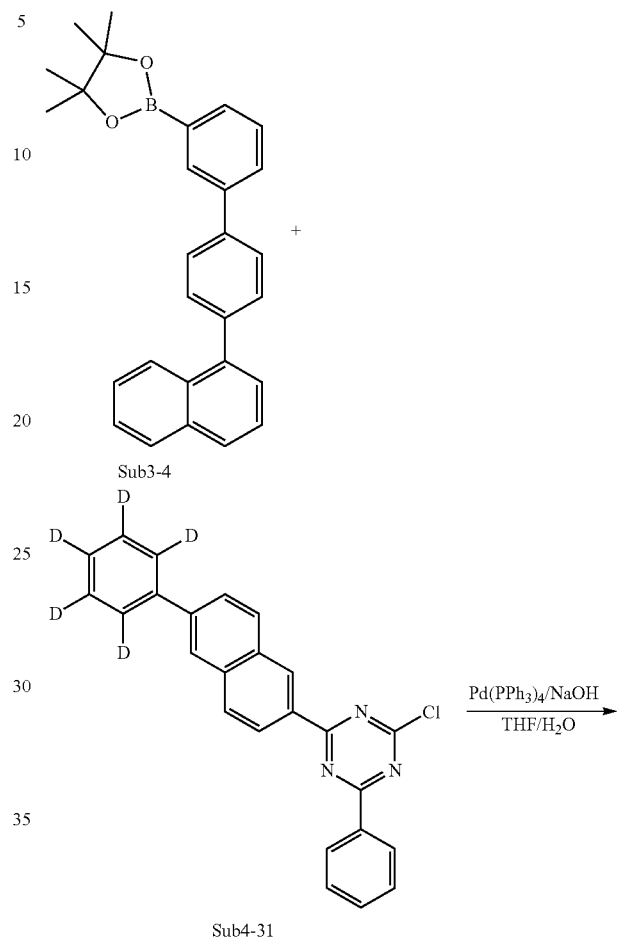

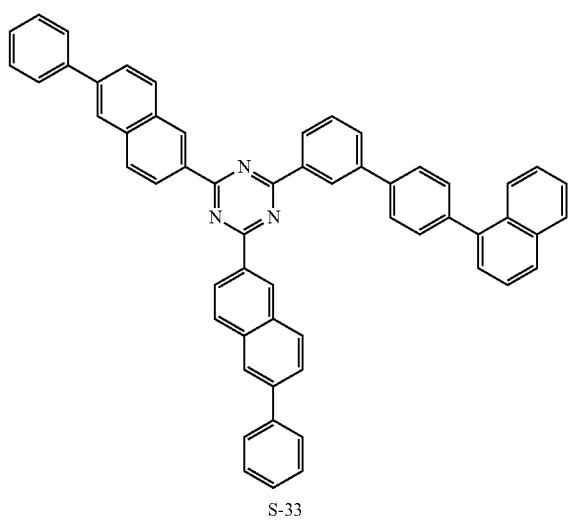

S-33

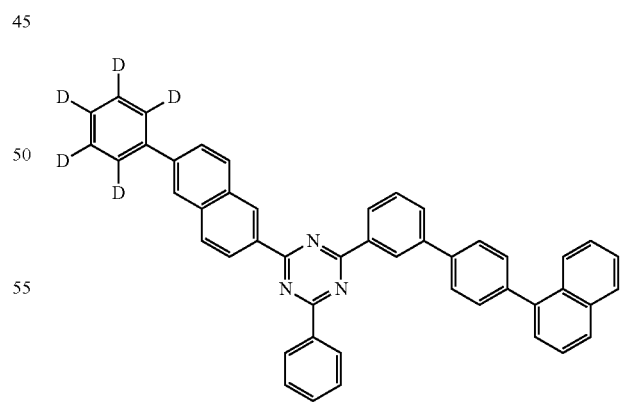

S-36

After dissolving Sub4-17 (3.8 g, 7.4 mmol) in THF (37 mL) in a round-bottom flask, Sub3-4 (3.0 g, 7.4 mmol), NaOH (0.9 g, 22.1 mmol), Pd(PPh$_3$)$_4$ (0.51 g, 0.44 mmol), water (18 mL) were added and 4.3 g (yield 77%) of the product was obtained by using the synthesis method of S-1.

After dissolving Sub4-31 (2.9 g, 7.4 mmol) in THF (37 mL) in a round-bottom flask, Sub3-4 (3.0 g, 7.4 mmol), NaOH (0.9 g, 22.1 mmol), Pd(PPh$_3$)$_4$ (0.51 g, 0.44 mmol), water (18 mL) were added, and 3.7 g (yield 78%) of the product was obtained by using the synthesis method of S-1.

7. Synthesis Example of S-41

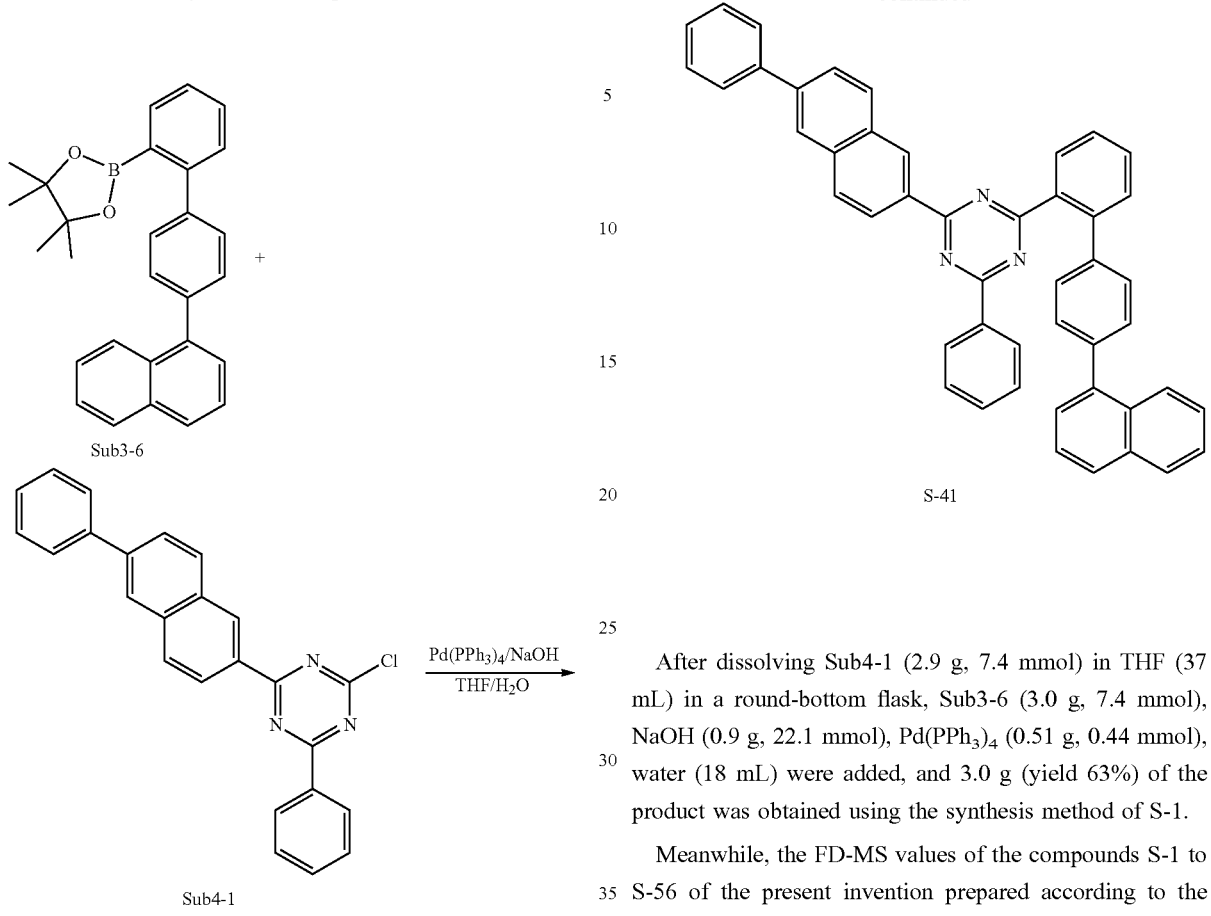

After dissolving Sub4-1 (2.9 g, 7.4 mmol) in THF (37 mL) in a round-bottom flask, Sub3-6 (3.0 g, 7.4 mmol), NaOH (0.9 g, 22.1 mmol), Pd(PPh$_3$)$_4$ (0.51 g, 0.44 mmol), water (18 mL) were added, and 3.0 g (yield 63%) of the product was obtained using the synthesis method of S-1.

Meanwhile, the FD-MS values of the compounds S-1 to S-56 of the present invention prepared according to the above synthesis examples are shown in Table 3 below.

TABLE 3

| compound | FD-MS | compound | FD-MS |
| --- | --- | --- | --- |
| S-1  | m/z = 637.25($C_{47}H_{31}N_3$ = 637.79)     | S-2  | m/z = 687.27($C_{51}H_{33}N_3$ = 687.85)     |
| S-3  | m/z = 687.27($C_{51}H_{33}N_3$ = 687.85)     | S-4  | m/z = 713.28($C_{53}H_{35}N_3$ = 713.88)     |
| S-5  | m/z = 713.28($C_{53}H_{35}N_3$ = 713.88)     | S-6  | m/z = 713.28($C_{53}H_{35}N_3$ = 713.88)     |
| S-7  | m/z = 789.31($C_{59}H_{39}N_3$ = 789.98)     | S-8  | m/z = 763.3($C_{57}H_{37}N_3$ = 763.94)      |
| S-9  | m/z = 718.31($C_{53}H_{30}D_5N_3$ = 718.91)  | S-10 | m/z = 641.28($C_{47}H_{27}D_4N_3$ = 641.81)  |
| S-11 | m/z = 763.3($C_{57}H_{37}N_3$ = 763.94)      | S-12 | m/z = 763.3($C_{57}H_{37}N_3$ = 763.94)      |
| S-13 | m/z = 763.3($C_{57}H_{37}N_3$ = 763.94)      | S-14 | m/z = 763.3($C_{57}H_{37}N_3$ = 763.94)      |
| S-15 | m/z = 769.34($C_{57}H_{31}D_6N_3$ = 769.98)  | S-16 | m/z = 763.3($C_{57}H_{37}N_3$ = 763.94)      |
| S-17 | m/z = 863.33($C_{65}H_{41}N_3$ = 864.06)     | S-18 | m/z = 813.31($C_{61}H_{39}N_3$ = 814)        |
| S-19 | m/z = 847.38($C_{63}H_{33}D_8N_3$ = 848.09)  | S-20 | m/z = 789.31($C_{59}H_{39}N_3$ = 789.98)     |
| S-21 | m/z = 637.25($C_{47}H_{31}N_3$ = 637.79)     | S-22 | m/z = 713.28($C_{53}H_{35}N_3$ = 713.88)     |
| S-23 | m/z = 713.28($C_{53}H_{35}N_3$ = 713.88)     | S-24 | m/z = 713.28($C_{53}H_{35}N_3$ = 713.88)     |
| S-25 | m/z = 642.28($C_{47}H_{26}D_5N_3$ = 642.82)  | S-26 | m/z = 687.27($C_{51}H_{33}N_3$ = 687.85)     |
| S-27 | m/z = 687.27($C_{51}H_{33}N_3$ = 687.85)     | S-28 | m/z = 737.28($C_{55}H_{35}N_3$ = 737.91)     |
| S-29 | m/z = 763.3($C_{57}H_{37}N_3$ = 763.94)      | S-30 | m/z = 763.3($C_{57}H_{37}N_3$ = 763.94)      |
| S-31 | m/z = 813.31($C_{61}H_{39}N_3$ = 814)        | S-32 | m/z = 763.3($C_{57}H_{37}N_3$ = 763.94)      |
| S-33 | m/z = 763.3($C_{57}H_{37}N_3$ = 763.94)      | S-34 | m/z = 737.28($C_{55}H_{35}N_3$ = 737.91)     |
| S-35 | m/z = 763.3($C_{57}H_{37}N_3$ = 763.94)      | S-36 | m/z = 642.28($C_{47}H_{26}D_5N_3$ = 642.82)  |
| S-37 | m/z = 763.3($C_{57}H_{37}N_3$ = 763.94)      | S-38 | m/z = 813.31($C_{61}H_{39}N_3$ = 814)        |
| S-39 | m/z = 718.31($C_{53}H_{30}D_5N_3$ = 718.91)  | S-40 | m/z = 640.27($C_{47}H_{28}D_3N_3$ = 640.8)   |
| S-41 | m/z = 637.25($C_{47}H_{31}N_3$ = 637.79)     | S-42 | m/z = 713.28($C_{53}H_{35}N_3$ = 713.88)     |
| S-43 | m/z = 713.28($C_{53}H_{35}N_3$ = 713.88)     | S-44 | m/z = 763.3($C_{57}H_{37}N_3$ = 763.94)      |
| S-45 | m/z = 813.31($C_{61}H_{39}N_3$ = 814)        | S-46 | m/z = 687.27($C_{51}H_{33}N_3$ = 687.85)     |
| S-47 | m/z = 687.27($C_{51}H_{33}N_3$ = 687.85)     | S-48 | m/z = 763.3($C_{57}H_{37}N_3$ = 763.94)      |
| S-49 | m/z = 737.28($C_{55}H_{35}N_3$ = 737.91)     | S-50 | m/z = 763.3($C_{57}H_{37}N_3$ = 763.94)      |
| S-51 | m/z = 763.3($C_{57}H_{37}N_3$ = 763.94)      | S-52 | m/z = 642.28($C_{47}H_{26}D_5N_3$ = 642.82)  |
| S-53 | m/z = 648.32($C_{47}H_{20}D_{11}N_3$ = 648.85) | S-54 | m/z = 641.28($C_{47}H_{27}D_4N_3$ = 641.81) |
| S-55 | m/z = 789.31($C_{59}H_{39}N_3$ = 789.98)     | S-56 | m/z = 763.3($C_{57}H_{37}N_3$ = 763.94)      |

Example 25 Red Organic Light Emitting Device (Phosphorescent Host)

An organic electroluminescent device was manufactured according to a conventional method by using the compound obtained through synthesis as a light emitting host material of the light emitting layer.

First, after vacuum deposition of N1-(naphthalen-2-yl)-N4, N4-bis(4-(naphthalen-2-yl(phenyl)amino)phenyl)-N1-phenylbenzene-1,4-diamine (hereinafter 2-TANA) film on the ITO layer (anode) formed on a glass substrate to form a hole injection layer with a thickness of 60 nm, on the hole injection layer, 4,4-bis[N-(1-naphthyl)-N-phenylamino]biphenyl (hereinafter —NPD) as a hole transport compound was vacuum-deposited to a thickness of 50 nm to form a hole transport layer. An emitting-auxiliary layer was formed by vacuum-depositing tris(4-(9H-carbazol-9-yl)phenyl) amine (hereinafter TCTA) to a thickness of 10 nm as an emitting-auxiliary layer material on the hole transport layer. After forming the emitting-auxiliary layer.

An emitting layer was deposited to a thickness of 30 nm by doping the compound S-1 of the present invention represented by Formula 2 as a host and (piq)$_2$Ir(acac) as a dopant material on the upper portion of the emitting auxiliary layer in a 95:5 weight ratio.

Subsequently, (1,1'-bisphenyl)-4-oleato)bis(2-methyl-8-quinolineoleato)aluminum (hereinafter BAlq) was vacuum-deposited to a thickness of 10 nm as a hole blocking layer, and bis(10-hydroxybenzo[h]quinolinato)beryllium (hereinafter BeBq2) was formed as an electron transport layer to a thickness of 25 nm. Thereafter, LiF, which is an alkali metal halide, was deposited as an electron injection layer to a thickness of 0.2 nm, and then Al was deposited to a thickness of 150 nm and used as a cathode to prepare an organic electroluminescent device.

Example 26 to Example 29

An organic electroluminescent device was manufactured in the same manner as in Example 25, except that the compound of the present invention described in Table 4 was used instead of the compound S-1 of the present invention as the host material of the emitting layer.

Example 30

An organic electroluminescent device was manufactured in the same manner as in Example 25, except that the first compound, the compound S-1 of the present invention, and the compound C-1, of the present invention, were used as a host material for the emitting layer in a weight ratio of 5:5.

Example 31 to Example 41

An organic electroluminescent device was manufactured in the same manner as in Example 25, except for using the compound of the present invention shown in Table 4 below and compound C-1 or compound C-2 in a weight ratio of 5:5 instead of the compound S-1 of the present invention, which is the first compound, as the host material of the emitting layer

Comparative Example 13 to Comparative Example 14

An organic electroluminescent device was manufactured in the same manner as in Example 25, except that Comparative Compound E or Comparative Compound F was used instead of Compound S-1 of the present invention as a host material for the emitting layer.

Comparative Example 15 to Comparative Example 18

An organic electroluminescent device was manufactured in the same manner as in Example 25, except that Comparative Compound A or Comparative Compound B and Compound C-1 or Compound C-2 were used as a host material for the emitting layer in a weight ratio of 5:5.

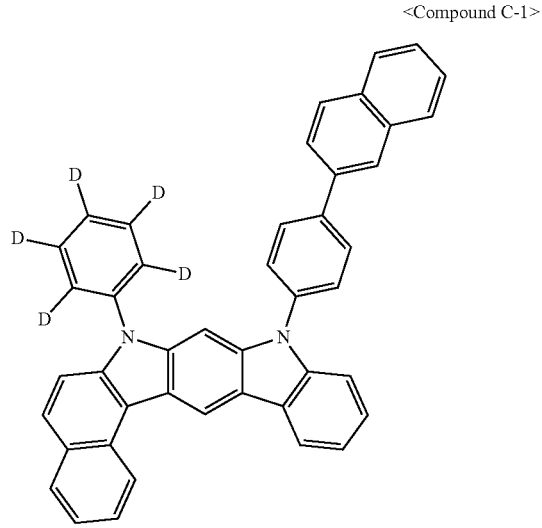

<Compound C-1>

<Compound C-2>

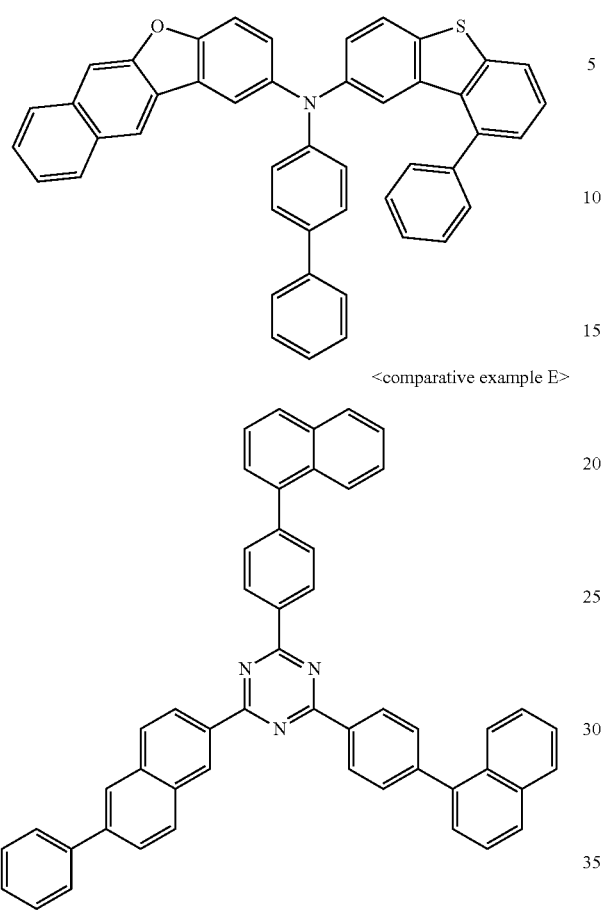

<comparative example E>

<comparative example F>

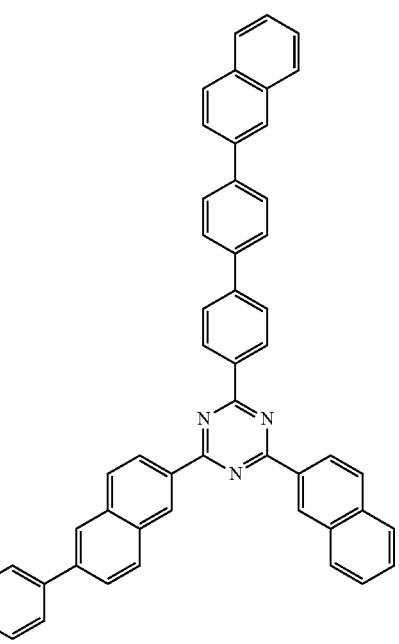

A forward bias DC voltage was applied to the organic electric devices prepared in Examples 25 to 41 and Comparative Examples 13 to 18 prepared in this way, and electroluminescence (EL) characteristics were measured with a PR-650 of Photo Research, as a result of the measurement, the T95 lifetime was measured using a lifetime measuring device manufactured by McScience at a standard luminance of 2500 cd/m$^2$. Table 4 below shows the device fabrication and evaluation results.

TABLE 4

| | fitst compound | second compound | Voltage (v) | Current Density (mA/cm$^2$) | Brightness (cd/m$^2$) | Efficiency (cd/A) | T(95) |
|---|---|---|---|---|---|---|---|
| comparative example13 | comparative compound E | — | 5.8 | 17.1 | 2500 | 14.6 | 84.3 |
| comparative example14 | comparative compound F | — | 5.6 | 16.4 | 2500 | 15.2 | 92.4 |
| comparative example15 | comparative compound E | compound (C-1) | 5.6 | 14.5 | 2500 | 17.3 | 98.1 |
| comparative example16 | comparative compound F | | 5.5 | 13.6 | 2500 | 18.4 | 104.3 |
| comparative example17 | comparative compound E | compound (C-2) | 5.4 | 14.7 | 2500 | 17.0 | 97.4 |
| comparative example18 | comparative compound F | | 5.3 | 13.7 | 2500 | 18.2 | 103.7 |
| example25 | compound (S-1) | — | 5.0 | 12.1 | 2500 | 20.7 | 112.4 |
| example26 | compound (S-3) | — | 5.0 | 12.6 | 2500 | 19.8 | 114.5 |
| example27 | compound (S-21) | — | 5.1 | 11.7 | 2500 | 21.3 | 115.7 |
| example28 | compound (S-36) | — | 5.1 | 11.6 | 2500 | 21.5 | 118.2 |
| example29 | compound (S-41) | — | 5.2 | 12.9 | 2500 | 19.4 | 110.6 |
| example30 | compound (S-1) | compound (C-1) | 4.7 | 9.7 | 2500 | 25.8 | 133.2 |
| example31 | compound (S-3) | | 4.7 | 10.3 | 2500 | 24.3 | 134.8 |
| example32 | compound (S-21) | | 4.8 | 8.0 | 2500 | 31.4 | 142.2 |

TABLE 4-continued

|  | fitst compound | second compound | Voltage (v) | Current Density (mA/cm$^2$) | Brightness (cd/m$^2$) | Efficiency (cd/A) | T(95) |
|---|---|---|---|---|---|---|---|
| example33 | compound (S-28) |  | 4.9 | 8.9 | 2500 | 28.1 | 138.1 |
| example34 | compound (S-36) |  | 4.8 | 7.9 | 2500 | 31.7 | 145.4 |
| example35 | compound (S-41) |  | 5.0 | 10.6 | 2500 | 23.5 | 125.4 |
| example36 | compound (S-1) | compound (C-2) | 4.5 | 10.1 | 2500 | 24.7 | 125.1 |
| example37 | compound (S-3) |  | 4.5 | 10.7 | 2500 | 23.4 | 126.4 |
| example38 | compound (S-21) |  | 4.6 | 8.7 | 2500 | 28.9 | 132.2 |
| example39 | compound (S-28) |  | 4.7 | 9.4 | 2500 | 26.7 | 128.4 |
| example40 | compound (S-36) |  | 4.6 | 8.3 | 2500 | 30.0 | 134.1 |
| example41 | compound (S-41) |  | 4.9 | 11.2 | 2500 | 22.4 | 120.4 |

As can be seen in Table 4, when the compound of the present invention is used as an emitting layer host material, it can be seen that the driving voltage is lowered and the efficiency and lifespan are significantly improved compared to the case of using the comparative compound E or the comparative compound F.

Looking at the examples, it can be seen that the overall performance of the device is better when a plurality of compounds are mixed and used than when the emitting layer host compound is used alone. In Comparative Example, it can be confirmed that properties are improved when a plurality of compounds are mixed and used.

As can be seen above, when a plurality of compounds are mixed to form a host of the light emitting layer, the characteristics are different depending on the type of the first compound and the second compound, and when the same compound is applied to the second compound, it can be seen that the characteristic difference is remarkably displayed depending on the type of the first compound. Similarly, the second compound shows differences in driving voltage, efficiency, and lifespan depending on the type.

Reorganization energy (hereinafter, abbreviated as RE) refers to energy lost due to a change in molecular structure arrangement when electric charges (electrons, holes) move. It depends on molecular geometry, and has a characteristic that the value decreases as the difference between the potential energy surface (hereinafter, abbreviated as PES) in the neutral state and the PES in the charge state decreases. The RE value can be obtained by the following formula.

$$RE_{hole}: \lambda^+ = (E_{NOCE} - E_{COCE}) + (E_{CONE} - E_{NONE})$$

$$RE_{elec}: \lambda^- = (E_{NOAE} - E_{AOAE}) + (E_{AONE} - E_{NONE})$$

Each factor can be defined as follows.
NONE: Neutral geometry of neutral molecules (hereinafter, NO opt.)
NOAE: Anion geometry of a neutral molecule
NOCE: Cation geometry of a neutral molecule
AONE: Neutral geometry of anion molecule
AOAE: Anion geometry of anion molecule (hereinafter, AO opt.)
CONE: Neutral geometry of cation molecule
COCE: Cation geometry of cation molecule (hereinafter, CO opt.)

Reorganization energy and mobility are in inverse proportion to each other, and under the condition that they have the same r and T values, the RE value directly affects mobility for each material. The relation between RE value and mobility is expressed as follows.

$$\mu = k \frac{r^2}{2k_B T/e}$$

$$k = \left(\frac{4\pi^2}{h}\right) \frac{t^2}{\sqrt{4\pi \lambda k_B T}} \exp\left[-\frac{\lambda}{4k_B T}\right]$$

Each factor can be defined as follows.
λ: Reorganization energy
μ: mobility
r: dimer displacement
t: intermolecular charge transfer matrix element From the above formula, it can be seen that the lower the RE value, the faster the mobility.

The RE value requires a simulation tool that can calculate the potential energy according to the molecular structure, and we used Gaussian09 (hereafter, G09) and the Jaguar (hereafter, JG) module of Schrodinger Materials Science. Both G09 and JG are tools to analyze the properties of molecules through quantum mechanical (hereafter, QM) calculations, and have the function of optimizing the molecular structure or calculating the energy for a given molecular structure (single-point energy).

The process of calculating QM in molecular structure requires large computational resources, and we use two cluster servers for these calculations. Each cluster server consists of 4 node workstations and 1 master workstation, and each node performed molecular QM calculations by parallel computing through symmetric multi-processing (SMP) using a central processing unit (CPU) of 36 or more cores.

Using G09, calculate the optimized molecular structure and its potential energy (NONE/COCE) in the neutral/charged state required for rearrangement energy. The charge state potential energy (NOCE) of the structure optimized for the neutral state and the neutral state potential energy (CONE) of the structure optimized for the charge state were calculated by changing only the charges to the two optimized structures. Then, the rearrangement energy was calculated according to the following relation.

$$RE_{charge}: \lambda = (E_{NOCE} - E_{COCE}) + (E_{CONE} - E_{NONE})$$

Because Schrödinger provides a function to automatically perform such a calculation process, the potential energy according to each state was sequentially calculated through the JG module by providing the molecular structure (NO) of the basic state, and the RE value was calculated.

The calculated reorganization energy values of Comparative Compound E, Comparative Compound F and S-21 are described in Table 5 below. RE values shown in Table 5 are calculated values of $RE_{elec}$.

TABLE 5

| compound | Reorganization Energy (RE) |
|---|---|
| Comparative compound E | 0.2213 |
| Comparative compound F | 0.2378 |
| S-21 | 0.2462 |

Referring to Table 5 above, compared to the comparative compound E or the comparative compound F, S-21 has a higher RE value. These RE values are different depending on the substituent of the triazine, in particular, it can be seen that the compound of the present invention, S-21, has the highest RE value. That is, when it has a high RE value, it means low mobility and slow EOD.

When the light emitting layer is composed of a plurality of mixtures, the driving efficiency and lifetime are determined according to the degree of ease of injection of holes and electrons into the dopant, and when the hole and electron ratio (Charge Balance) is properly maintained, the efficiency and lifespan are dramatically increased.

That is, since it has a relatively high RE value, it is expected that the charge balance of the compound of the present invention represented by Chemical Formula 2 is better, and thus the performance of the device is improved.

It can be confirmed that the characteristics of triazine are very different depending on the type of substituent and the bonding position of the substituent. In particular, as in the present invention, when the -naphthyl-phenyl structure and the -biphenyl-1-naphthyl structure are simultaneously substituted with the substituent of triazine, the effect is considered to be maximized as a synergistic effect Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula (2):

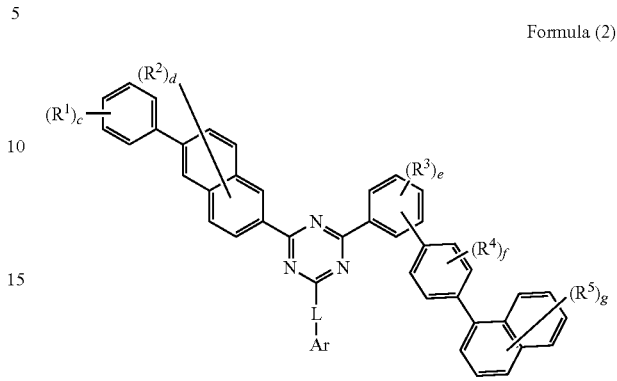

Formula (2)

wherein:
1) $R^1$, $R^2$, $R^3$, $R^4$ and $R^5$ are the same or different from each other, and independently of each other are hydrogen or deuterium;
2) L is a single bond; or $C_6$-$C_{60}$ arylene group;
3) Ar is a $C_6$-$C_{60}$ aryl group;
4) C is an integer of 0 to 5, d is an integer of 0 to 6, e and f are each independently an integer of 0 to 4, and g is an integer of 0 to 7;
5) Wherein the arylene group and the aryl group may be further substituted with one or more substituents selected from the group consisting of deuterium; $C_6$-$C_{20}$ aryl group; $C_6$-$C_{20}$ aryl group substituted with deuterium.

2. The compound of claim 1, wherein L is represented by one of Formulas a-1 to a-20:

<Formula a-1>

<Formula a-2>

<Formula a-3>

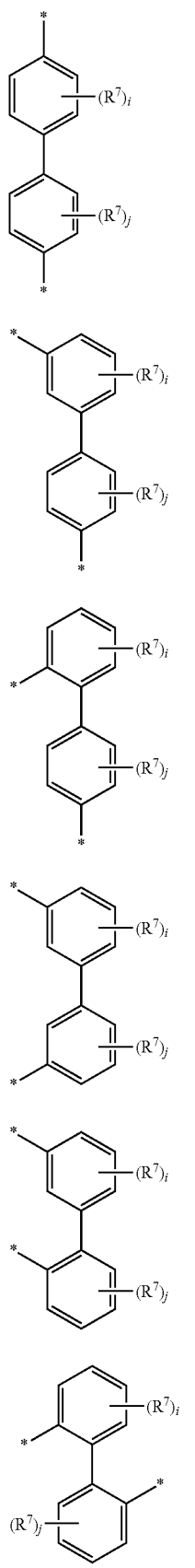
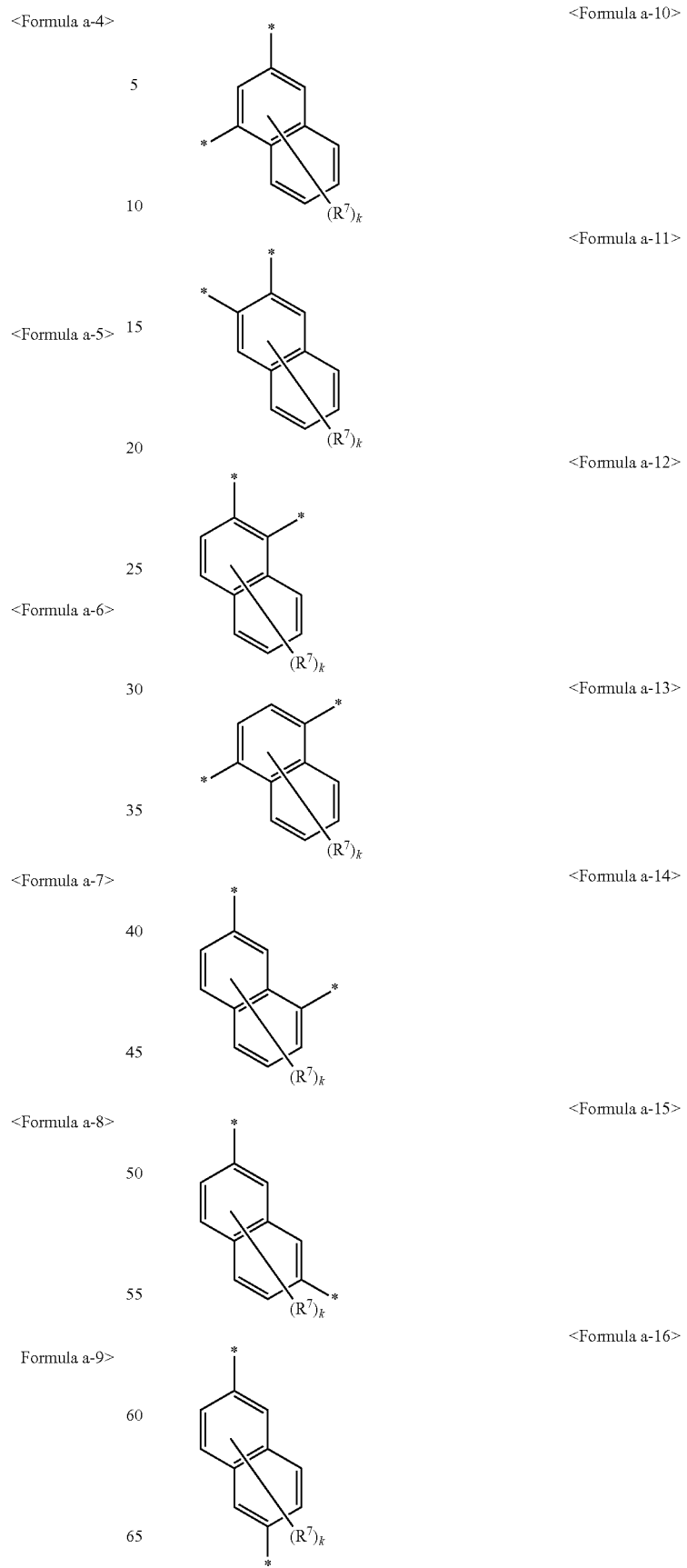

<Formula a-17>

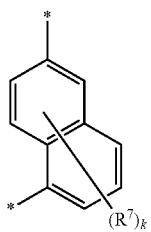

<Formula a-18>

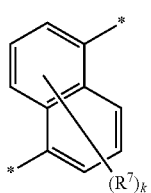

<Formula a-19>

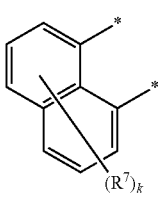

<Formula a-20>

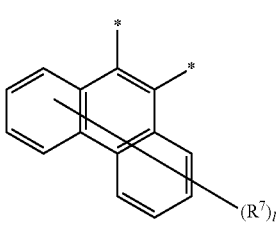

wherein:
1) $R^7$ is selected from the group consisting of a deuterium; a $C_6$~$C_{20}$ aryl group; a $C_6$~$C_{20}$ aryl group substituted with deuterium;
2) h, i and j are each independently an integer from 0 to 4, k is an integer from 0 to 6, l is an integer from 0 to 8;
3) * means a position where triazine or Ar is bonded.

3. The compound of claim 1, wherein Ar is represented by one of Formulas b-1 to b-8:

<Formula b-1>

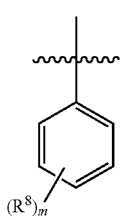

<Formula b-2>

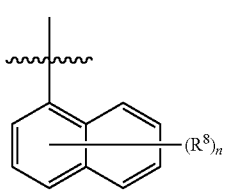

<Formula b-3>

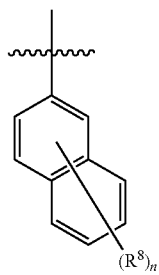

<Formula b-4>

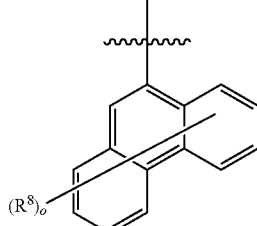

<Formula b-5>

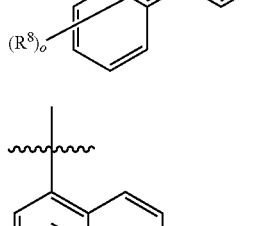

<Formula b-6>

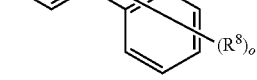

<Formula b-7>

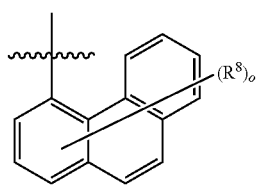

<Formula b-8>

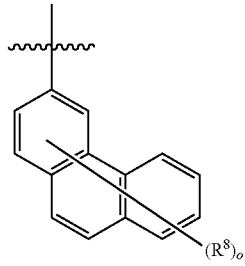

wherein:
1) $R^8$ is selected from the group consisting of a deuterium; a $C_6$~$C_{20}$ aryl group; a $C_6$~$C_{20}$ aryl group substituted with deuterium;
2) m is an integer from 0 to 5, n is an integer from 0 to 7, o is an integer from 0 to 9; and
3) ⁓ means the position where it is combined with L.

4. The compound of claim 1, wherein the compound represented by Formula (2) is selected from the group consisting of compounds S-1 to S-56:

S-1
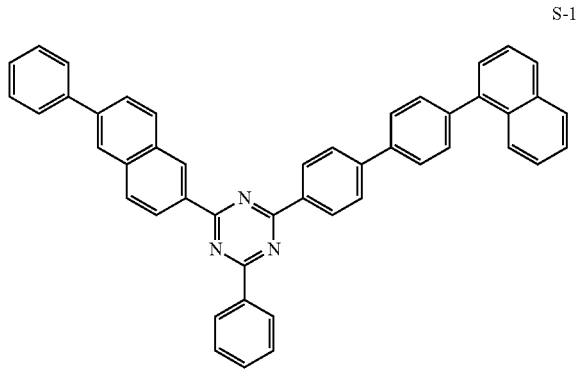

S-2
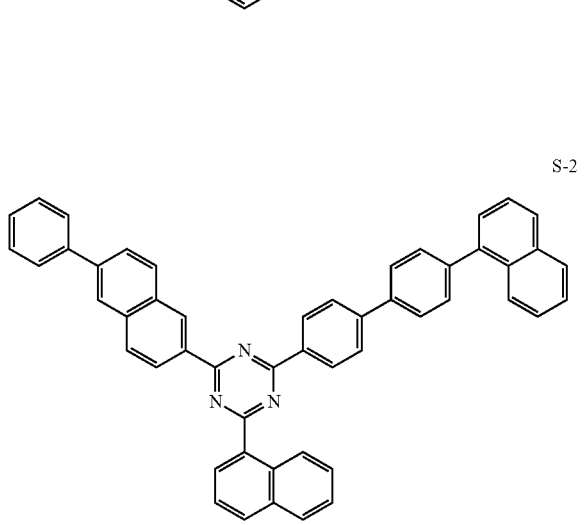

S-3
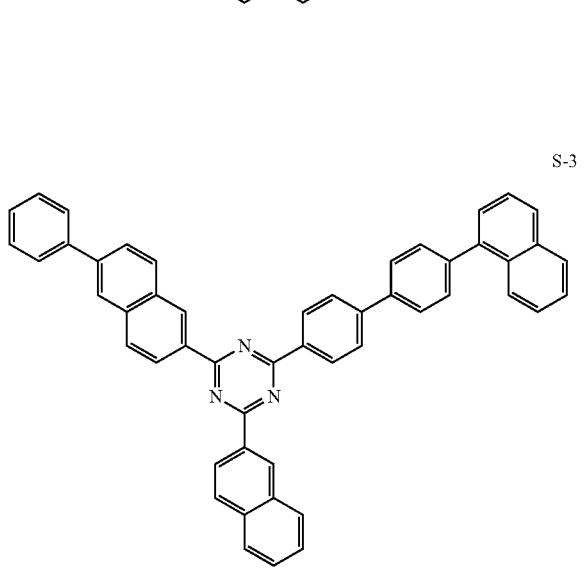

S-4
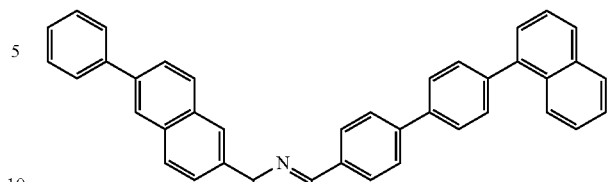

S-5
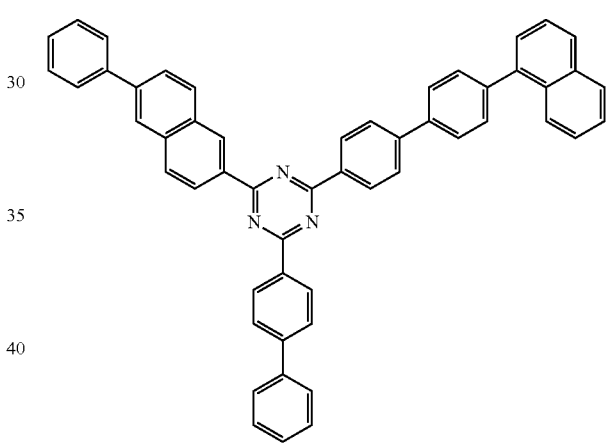

S-6
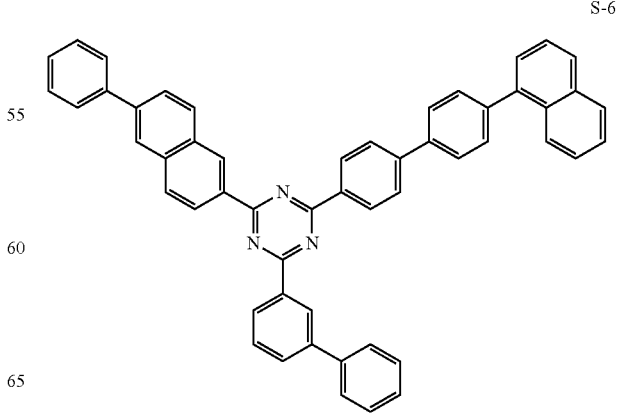

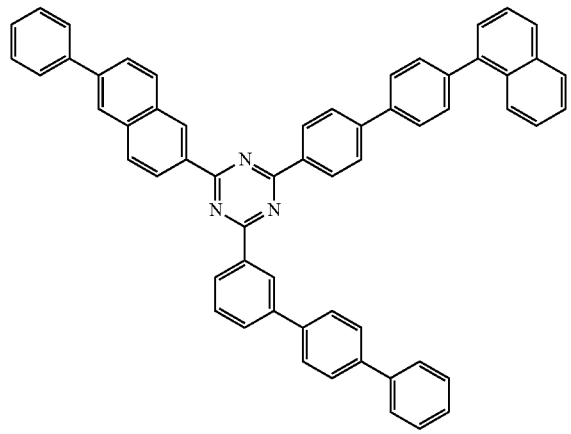
S-7
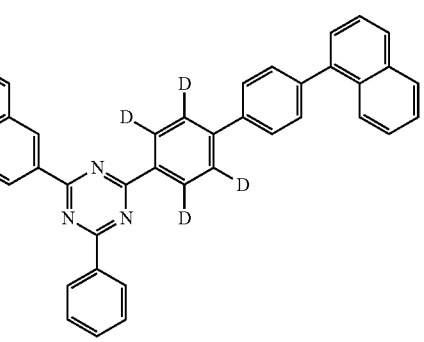
S-10
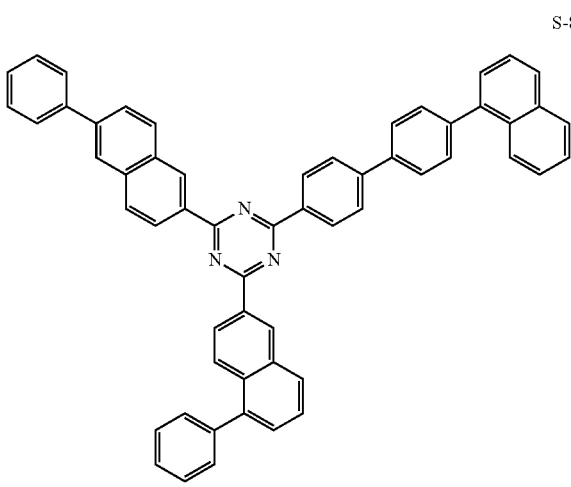
S-8
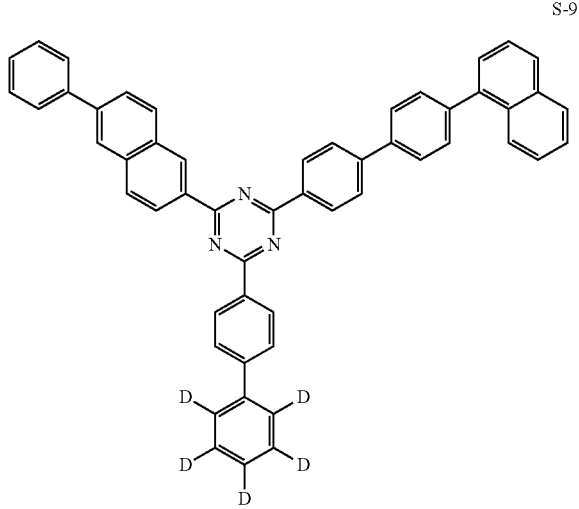
S-9
S-11
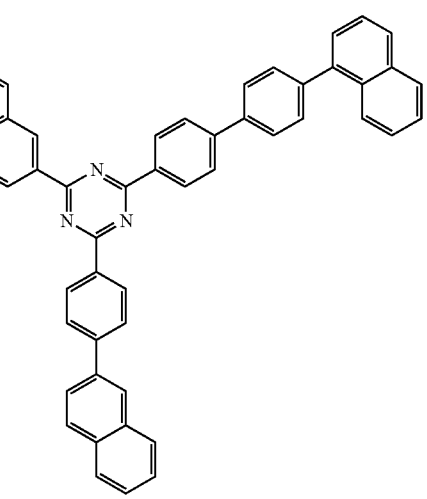
S-12

S-13
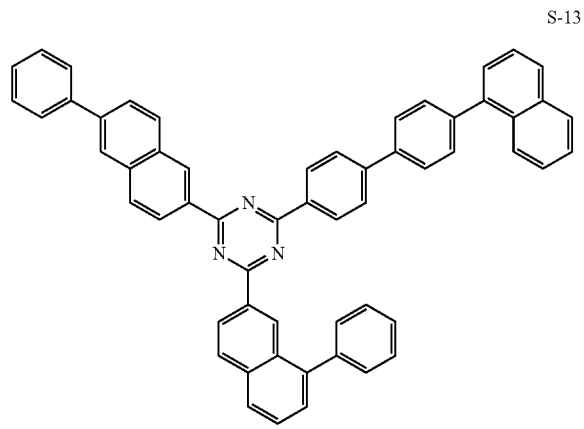
S-16
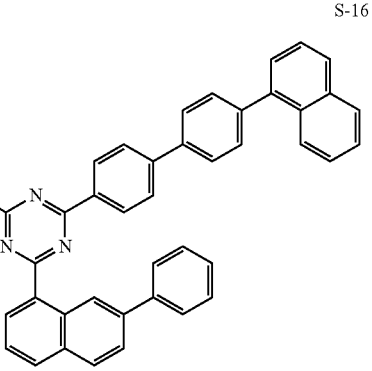
S-14
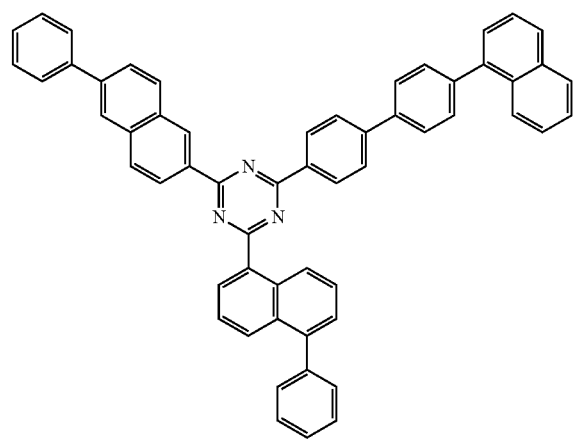
S-17
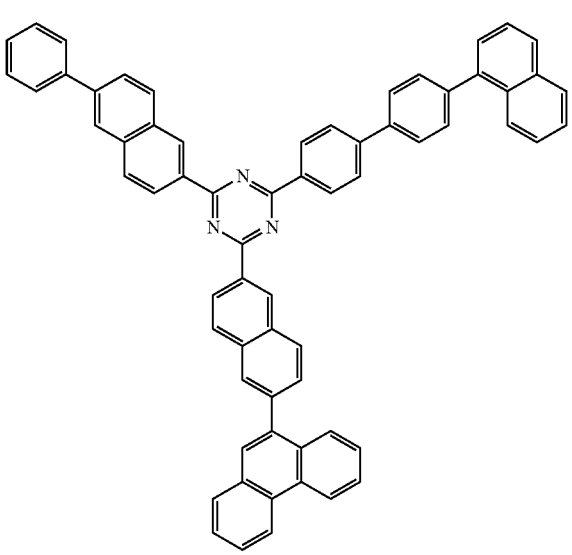
S-15
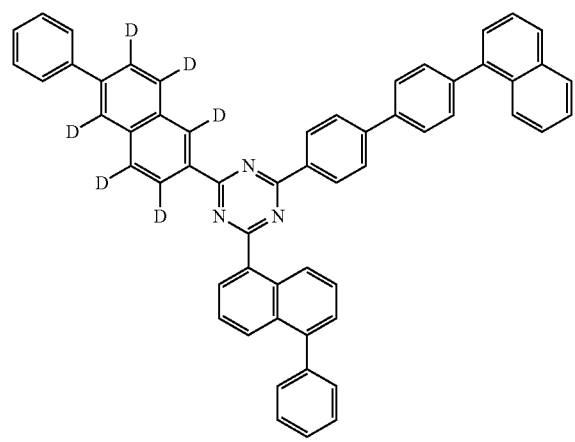
S-18
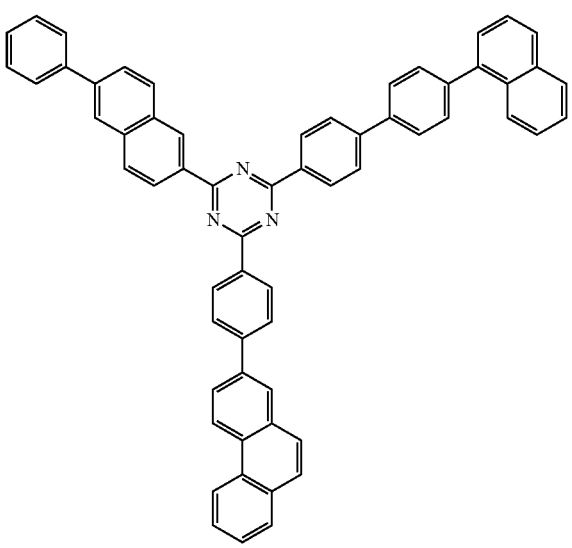

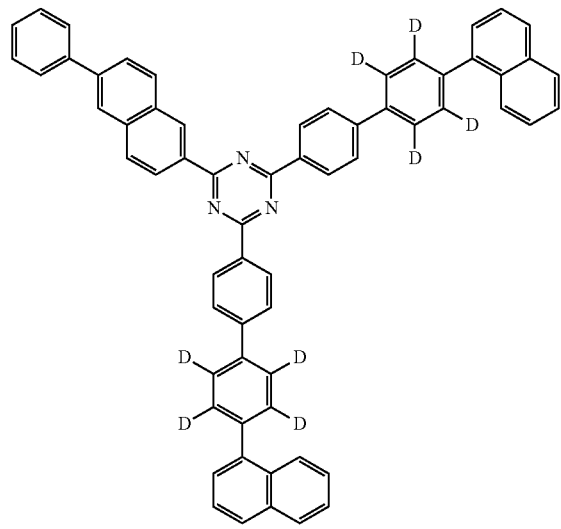
S-19
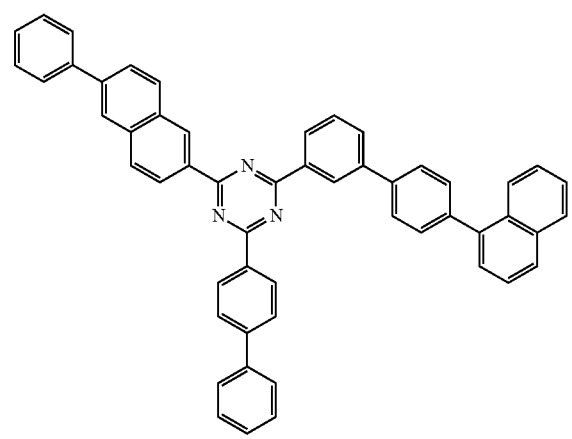
S-22
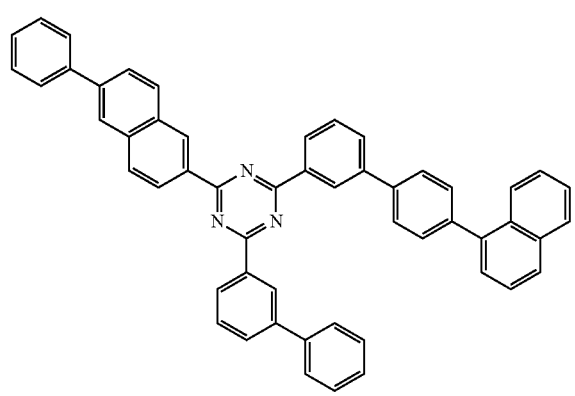
S-23
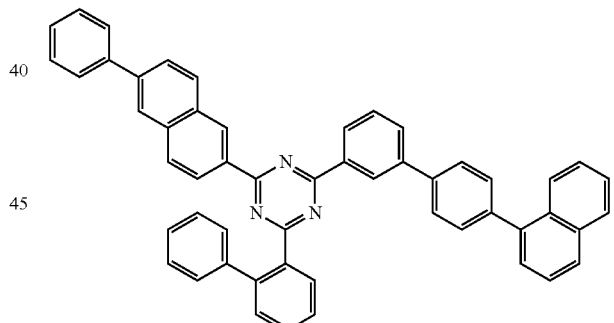
S-24
S-20
S-21
S-25
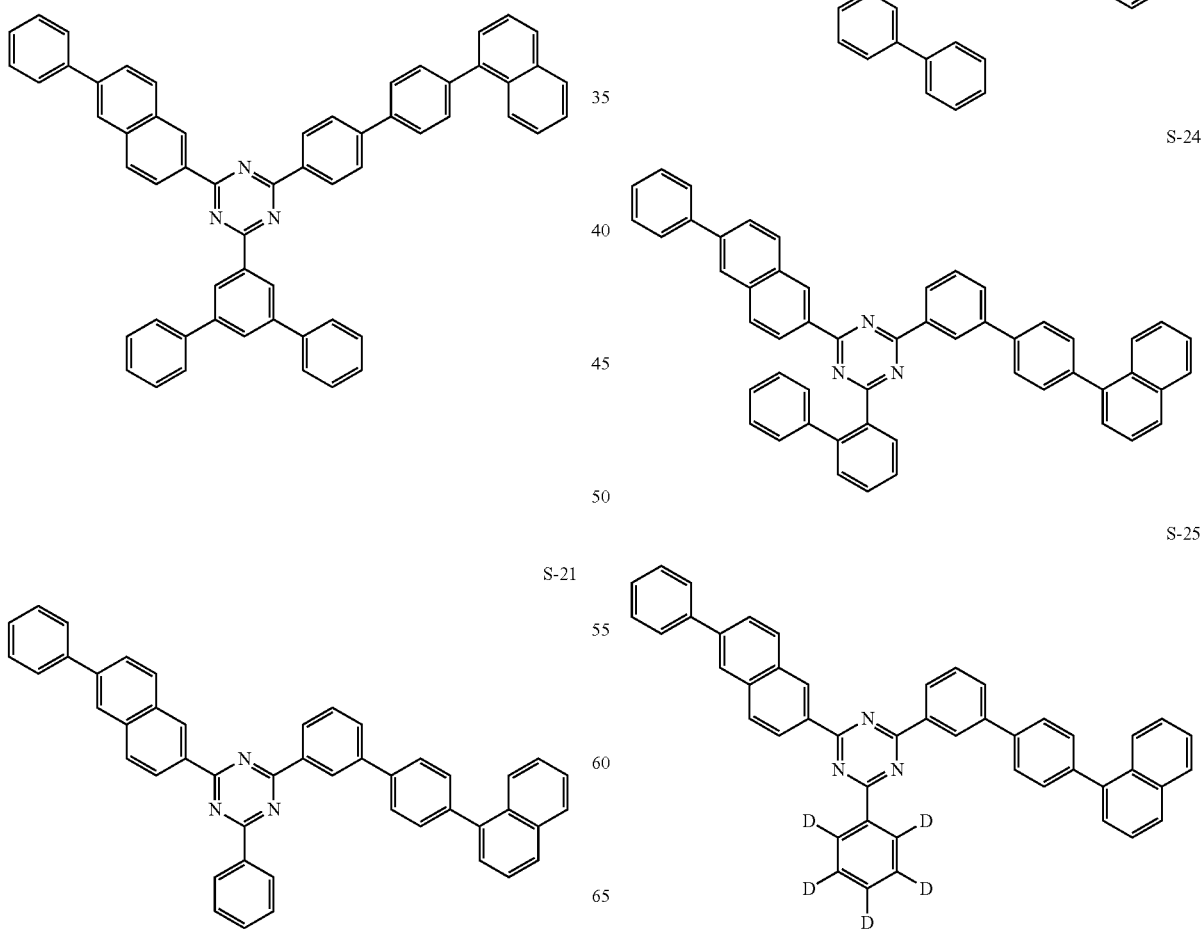

S-26
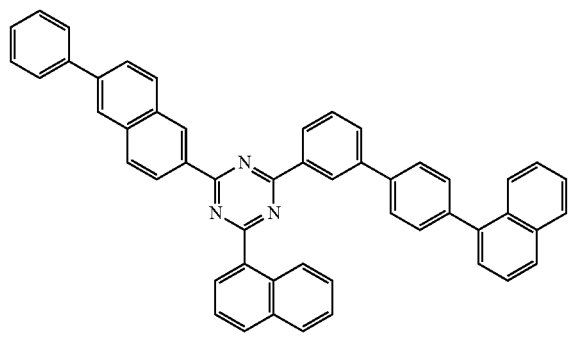
S-27
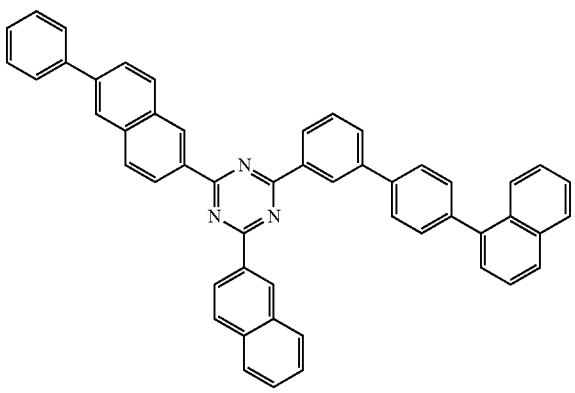
S-28
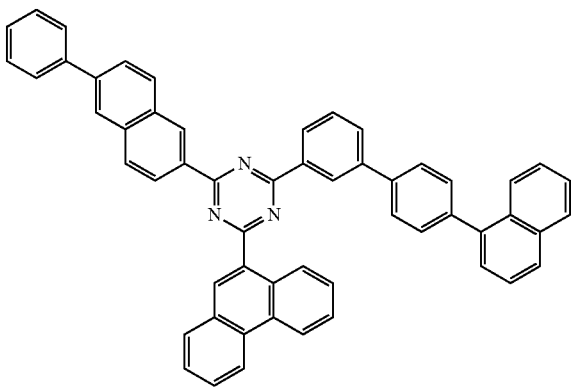
S-29
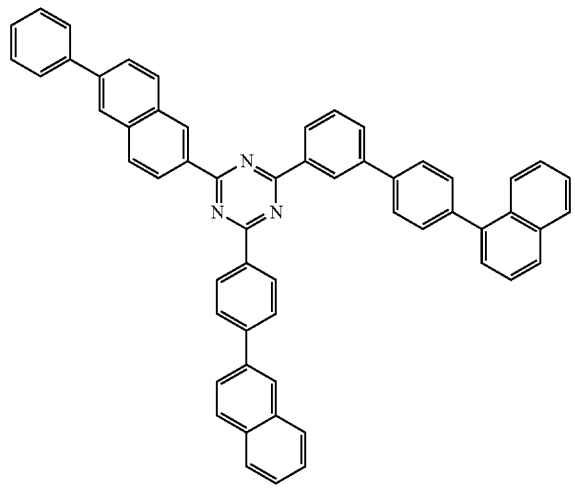
S-30
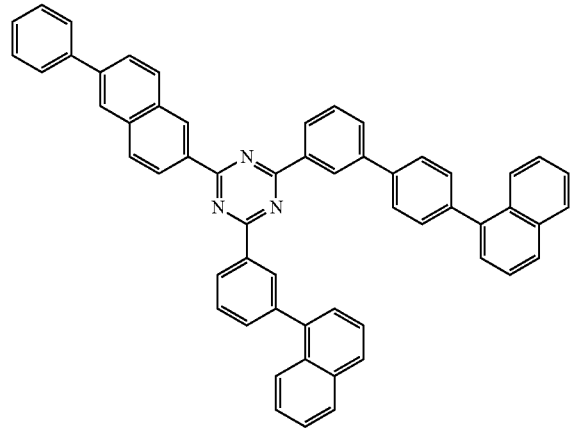
S-31
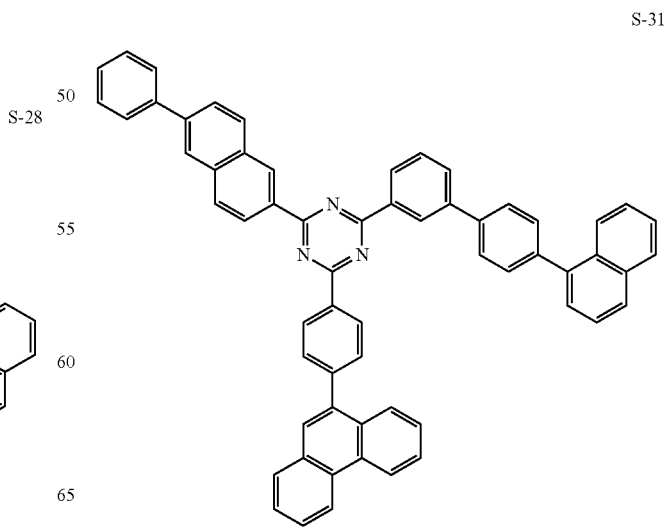

S-32
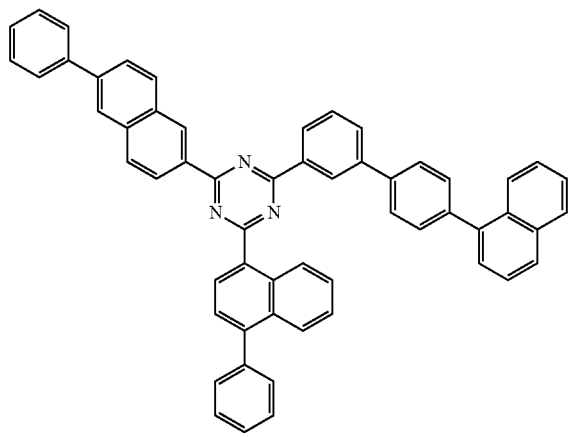
S-35
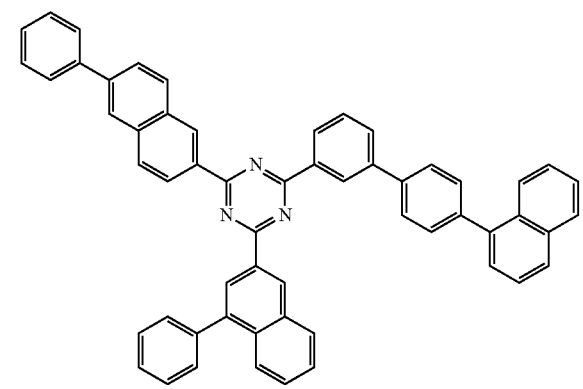
S-33
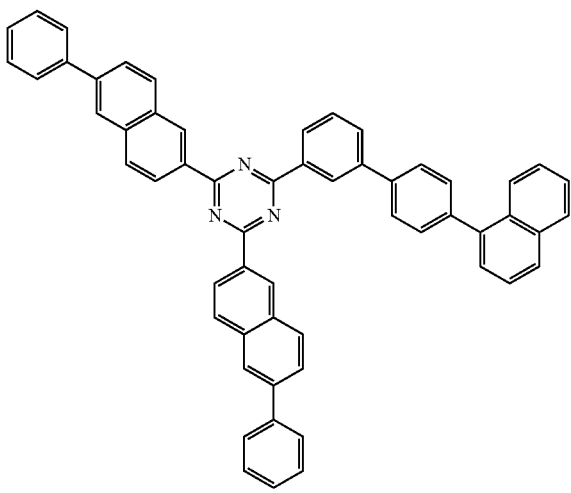
S-36
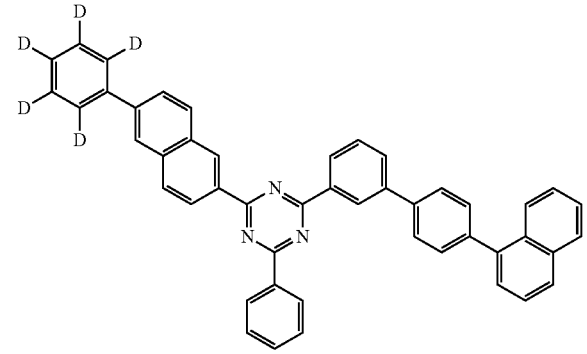
S-34
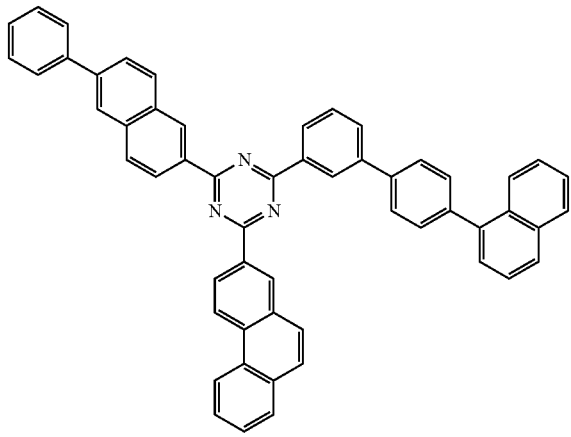
S-37
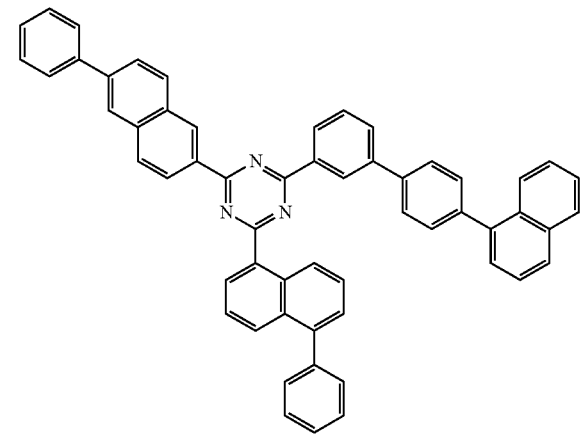

S-38
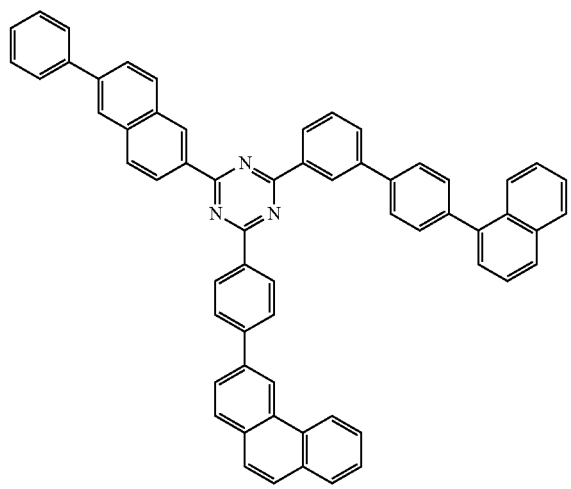
S-39
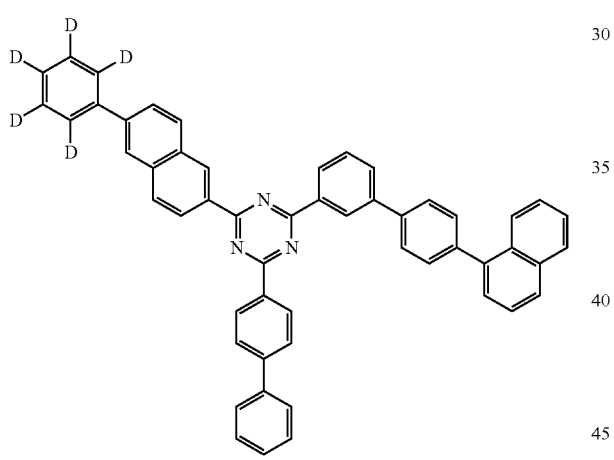
S-40
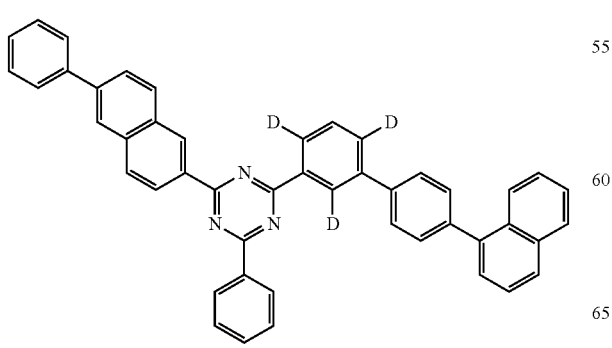
S-41
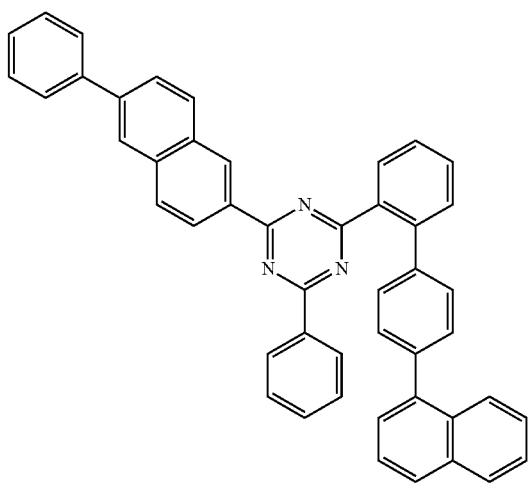
S-42
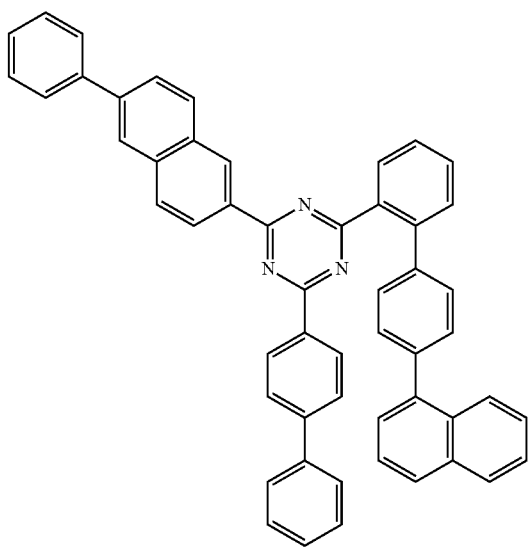
S-43
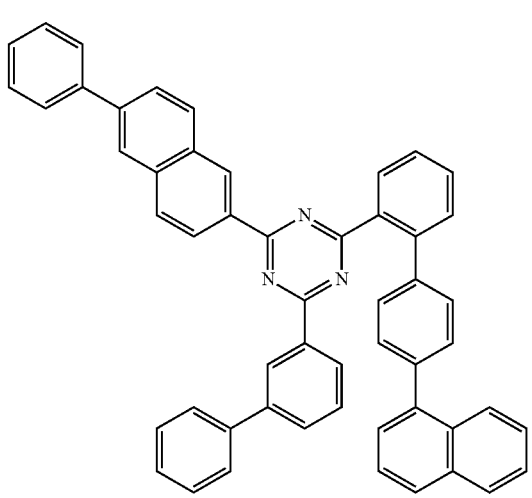

S-44
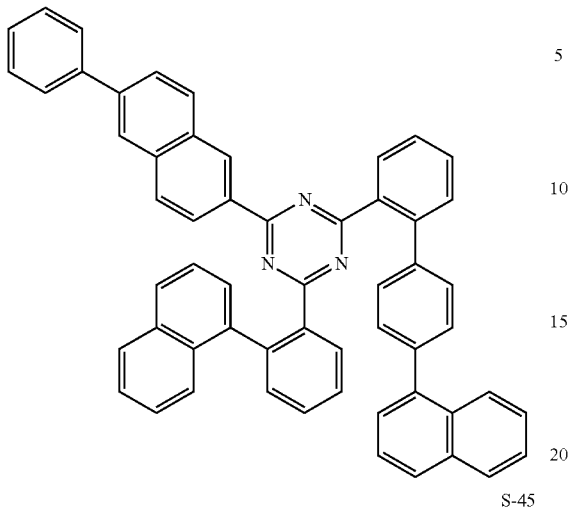
S-45
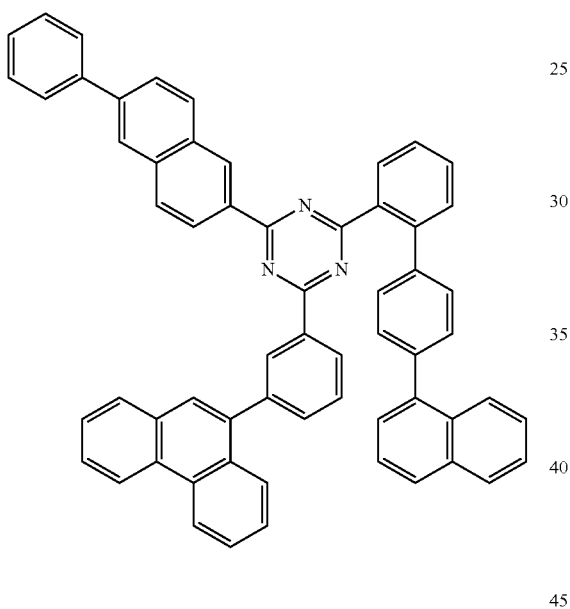
S-46
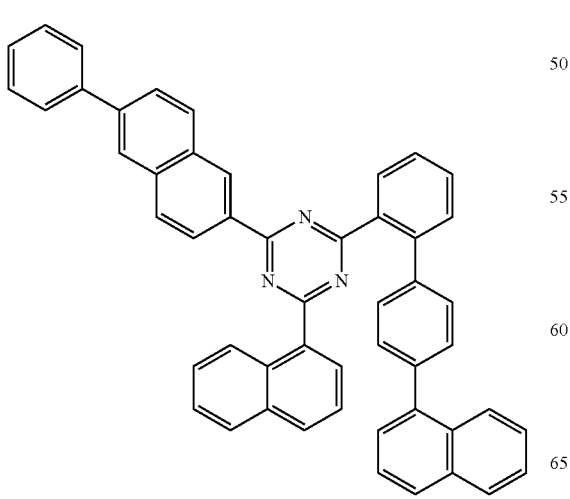
S-47
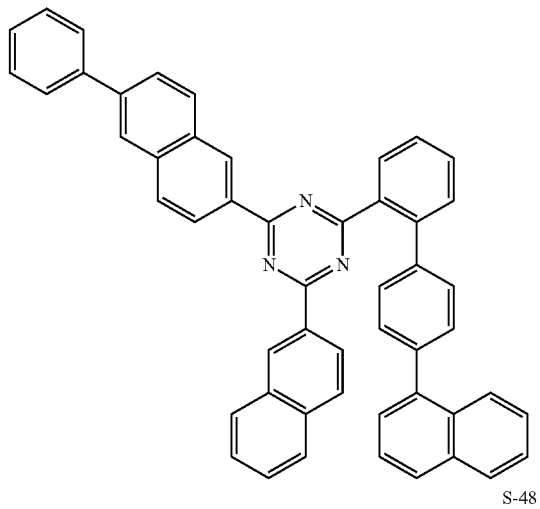
S-48
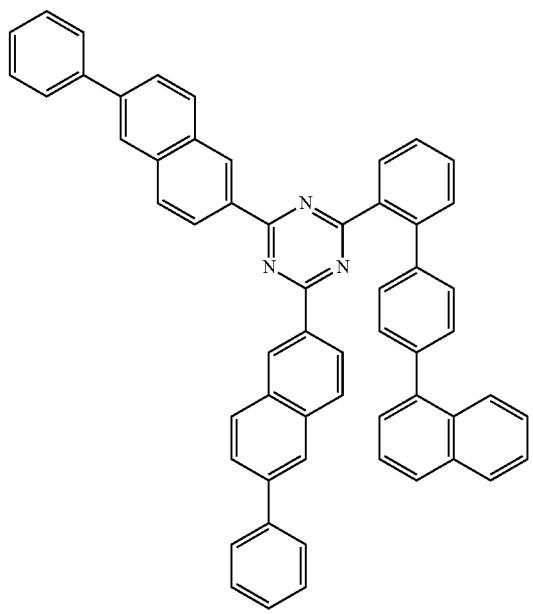
S-49
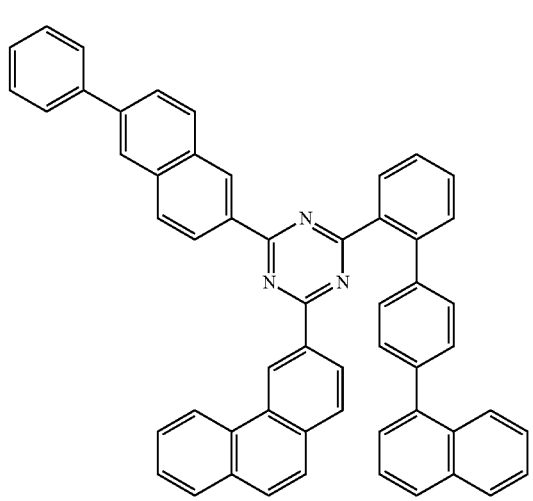

S-50
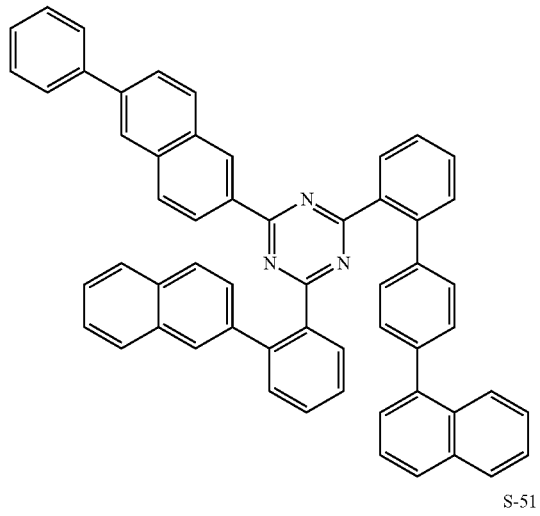
S-53
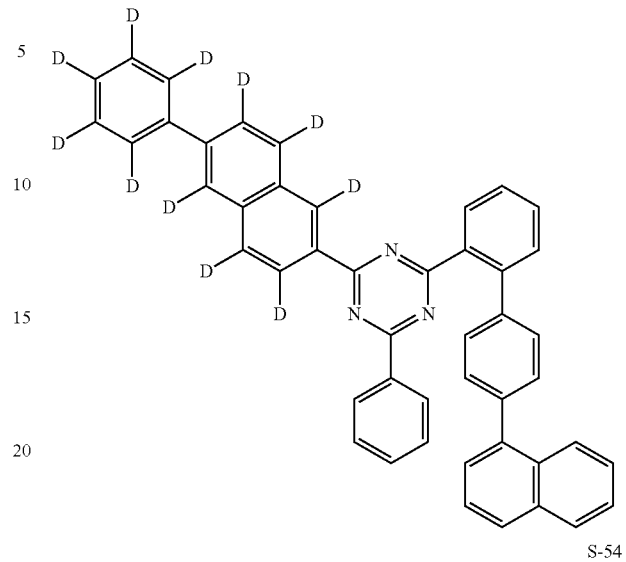
S-51
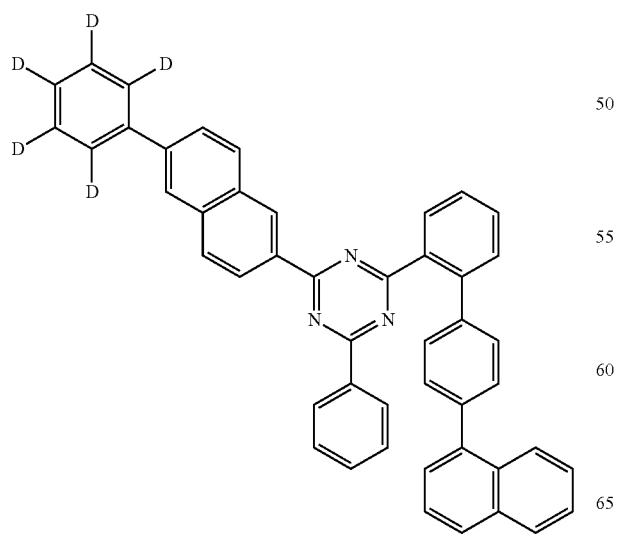
S-54
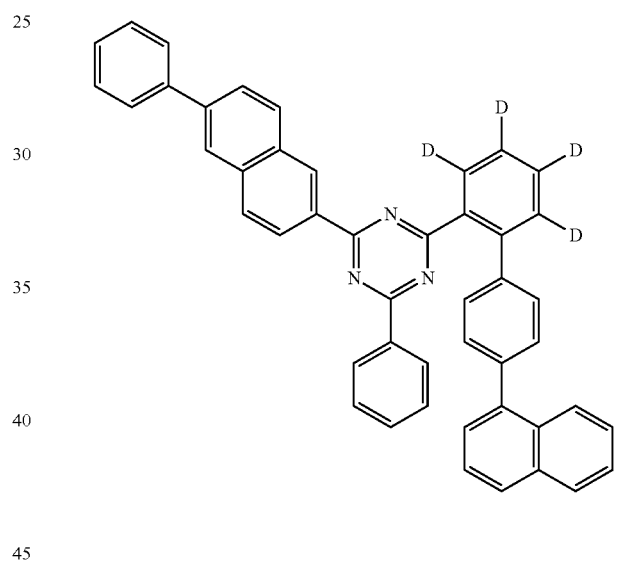
S-52
S-55
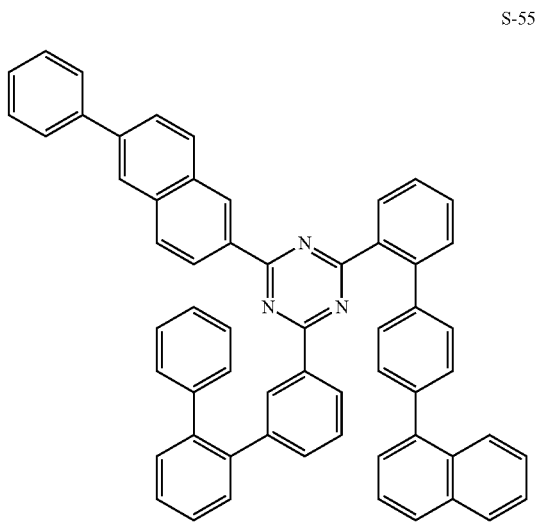

S-56

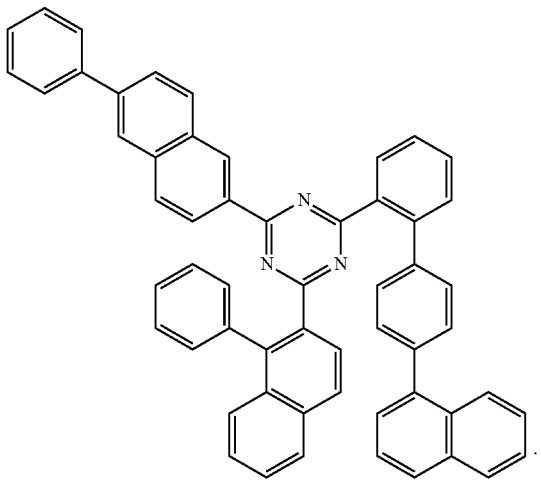

5. The compound of claim 1, wherein Reorganization Energy value of the compound is 0.240 to 0.300.

6. An organic electronic element comprising a first electrode, a second electrode, and an organic material layer formed between the first electrode and the second electrode, wherein the organic material layer comprises an emitting layer, a hole blocking layer and an electron transport layer, wherein the emitting layer, the hole blocking layer or the electron transport layer comprises a compound represented by Formula (2) of claim 1.

7. The organic electronic element of claim 6, wherein the emitting layer comprises the compound represented by Formula (2).

8. The organic electronic element of claim 6, wherein the emitting layer comprises a first host compound and a second host compound, and the first host compound or the second host compound comprises a compound represented by Formula (2).

9. The organic electronic element of claim 6, further comprising a light efficiency enhancing layer formed on at least one surface of the first electrode and the second electrode, being opposite to and not facing the organic material layer.

10. The organic electronic element of claim 6, wherein the organic material layer comprise 2 or more stacks each of which comprise a hole transport layer, an emitting layer, and an electron transport layer sequentially formed on the first electrode.

11. The organic electronic element of claim 10, wherein the organic material layer further comprises a charge generating layer formed between the 2 or more stacks.

12. An electronic device comprising: a display device including the organic electronic element of claim 6; and a control unit for driving the display device.

13. The electronic device of claim 12, wherein the organic electronic element is any one of an organic electroluminescent device (OLED), an organic solar cell, an organic photoreceptor (OPC), an organic transistor (organic TFT), and an element for monochromic or white illumination.

* * * * *